(12) United States Patent
Dudits et al.

(10) Patent No.: US 7,790,956 B2
(45) Date of Patent: Sep. 7, 2010

(54) PLANTS HAVING IMPROVED GROWTH CHARACTERISTICS AND METHODS FOR MAKING THE SAME BY MODULATING EXPRESSION OF A NUCLEIC ACID SEQUENCE ENCODING A NAP1-LIKE PROTEIN

(75) Inventors: Denes Dudits, Szeged (HU); Attila Feher, Szeged (HU); Valerie Frankard, Sint-Genesius-Rode (BE)

(73) Assignee: CropDesign N.V., Zwijnaarde (BE)

( * ) Notice: Subject to any disclaimer, the term of this patent is extended or adjusted under 35 U.S.C. 154(b) by 631 days.

(21) Appl. No.: 11/547,395

(22) PCT Filed: Mar. 25, 2005

(86) PCT No.: PCT/EP2005/051403

§ 371 (c)(1),
(2), (4) Date: Oct. 20, 2006

(87) PCT Pub. No.: WO2005/094562

PCT Pub. Date: Oct. 13, 2005

(65) Prior Publication Data

US 2008/0271200 A1 Oct. 30, 2008

Related U.S. Application Data

(60) Provisional application No. 60/563,847, filed on Apr. 20, 2004.

(30) Foreign Application Priority Data

Apr. 2, 2004 (EP) ................................. 04101388

(51) Int. Cl.
*C12N 15/82* (2006.01)
*A01H 5/00* (2006.01)

(52) U.S. Cl. ........................ 800/290; 800/278; 800/298; 435/468

(58) Field of Classification Search ....................... None
See application file for complete search history.

(56) References Cited

U.S. PATENT DOCUMENTS

2006/0150283 A1 * 7/2006 Alexandrov et al. ........ 800/288

FOREIGN PATENT DOCUMENTS

EP          1 033 405 A2    9/2000
WO       WO 03/020936   *  3/2003

OTHER PUBLICATIONS

Dong et al. Regulation of biosynthesis and introcellular localization of rice and tobacco homologues of nucleosome assembly protein 1. (2003) Planta; vol. 216; pp. 561-570.*
Hobe et al. A tool for understanding homologous recombination in plants. (2003) Plant Cell Reports; vol. 21; pp. 1135-1142.*
Dong, A., et al., "Regulation of Biosynthesis and Intracellular Localization of Rice and Tobacco Homologues of Nucleosome Assembly Protein 1", Planta, 2003, vol. 216, pp. 561-570.
Shinn, P., et al., "*Arabidopsis thaliana* At1g74560/F1M20__24 mRNA, Complete cds", EMBL Database Accession No. AF385720, Jun. 9, 2001.

* cited by examiner

*Primary Examiner*—Cathy Kingdon Worley
(74) *Attorney, Agent, or Firm*—Connolly Bove Lodge & Hutz LLP

(57) ABSTRACT

The present invention concerns a method for improving growth characteristics of plants by modulating expression of a nucleic acid sequence encoding a NAP1-like protein. The invention also relates to transgenic plants having improved growth characteristics, which plants have modulated expression of a nucleic acid encoding a NAP1-like protein.

8 Claims, 18 Drawing Sheets

```
########################################
#=======================================

# Aligned_sequences: 2
# 1: AtNAP1
# 2: MsNAP1
# Matrix: EBLOSUM62
# Gap_penalty: 10.0
# Extend_penalty: 0.5

# Length: 264
# Identity:     188/264 (71.2%)
# Similarity:   223/264 (84.5%)
# Gaps:          12/264 ( 4.5%)
# Score: 983.0

#=======================================
```

```
AtNAP1         1 MVADKSKKSKIEEKGEEENLEQIDAELVLSIEKLQEIQDDLEKINEKASD     50
                 ||||||||.|:.|||  ||.|:||.||||||||||||||::|||||:|||
MsNAP1         1 MVADKSKKLKVSEKG--ENAEEIDGELVLSIEKLQEIQDEIEKINEEASD     48

AtNAP1        51 EVLEVEQKYNVIRKPVYDKRNEVIQSIPGFWMTAFLSHPALGDLLTEEDQ    100
                 :|||:||||.:||||||||||:||:|||.||:|||||||||||.||||.||||
MsNAP1        49 KVLEIEQKYNEVRKPVYDKRNDVIKSIPDFWLTAFLSHPVLGDLLNEEDQ     98

AtNAP1       101 KIFKYLNSLEVEDAKDVKSGYSITFHFTSNPFFEDAKLTKTFTFLEEGTT    150
                 ||||:|.||||||.||||||||||||||:|.|||||||:||.||||||||||
MsNAP1        99 KIFKHLISLEVEDHKDVKSGYSITFNFDSNPFFEDSKLVKTFTFLEEGTT    148

AtNAP1       151 KITATPIKWKEGKGLPNGVNHDDKKGNKRALPEESFFTWFTDAQHKEDAG    200
                 |:|||||||||||:||||.| :||||||||||..:.||||||.|.:.|::.|
MsNAP1       149 KLTATPIKWKEGKGIPNGVIH-EKKGNKRAASDISFFTWFCDTEQKDEMG    197

AtNAP1       201 DEIHDEVADIIKEDLWSNPLTYFN----NDADEEDFDGDDDG-DEEGEED    245
                 | ||||:|::||:|||.|||.|||     ::|:|||.:..|.| |:::..||
MsNAP1       198 D-IHDEIAEMIKDDLWPNPLNYFNSEDPDEAEEEDDEAGDAGKDDDDSED    246

AtNAP1       246 DDDEEEEDGEE    256
                 |||:|::|.:|
MsNAP1       247 DDDQEDDDDDEEEE    260

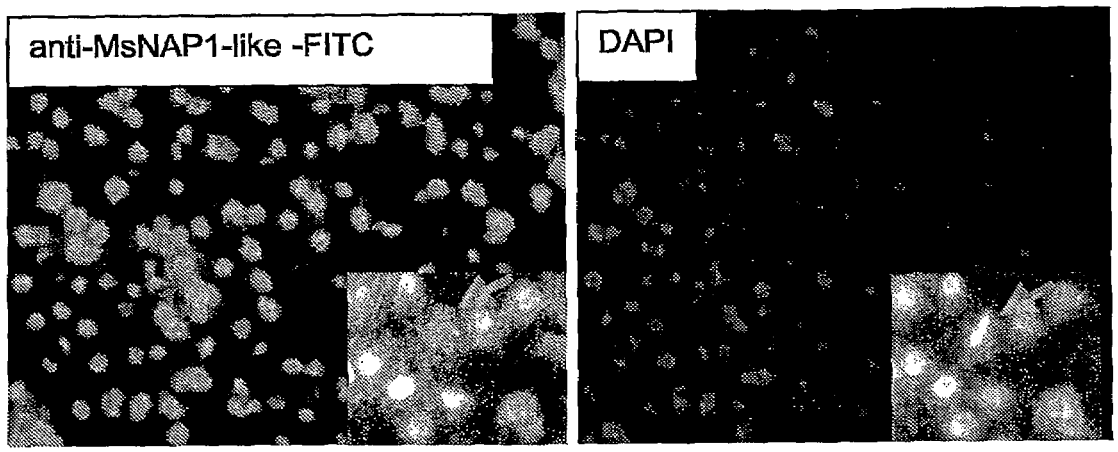
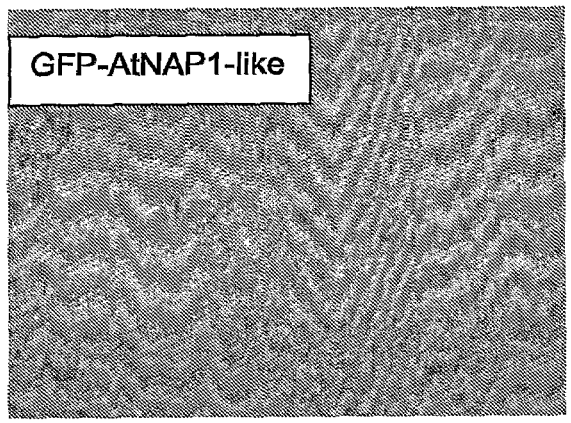
FIGURE 6

SEQ ID NO:1, coding sequence for *Arabidopsis thaliana* NAP1-like protein (AtNAP1), start and stop codon in bold gtgacggaaccacaagaagagaagagaccaaaaggaggagccaaaatcctctctttcttt
ggaattagggtttcctcaaggaagtgaactgaaaatggtcgcggacaagagcaagaagt
cgaaaattgaagagaaaggcgaagaagaaaacttggagcaaatcgacgcagagcttgttc
tctcaattgagaagcttcaggagattcaagacgacctcgagaagattaacgaaaaggcca
gtgacgaggtcttggaagtagagcagaaatataacgtgatacggaaacctgtctatgaca
agcgcaatgaagttatccaatcgattcctggcttttggatgactgcttttttgagtcatc
ctgccttaggcgacctcttgactgaagaagaccaaaagatttttaagtacttgaactctc
tggaagtggaggatgccaaagatgtgaaatctggatactctataacttttcacttcactt
caaacccgttctttgaggatgccaagcttaccaagacatttactttccttgaagaaggaa
caacaaaaatcactgcaactcctatcaaatggaaggagggcaaggcttgccaaatggag
tgaaccatgatgataagaaaggaaataaacgtgcattgccagaggagagtttcttttactt
ggtttactgatgctcaacataaggaagatgctggggatgagattcatgatgaggttgctg
atattatcaaggaagatctctggtccaaccctctcacctacttcaacaatgatgctgatg
aagaggattttgatggagatgatgatggtgacgaagagggagaagaagacgatgacgatg
aagaggaggaagatggtgaggaatgatgggagcccaaagataacacattgctggcttgct
tctataacagatgtgtaaagtttgtgttatgaggttctcaattttagcaatgatgagact
aagctttctcttttggaatatttagtttatttactatcaatagctacattctgtttgtac
gaaccatgtcatcatccatgtcctaaatcttgccataactacatctgttttttcgc

SEQ ID NO:2, *Arabidopsis thaliana* NAP1-like (AtNAP1), deduced protein sequence MVADKSKKSKIEEKGEEENLEQIDAELVLSIEKLQEIQDDLEKINEKASDEVLEVEQKYN
VIRKPVYDKRNEVIQSIPGFWMTAFLSHPALGDLLTEEDQKIFKYLNSLEVEDAKDVKSG
YSITFHFTSNPFFEDAKLTKTFTFLEEGTTKITATPIKWKEGKGLPNGVNHDDKKGNKRA
LPEESFFTWFTDAQHKEDAGDEIHDEVADIIKEDLWSNPLTYFNNDADEEDFDGDDDGDE
EGEEDDDDEEEEDGEE

SEQ ID NO:3, expression cassette (PRO0129::CDS0406 (*Arabidopsis thaliana* NAP1-like (AtNAP1a)) - T-zein - T-rbsc-deltaGA terminator; 1-2193: GOS2 promoter, 2246-3016: NAP1-like CDS, 3126-3320: T-Zein terminator, 3364-3560: T-rbs terminator aatccgaaaagtttctgcaccgttttcaccccctaactaacaatatagggaacgtgtgct
aaatataaaatgagaccttatatatgtagcgctgataactagaactatgcaagaaaaact
catccacctactttagtggcaatcgggctaaataaaaagagtcgctacactagtttcgt
tttccttagtaattaagtgggaaaatgaaatcattattgcttagaatatacgttcacatc
tctgtcatgaagttaaattattcgaggtagccataattgtcatcaaactcttcttgaata
aaaaaatctttctagctgaactcaatgggtaaagagagagatttttttaaaaaaataga
atgaagatattctgaacgtattggcaaagatttaaacatataattatataattttatagt

FIGURE 8

```
ttgtgcattcgtcatatcgcacatcattaaggacatgtcttactccatcccaattttat
ttagtaattaaagacaattgacttattttattatttatctttttcgattagatgcaag
gtacttacgcacacactttgtgctcatgtgcatgtgtgagtgcacctcctcaatacacgt
tcaactagcaacacatctctaatatcactcgcctatttaatacatttaggtagcaatatc
tgaattcaagcactccaccatcaccagaccacttttaataatatctaaaatacaaaaaat
aattttacagaatagcatgaaaagtatgaaacgaactatttaggttttcacatacaaaa
aaaaaagaattttgctcgtgcgcgagcgccaatctcccatattgggcacacaggcaaca
acagagtggctgcccacagaacaacccacaaaaacgatgatctaacggaggacagcaag
tccgcaacaaccttttaacagcaggctttgcggccaggagagaggaggagaggcaaagaa
aaccaagcatcctcctcctccatctataaattcctccccctttcccctctctatata
ggaggcatccaagccaagaagagggagagcaccaaggacacgcgactagcagaagccgag
cgaccgccttcttcgatccatatcttccggtcgagttcttggtcgatctcttccctcctc
cacctcctcctcacagggtatgtgcccttcggttgttcttggatttattgttctaggttg
tgtagtacggcgttgatgttaggaaaggggatctgtatctgtgatgattcctgttcttg
gatttgggatagaggggttcttgatgttgcatgttatcggttcggtttgattagtagtat
ggttttcaatcgtctggagagctctatggaaatgaaatggtttagggtacggaatcttgc
gatttgtgagtaccttttgtttgaggtaaaatcagagcaccggtgattttgcttggtgt
aataaaagtacggttgtttggtcctcgattctggtagtgatgcttctcgatttgacgaag
ctatcctttgtttattccctattgaacaaaaataatccaactttgaagacggtcccgttg
atgagattgaatgattgattcttaagcctgtccaaaatttcgcagctggcttgtttagat
acagtagtccccatcacgaaattcatggaaacagttataatcctcaggaacaggggattc
cctgttcttccgatttgcttagtcccagaatttttttcccaaatatcttaaaaagtca
ctttctggttcagttcaatgaattgattgctacaaataatgcttttatagcgttatccta
gctgtagttcagttaataggtaatacccctatagtttagtcaggagaagaacttatccga
tttctgatctccattttaattatatgaaatgaactgtagcataagcagtattcatttgg
attattttttttattagctctcacccctcattattctgagctgaaagtctggcatgaac
tgtcctcaattttgttttcaaattcacatcgattatctatgcattatcctcttgtatcta
cctgtagaagtttcttttttggttattccttgactgcttgattacagaaagaaatttatga
agctgtaatcgggatagttatactgcttgttcttatgattcatttcctttgtgcagttct
tggtgtagcttgccactttcaccagcaaagttcatttaaatcaactagggatatcacaag
tttgtacaaaaaagcaggctTCACAatggtcgcggacaagagcaagaagtcgaaaattga
agagaaaggcgaagaagaaaacttggagcaaatcgacgcagagcttgttctctcaattga
gaagcttcaggagattcaagacgacctcgagaagattaacgaaaaggccagtgacgaggt
cttggaagtagagcagaaatataacgtgatacggaaacctgtctatgacaagcgcaatga
agttatccaatcgattcctggcttttggatgactgcttttttgagtcatcctgccttagg
cgacctcttgactgaagaagaccaaaagatttttaagtacttgaactctctggaagtgga
ggatgccaagatgtgaaatctggatactctataacttttcacttcacttcaaacccgtt
ctttgaggatgccaagcttaccaagacatttactttccttgaagaaggaacaacaaaaat
cactgcaactcctatcaaatggaaggagggcaagggcttgccaaatggagtgaaccatga
tgataagaaaggaaataaacgtgcattgccagaggagagtttctttacttggtttactga
tgctcaacataaggaagatgctggggatgagattcatgatgaggttgctgatattatcaa
ggaagatctctggtccaacccctctcacctacttcaacaatgatgctgatgaagaggattt
tgatggagatgatgatggtgacgaagagggagaagaagacgatgacgatgaagaggagga
agatggtgaggaatgatgggacccagctttcttgtacaaagtggtgatatcacaagcccg
```

FIGURE 8 (continued)

```
ggcggtcttctagggataacagggtaattatatccctctagatcacaagcccgggcggtc
ttctacgatgattgagtaataatgtgtcacgcatcaccatgggtggcagtgtcagtgtga
gcaatgacctgaatgaacaattgaatgaaagaaaaaagtactccatctgttccaaat
taaaattcattttaaccttttaataggtttatacaataattgatatatgttttctgtata
tgtctaatttgttatcatccggcggtcttctagggataacagggtaattatatccctct
agacaacacacaacaaataagagaaaaaacaaataatattaatttgagaatgaacaaaag
gaccatatcattcattaactcttctccatccatttccatttcacagttcgatagcgaaaa
ccgaataaaaaacacagtaaattacaagcacaacaaatggtacaagaaaaacagttttcc
caatgccataatactcgaac
```

SEQ ID NO:4, Sense primer prm1505

GGGGACAAGTTTGTACAAAAAAGCAGGCTTCACAATGGTCGCGGACAAGAG

SEQ ID NO:5, Reverse primer prm1506

GGGGACCACTTTGTACAAGAAAGCTGGGTCCCATCATTCCTCACCATC

SEQ ID NO:6, Nicotiana tabacum NAP1-like, start and stop codon in bold and underlined (NtNAP1a)

```
agcggctggtaccggtccggaattcccgggatatcgtcgacccacgcgtccgaaagaaga
gaaaagatgggtgctgacaagggaagaagcaaaaagtggaggaagagaacaacaccat
tgatggtgagctcgttttttccattgaaaaattgcaagaaatacaagacgagctcgagaa
gatcaatgaggaagcaagtgataaagtattggaagtggaacagaagtacaatgagatccg
caagcctgtctatgacaaacgaacgacatcattaaagctatccggacttctggttgac
tgctttttttgagtcatcctgtcctaggtgaacttctaactgaagaagaccaaaagatctt
caagtttctaagttctattgaagttgaagactctaaagatgtgaagtcgggctactcgat
aaccttaacttcaatgcgaatccttattttgaaaatacaaagctcacaaagacctatac
cttccttgaagatggacccacaaagatttctgctacaacaataaaatggaaagaaggcat
gggcattcctaatggatttgcacatgagaagaaaggaaacaagcgatctcatgctgagga
aagcttcttcacatggttcagtgaagtcaatcaaaagatgaggatgaggatgaggccct
agagattcaggatgaggtcgctgacataattaaggatgacttgtggccgaaccctctcac
ctattttaacaacgagcctgatgaagaagattttgatggtgacgagggaaggacagtga
aggctctgaagacgaagaggaagaagaagaggaggatgaggatggtgatgaatgaag
gcagtaaactgttcaagacccctattttgggatctcgtcttcagcggttttaatcatcag
ggtttaatgtctgtaaagaggctttgaatgttgccaaagaacagaataactgtggtgact
ataccttttcttctcttgtatggttataacttataagcaaaatatctaattccggaggtt
ccaaaatgttttcattaggctagttcgattaatgaagtgtttgtctggcaaaaactgata
atgttaggttattgagttatg
```

SEQ ID NO:7, Nicotiana tabacum NAP1-like (NtNAP1a), deduced protein sequence

MGADKGKKQKVEEENNTIDGELVFSIEKLQEIQDELEKINEEASDKVLEVEQKYNEIRKP
VYDKRNDIIKAIPDFWLTAFLSHPVLGELLTEEDQKIFKFLSSIEVEDSKDVKSGYSITF
NFNANPYFENTKLTKTYTFLEDGPTKISATTIKWKEGMGIPNGFAHEKKGNKRSHAEESF
FTWFSEVNQKDEDEDEALEIQDEVADIIKDDLWPNPLTYFNNEPDEEDFDGDEGKDSEGS
EDEEEEEEEDEDGDEE

SEQ ID NO:8, Nicotiana tabacum NAP1-like, start and stop codon in bold and underlined (NtNAP1b)

tttgtacaaaaaagcaggctggtaccggtccggaattcccgggatatcgtcgacccacgc
gtccgagaaattagcagttagagacactgagaagcagcagctctcttcctcagctgctgt
gtgcttaggcaaagaataaaatgggggcagacaaagggaagaagcagaaagtggatgagg
aaaacaacaatgttattgatgaaaagctcatttttccattgaaaaattgcaagagatac
aagacgagctcgagaagatcaatgaaaagcaagcgacgaagtgttggaagtagaacaga
agtacaacgagatccgcaagcctgtctacgataagcgaaatgatgtcattagctctattt
ctgacttctggttgactgcttttttgagtcatcctgttcttggtaaccttctcactgaag
aggaccaaaagattttcaaatttgtaagttctattgaagtggaagactcaaaggatgtga
aatcgggtcattcaatcacgtttaactttaagcccaatccttatttgaaaattcaaagc
tctcaaagacgtataccttccttgaagatggacctacaaaaattacagctacaacaataa
aatggaaagaaggcatgggcattcctaatggagttgctgacaagaagaaaggaaacaagc
ggtcccacgctgaagaaagtttctttacatggttcagtgaagtcaatcaaaaggtgatg
tggatgatgacgaaatgagattctggacattcaggatgatgaggttgctgaaataatca
aggatgacttgtggcctaaccctctcaattattttgaccatgagcctgatgaagaagata
ttgagggcgatgagggaaaggacagcggaggctctgaagaggaagaagaagaggaagatg
atgaagatgaagaagacgaatgaactgttggtagaccttgtgtttgatttgagttctcat
cagtgtttcaatcatcagagttggtctctgtaaagaggtttcggatattgcagaaaatt
gaatgacatatagtggtgactctaattttagtttcagtga

SEQ ID NO:9, Nicotiana tabacum NAP1-like (NtNAP1b), deduced protein sequence

MGADKGKKQKVDEENNNVIDEKLIFSIEKLQEIQDELEKINEKASDEVLEVEQKYNEIRK
PVYDKRNDVISSISDFWLTAFLSHPVLGNLLTEEDQKIFKFVSSIEVEDSKDVKSGHSIT
FNFKPNPYFENSKLSKTYTFLEDGPTKITATTIKWKEGMGIPNGVADKKKGNKRSHAEES
FFTWFSEVNQKGDVDDDENEILDIQDDEVAEIIKDDLWPNPLNYFDHEPDEEDIEGDEGK
DSGGSEEEEEEEDDEDEEDE

FIGURE 8 (continued)

SEQ ID NO:10, Medicago sativa NAP1-like (Ms10.1), start and stop codon in bold and underlined

GGCACGAGCAAAACCCTAACACTTCCCTCATTCACGCTCGAAGAAAAGAACACAAATCTC
TCCACTGCGCTAGGGTTTGAAACCCAACACCTTCTGTTTCTTCAACC<u>ATG</u>GTGGCCGACA
AGTCTAAGAAGTTGAAAGTTTCTGAAAAGGGTGAAAACGCTGAAGAGATCGACGGAGAAC
TTGTTCTCTCCATTGAAAAGTTGCAGGAAATTCAAGATGAGATTGAAAAGATCAATGAGG
AGGCTAGCGATAAAGTTCTCGAAATAGAGCAGAAGTACAATGAAGTAAGGAAACCGGTGT
ATGACAAGCGCAATGATGTGATCAAGTCCATTCCCGATTTCTGGCTAACTGCGTTTTTGA
GCCATCCTGTTCTTGGTGATCTCTTGAATGAAGAAGATCAGAAGATATTTAAGCATTTAA
TCTCTCTTGAGGTGGAAGATCATAAAGATGTTAAATCAGGCTATTCAATCACATTTAACT
TCGACTCCAATCCCTTTTTTGAGGATTCAAAACTTGTTAAGACTTTTACCTTCCTTGAAG
AAGGAACCACAAAGCTTACCGCCACACCCATAAAATGGAAAGAGGGCAAGGGCATTCCCA
ATGGAGTTATTCATGAGAAGAAAGGGAACAAGCGAGCTGCTTCTGATATCAGTTTCTTTA
CCTGGTTTTGTGACACTGAGCAGAAAGATGAAATGGGTGACATTCATGATGAGATTGCTG
AAATGATCAAGGATGATTTATGGCCGAATCCACTCAATTATTTCAACAGTGAGGACCCTG
ATGAAGCAGAGGAGGAGGATGATGAAGCTGGTGATGCGGGAAGGATGATGATGACTCTG
AAGATGATGATGATCAAGAGGATGACGACGATGACGAGGAAGAAGAA<u>TAG</u>TGTAAAATGC
TTTAAAATAGTAATACTTGGTTTTAATTTATTTATTTTAAGGTTATTATAGGAGTATCTT
AGTGGTCTTTAGGGGATGATGAAAGACCAAGGTTGGCTATTGGTTTTCCCCCTNTGGGCG
TAAACCTTATTTATTGTGCTTTGAAGGTGATTTCTGGTTTTATCTTTGTGCGCTTCTTTC
AAGATACCAA<u>TGA</u>TACATCGGATTTTATCTTAGTCCTATATTGAAACCATATAGTAGTTA
AAATGTAGTATATTCAGTGTATAGCTGCGTAATCAGTATCATTTTATTGCTATCACAACT
TTACAGTACC

SEQ ID NO:11, Medicago sativa NAP1-like (Ms10.1), deduced protein sequence

MVADKSKKLKVSEKGENAEEIDGELVLSIEKLQEIQDEIEKINEEASDKVLEIEQKYNEV
RKPVYDKRNDVIKSIPDFWLTAFLSHPVLGDLLNEEDQKIFKHLISLEVEDHKDVKSGYS
ITFNFDSNPFFEDSKLVKTFTFLEEGTTKLTATPIKWKEGKGIPNGVIHEKKGNKRAASD
ISFFTWFCDTEQKDEMGDIHDEIAEMIKDDLWPNPLNYFNSEDPDEAEEEDDEAGDAGKD
DDDSEDDDDQEDDDDDEEEE

SEQ ID NO:12, Zea mays nfa104 coding sequence (GenBank accession AF384036)

gttcctaccttcttccctccgtctcccagctcgcgcaggcaggcgacacagcgacgctaa
aaaccctagagcgaggaggcgtgccaggccagcggtttgcgatgacggcaccggcggaca
agggggaagaaggccaagaccgatgccgacggcggcgaggagaacgagcaaatcgacggcg
ccttgtcttctccatcgagaagctccaggagattcaggacgagctcgagaaggttaatg
aggaagcaagtgacaaggttatggaggtggagcagaaatacagtgagattcgcagacctg
tctatctcaagagggtgacattatcaagaccatcccggacttttggctcacagcgtttt
tgagccatcctctactaagtgagcttctgactgaagaggatcagaagatattcaagtact

FIGURE 8 (continued)

```
tggactccattgatgtcgatgattctgatgttaaggcaggatattccatttaccttaact
tctctgagaacccgtactttgaagacacaaagcttacaaagacctattcctttgttgatg
atggaacaaccacaataaaagcttctcaaattaagtggaaggatggaatgggacctgcaa
atggaaatggtattaacaagaagggaaacaagcggccattagtagtggaaagttttttct
cctggtttagtgatacagagctcaagagtcttgctgatggtgtgcaagatgaggtggcgg
agatcatcaaggaagacttgtggcctaatcctttgaagtacttcaacaatgaggttgaag
atgaatttgaaggagatgaagaagatgatgacgacgacgacgatgataatttggatg
gtgatgacaatgacgatgatggggaccaggagaactgagccctcgcgtttaggcggggaa
ttatgtg
```

SEQ ID NO:13, Zea mays nfa104 deduced protein sequence (GenBank accession AAK67146)

MTAPADKGKKAKTDADGGEENEQIDGALVFSIEKLQEIQDELEKVNEEASDKVMEVEQKY
SEIRRPVYLKRGDIIKTIPDFWLTAFLSHPLLSELLTEEDQKIFKYLDSIDVDDSDVKAG
YSIYLNFSENPYFEDTKLTKTYSFVDDGTTTIKASQIKWKDGMGPANGNGINKKGNKRPL
VVESFFSWFSDTELKSLADGVQDEVAEIIKEDLWPNPLKYFNNEVEDEFEGDEEDDDDDD
DDDNLDGDDNDDDGDQEN

SEQ ID NO:14, Oryza sativa NAP1-like (OsNAP1a), coding sequence (GenBank accession XM_472746)

```
atggcggcggcggagcagaaggggaagaagccgaggaccgacggcgcggaggccgagccc
gtcgacgccgccctgctgcagtccatcgagaagctccaggagatccaggacgagatcgag
aaggttaatgaggaagcatgtgataaagttctggagttggaacagaaatacaacgaggtt
cgcagaccagtttatgttcgacggaataaaattatcaagcaaattcctgacttctggctg
acagcgtttcttagccatcctatgcttggtgaactattaactgaagatgatcaaaagatt
ttcaaacacttggagtctatcgacgtggatgactcagaagatatcaaatcaggctactcc
attactctcacattctcccccaatccatattttgaagatacaaagcttacaaaaacatat
tcctttagtgacgatgaagcagtcaaagtaaaggctacctccatcaggtggaagaaagga
atggatattgccaatgatcgtgcgtacacgaagaagggggacaagcgaatcttaattgat
gaaagtttctttacttggttcaatagtgaaaagaacagaagttttgctcatggagctatg
gatgaggtggcagatgtcatcaaggaagatctgtggcctaatcctttgaagtacttcaac
aatgaatttgaagaagaattagagctactggatgacgatgacgaggtatctgatgatgac
gatgaggaggaggatgatgaagaccaaggtgaaggagaggaggatggagaggagaactga
```

SEQ ID NO:15, Oryza sativa NAP1-like (OsNAP1a), deduced protein sequence (GenBank accession XP_472746)

MAAAEQKGKKPRTDGAEAEPVDAALLQSIEKLQEIQDEIEKVNEEACDKVLELEQKYNEV
RRPVYVRRNKIIKQIPDFWLTAFLSHPMLGELLTEDDQKIFKHLESIDVDDSEDIKSGYS
ITLTFSPNPYFEDTKLTKTYSFSDDEAVKVKATSIRWKKGMDIANDRAYTKKGDKRILID
ESFFTWFNSEKNRSFAHGAMDEVADVIKEDLWPNPLKYFNNEFEEELELLDDDDEVSDDD
DEEEDDEDQGEGEEDGEEN

FIGURE 8 (continued)

SEQ ID NO:16, Oryza sativa NAP1-like (OsNAP1b) coding sequence (GenBank accession XM_506840)

```
ctccgctctcctccagctccgcctccgacgcgcgcacgcctctccctccctcctcctcc
gcctcgcctcgcagtgtggaagaaaggaaggaaggctaaaaccctagcgagcgcgcgagc
gagcgagggctctctgcttccttgcgatgacggcgccggcggacaaggggaagaaggcca
agaccgacgccgacggcggcgccgccgaggagaacgagcagatcgacggcgcctcgtcc
tctccatcgagaagctccaggagatccaggacgagctcgagaaggtcaatgaggaagcta
gtgacaaggttttggaggtcgagcagaaatacagtgagattcgcagacctgtctatctcc
gaaggagtgacgttatccaaacaatcccgacttctggctgacagcgtttctgagtcatc
ctctacttagtgagcttttgaccgaagaggatcaaaagatgttcaagtacctggagtctg
tcgacgtggatgattctaaagatgtcaagtcaggctactccataactcttaccttctccg
agaacccgtactttgaagacaaagagctcacgaagacatatgccttcgctgatgacggaa
caaccacaataaatgctactagcattaagtggaagaaggaatggaaattgcaaatggga
atgccaagaagaaagggagcaagcgaccattggttgaggaaagtttcttcacctggttta
ctgatacagagcacaagagtcttgctgatggtgtgcaagatgaggtggctgagatcatca
aggaagacctgtggcccaatccattgaagtatttcaataatgaggctgaagagttaggag
aggatgacgacgaagaggggtctgatgctgatgagggtgaagaggatgaggaggaggaga
actgagtctaggatgtcagattgcgatggtgccgatcgtctgcattttgtggatgctgtc
actctgaagggcgaagttgcgtgaccctcggttgcttctttcttttttcttttgatgac
ttagctggaacccttaggaactgtttaatgccttatggagtccgtcgtatttcgactca
aaggagacacctctatatcataatctgcgtataaccatggaagacattttaacctgctga
tgtgtggttcattgcgctgcctctggtgctgtagggtgttcgttcctttgtgctctctgt
ctttttttttttttttgtgtgtgtggtcgcgctggcattgttgccagtctgatgggc
tgttatttctcccctagaaagagtgaaaaacctggcttgtgatcattgtttacg
```

SEQ ID NO:17, Oryza sativa NAP1-like (OsNAP1b), deduced protein sequence (GenBank accession XP_506840)

MTAPADKGKKAKTDADGGAAEENEQIDGALVLSIEKLQEIQDELEKVNEEASDKVLEVEQ
KYSEIRRPVYLRRSDVIQTIPDFWLTAFLSHPLLSELLTEEDQKMFKYLESVDVDDSKDV
KSGYSITLTFSENPYFEDKELTKTYAFADDGTTTINATSIKWKEGMEIANGNAKKKGSKR
PLVEESFFTWFTDTEHKSLADGVQDEVAEIIKEDLWPNPLKYFNNEAEELGEDDDEEGSD
ADEGEEDEEEEN

SEQ ID NO:18, Zea mays nfa103 coding sequence (GenBank accession AF384035)

```
ccaaaagggtcacagttccgcctccttttcctgccttcctcctcactagtcgctcccccg
cggctcgcgcaggcgggcgacacaacgaggctaaatccctatcgcgaggaggcgtgtgag
gccagcggctttgcgatgacagcaccagcggacaaggggaagaaggccaagactgatgcc
gacggcggcgaggagaacgaacagatcgacggcgtcctcgtcctctccatcgagaagctc
caggagatacaggacgagctcgagaaggtaaatgaggaagcaagtgacaaggttatggag
gtggagcagaaatacagtgagatccgcagacctgtctatctcaagagggtgacattatc
```

FIGURE 8 (continued)

```
aagaccatcccggacttttggctcacagcgtttatgagccatcctctattaagtgagctt
ctgactgaagaggaccagaagatattcaagtacttagactccattgatgtggatgattct
gatgttaaggcaggatactccattcatcttaacttctctgagaacccgtactttgaggac
acaaagcttgcaaagacctatatctttgctgatgatggaacaaccacaataaaagcttcc
gaaattaagtggaaggaaggaatgggacctgcaaatggaaatggtattaacaagaagggg
agtaagcggccattagtagaggaaagttttttagctggtttggtgatacagagctcaag
agtcttgctgatggtgtgcaagatgaggtggcggagatcataaaggaagatttgtggcct
aatcctttgaagtacttcaacaatgaggttgacgatgaatttgaaggagatgaagatgat
gatgatttggatggtgatgatgacgatgaaggcgatgatttggagaactgagcccttgcg
cttggttcagaatgttgtccgtggatgatgtggctgggcggaactgtgacccttttgg
```

SEQ ID NO:19, Zea mays nfa103 deduced protein sequence (GenBank accession AAK67145)

```
MTAPADKGKKAKTDADGGEENEQIDGVLVLSIEKLQEIQDELEKVNEEASDKVMEVEQKY
SEIRRPVYLKRGDIIKTIPDFWLTAFMSHPLLSELLTEEDQKIFKYLDSIDVDDSDVKAG
YSIHLNFSENPYFEDTKLAKTYIFADDGTTTIKASEIKWKEGMGPANGNGINKKGSKRPL
VEESFFSWFGDTELKSLADGVQDEVAEIIKEDLWPNPLKYFNNEVDDEFEGDEDDDDLDG
DDDDEGDDLEN
```

SEQ ID NO:20, coding sequence for Arabidopsis thaliana NAP1-like protein (GenBank accession NM_101738)

```
agattcacgcatcacacaatcgagtttttagggttttagcggttgctctctcggaagcca
gagagaagagggaagaggaagtctaattcctctgcgttttttgcaattagggttttctca
attggaatcgaaaatggtgacagacaagagcaagaaggcgaaaaccgaagaagaaaacgt
cgagcaaatcgatgcagagcttgtcctctcaatcgaaaagcttcaagagatccaagacga
cctcgagaagataaatgaaaggctagtgatgaagtgttggaagtggagcagaaatataa
tgtgataaggaaacctgtttatgacaagcgtaacgagatcatcaaaaccatccctgattt
ctggttaactgctttcttgagtcaccctgctttaggtgaacttttgactgaagaagacca
aaagattttcaaatatcttagctctcttgatgttgaggatgccaagatgtgaaatctgg
atactctatcacttttttccttcaatcccaatccatttttgaagatggaaaactgacaaa
gacttttacctttctcgaagaagggacaaccaaaatcacagccacgcctatcaaatggaa
agagggcaaaggcctggcgaatggagtgaatcatgagaagaatggaaacaaacgtgcact
acctgaagagagcttctttacctggtttagtgatgctcaacacaaggaggatgttgagga
tgagatgcaagacgagcaggttgcagatcatcaaggaagatttgtgcccaaccctct
cacctacttcaacaatgacgctgatgaagaggactttgatggagacgatgatggagatga
agaggagaagaaggtgactctgatgaagatgatgacgaagaagacgaagttggtgagga
atgatggcagggatacccagaaaccacatttgcttacatgtcttctctataacagagtgt
gtaaagttttgtgtgttgaaggttttaattttaagcaaagtggattatgacgacaac
agacaagcttttaattttatttaccgtaatagttatatcttgttgtaagaaaccattt
cagccttttgttggaaaatcctgcttaaatggttttgagtcttacataatagcttcttc
atcttttgtcttcttaaagagaattatatttgtaatttcatgtctgttgtgtttctttga
ctttactgaatagagaatttgtgtgtttatggtgaaaatatagccgatctgcttgac
```

FIGURE 8 (continued)

**SEQ ID NO:21, *Arabidopsis thaliana* NAP1-like, deduced protein sequence (GenBank accession NP_564063)**

MVTDKSKKAKTEEENVEQIDAELVLSIEKLQEIQDDLEKINEKASDEVLEVEQKYNVIRK
PVYDKRNEIIKTIPDFWLTAFLSHPALGELLTEEDQKIFKYLSSLDVEDAKDVKSGYSIT
FSFNPNPFFEDGKLTKTFTFLEEGTTKITATPIKWKEGKGLANGVNHEKNGNKRALPEES
FFTWFSDAQHKEDVEDEMQDEQVADIIKEDLWPNPLTYFNNDADEEDFDGDDDGDEEEKE
GDSDEDDDEEDEVGEE

**SEQ ID NO:22, *Lycopersicon esculentum* NAP1-like coding sequence protein (LeNAP1, GenBank accession BT013059)**

gcgaaatcaagaaaatcagttaagcagctctgtaactcaggtgggaaaaggcaaaaat
aatggtggttgacaaagggaagaagcagaaagtggaagaggaaagctacattgatgaaaa
gctcatttttccattgaaaaattgcaagaaatacaagacgaccttgacaagatcaatga
gaaagcaagtgaggaagtgttggaaatagaacagaagtacaacaagatccgcaagcctgt
ttatgataagcggaatgatatcattaactctatttctgacttctggttgactgcttttt
gagtcatcctgttcttggtgaccttctaactgaagaggaccaaaagattttcaaattctt
aagttctattgaagtggaagactcgaagatgtgaaatttggttactaatcacgtttaa
ctttaagcccaatcctttctttgaaaattcaaagctctcaaagacctataccttccttga
agatggacctacaaaatcacagctacaccaataaaatggaagaaggcaaaggcattcc
taatggcgttgctcaggagaagaaggaaacaagcgatcccatgctgaagagagcttctt
cacctggttcagtgaagtcaataaaaagatgatagcgatgatgatgaaaatgaggttct
ggagattcaggatgaggttgctgaataatcaaggatgacttgtggccaaacccttaac
ttattttaccaatgaacctgatgaagaagattttgagggtgatgaaggtggtgatgaggg
ggaggactctgaagatgaaggtgatgaggaggaagaggaagacgacgaagatgaagatga
caaatgaactgttaatggacctcatatttgatttgatttctcttcttcaatgtttcaatt
atcatagttggtatctgtaaagaagcttaatattgcagataaaatcgaattatatagt
ggtgactgcttttttctaaaaaaaaaaaaaaaaaaaaaaaaa

**SEQ ID NO:23, *Lycopersicon esculentum* NAP1-like deduced protein sequence (LeNAP1)**

MVVDKGKKQKVEEESYIDEKLIFSIEKLQEIQDDLDKINEKASEEVLEIEQKYNKIRKPV
YDKRNDIINSISDFWLTAFLSHPVLGDLLTEEDQKIFKFLSSIEVEDSKDVKFGYSITFN
FKPNPFFENSKLSKTYTFLEDGPTKITATPIKWKEGKGIPNGVAQEKKGNKRSHAEESFF
TWFSEVNKKDDSDDDENEVLEIQDEVAEIIKDDLWPNPLTYFTNEPDEEDFEGDEGGDEG
EDSEDEGDEEEEEDDEDEDDK

**SEQ ID NO:24, coding sequence for *Arabidopsis thaliana* NAP1-like protein (GenBank accession NM_118744)**

gtccctagtctcttctgcttcttcttcttcaaaatctctctcttcaccaaatcctcagaa
gatgagcaacgacaaggatagcttcaacgtctccgatcttactgctgctcttaaggacga
ggatcgagctggccttgtcaatgctctaaagaacaagctgcagaatctggctggtcagcg

FIGURE 8 (continued)

```
ttctgatgtgctcgagaatctgactcccaatgtgagaaagcgcgttgatgccttgaggga
tatacagagccaacatgatgaactagaggcaaaattccgtgaggagagagctattcttga
agccaagtatcaaacgctgtatcagcctttgtatgtcaagcgttatgagattgtgaatgg
cactactgaagttgaactggctccagaggatgataccaaggtggaccaaggagaggagaa
aactgcagaagagaaaggagttccaagtttctggctgacagctctgaaaaataacgatgt
tatttccgaggaggtcacagagcgtgatgaagggctctcaaatatcttaaagatattaa
gtggtgcaagattgaagagcctaaaggattcaaacttgagttttctttgacacgaatcc
gtattttaagaacactgtcttgacaaagtcttatcatatgattgatgaagatgagccact
gcttgagaaggctatggggacagaaattgattggtatcctggaaagtgtctaactcagaa
gattctcaagaagaagcctaagaaaggttcaaagaatactaaaccaatcaccaaactcga
agattgtgaagcttcttcaacttctttagtcctccagaagttccggatgaagatgaaga
tatcgacgaggaaagagctgaggatcttcaaaacctgatggaacaagattatgacatcgg
atctactattcggggaaaagattattcctcgtgctgtctcatggtttactggtgaggctat
ggaagcagaggattttgaaatagatgacgatgaggaagatgacattgatgaggatgaaga
tgaggaagacgaagaggatgaggaggacgatgatgatgaggatgaagaagaaagcaagac
caaaaagaagccatcaatcggcaacaagaagggagggagatctcagatagttggtgaagg
taaacaagatgagaggccacccgaatgcaagcaacagtaatcttttactacgctctacca
gacataaaaggattgcgtgaaaatataattcaggtcattctctgttcatcaagaatgagg
attgagaaaaggttttgggattttaaaagtgaaattcatcttgtaggagtttcgttcgt
ttttctattggtgtgtttattttctctaaagcactttaataatataccttggtatttaat
ttatgaatcaagcatcatcatccctagtctctgcattcactacttcatccctacctaaa
cttttgtcgacgaaagagattttaataaccatttagatagtaatgggtagtgggaatgatc
attattcttttgttcaccgtcctttgattttcaatggtaaccattttgttgtgtaag
```
SEQ ID NO:25
, *Arabidopsis thaliana* NAP1-like, deduced protein sequence (GenBank accession NP_194341)

```
msndkdsfnvsdltaalkdedraglvnalknklqnlagqrsdvlenltpnvrkrvdalrd
iqsqhdeleakfreeraileakyqtlyqplyvkryeivngttevelapeddtkvdqgeek
taeekgvpsfwltalknndviseevterdegalkylkdikwckieepkgfklefffdtnp
yfkntvltksyhmidedepllekamgteidwypgkcltqkilkkkpkkgskntkpitkle
dcesffnffsppevpdededideeraedlqnlmeqdydigstirekiipravswftgeam
eaedfeidddeeddidededeedeedeeddddedeeesktkkkpsignkkggrsqivgeg
kqderppeckqq
```

SEQ ID NO:26, coding sequence for *Arabidopsis thaliana* NAP1-like protein (GenBank accession NM_127506)

```
GTGTCTTATTTCGGTCTGGTCATTTTCTCAAAGCCCTTTTAGTTATTTATATATATATTC
TCTGTCTCGTATTTGTCCCCAAAAATCTAGGGTTTTAAGGTTTCTTATCCTTCCTCTTCC
TCCGCCAGATTCTTTTCTTGCGAAGATGAGCAACGACAAGGACAGCATGAACATGTCCGA
TCTCTCCACCGCTCTTAACGAGGAGGATCGTGCCGGGCTTGTTAATGCTCTTAAGAACAA
GTTGCAGAATTTGGCTGGACAACACTCTGATGTCCTTGAAAACTTGACTCCACCAGTCAG
GAAGCGTGTCGAGTTTCTAAGAGAGATTCAGAACCAATATGATGAGATGGAAGCAAAATT
CTTTGAGGAGAGAGCAGCTCTTGAAGCTAAGTATCAAAAGTTATATCAGCCTTTATATAC
```

```
CAAGCGATATGAGATTGTGAATGGTGTGGTCGAAGTTGAAGGTGCAGCTGAAGAAGTAAA
ATCCGAACAAGGAGAAGATAAATCAGCTGAAGAGAAAGGAGTACCAGATTTCTGGCTTAT
TGCATTGAAGAACAATGAAATTACTGCGGAAGAGATAACTGAGCGAGATGAAGGGGCTCT
CAAGTATCTCAAAGATATCAAGTGGAGTAGGGTTGAAGAACCAAAAGGGTTCAAGCTTGA
GTTTTTCTTTGATCAGAATCCTTACTTCAAGAACACTGTCTTGACCAAGACATATCACAT
GATTGATGAAGATGAGCCTATCCTTGAGAAGGCCCTCGGGACGGAGATTGAGTGGTATCC
TGGAAAGTGTTTGACACAGAAGATTCTAAAAAGAAGCCAAAGAAAGGATCCAAAAACAC
AAAGCCGATCACTAAGACTGAGGACTGTGAGAGTTTCTTCAACTTTTTCAGTCCACCTCA
AGTTCCTGACGATGATGAGGATCTTGATGATGACATGGCTGATGAACTCCAAGGACAAAT
GGAGCATGATTATGATATCGGTTCAACAATCAAAGAGAAATCATCTCGCATGCTGTGTC
ATGGTTCACTGGTGAAGCTGTTGAGGCAGATGACCTTGATATTGAGGACGACGATGATGA
GATTGATGAAGATGATGATGAAGAGGACGAGGAAGATGATGAGGATGACGAGGAGGAGGA
TGATGAGGATGATGACGAGGAGGAAGAAGCAGATCAAGGAAAGAAGAGCAAAAGAAGTC
ATCAGCTGGGCACAAGAAGGCTGGAAGAAGTCAACTTGCGGAAGGTCAAGCAGGTGAGAG
GCCACCGGAATGTAAGCAGCAGTGAAGAAGTGAAGAATCTTGGCTTAGTTATGATGAAGA
AGAAGAGTGAAGAGTGTCTTTGAGCCGAGGTTGTGTTTCTTTAATTTGCAGAGTCATGGT
CCGGTTTATTATATATCAGTTTTGGGTGATTGGTTTGCTATTTAAAAAAAAAAAATGGGT
TCTTTGGTTTGGTTTGTGTCTCTTGATTTTTCCTTTTGTAATGATCTTATGAATTTGTTT
CGAGTTAATGTCGTTCTCTGGTCAGATTTCGAATTCAATTCTATTTATCCTCCCTCGTTA
ATGAGAGAATTTGTG
```

SEQ ID NO:27, Arabidopsis thaliana NAP1-like, deduced protein sequence (GenBank accession NP_179538)

```
MSNDKDSMNMSDLSTALNEEDRAGLVNALKNKLQNLAGQHSDVLENLTPPVRKRVEFLRE
IQNQYDEMEAKFFEERAALEAKYQKLYQPLYTKRYEIVNGVVEVEGAAEEVKSEQGEDKS
AEEKGVPDFWLIALKNNEITAEEITERDEGALKYLKDIKWSRVEEPKGFKLEFFFDQNPY
FKNTVLTKTYHMIDEDEPILEKALGTEIEWYPGKCLTQKILKKKPKKGSKNTKPITKTED
CESFFNFFSPPQVPDDDEDLDDDMADELQGQMEHDYDIGSTIKEKIISHAVSWFTGEAVE
ADDLDIEDDDDEIDEDDDEEDEEDDEDDEEEDDEDDDEEEEADQGKKSKKKSSAGHKKAG
RSQLAEGQAGERPPECKQQ
```

SEQ ID NO:28, coding sequence for Arabidopsis thaliana NAP1-like protein (GenBank accession NM_125077)

```
GCCACCCAGAAAAAACCCTCAAGTCTTCTTCTTCTTCCTCAATCTCTCCACCTCTTTTCA
AACCTTCTTCACACTCTCTCTCAATCAATCCTTTTCTTCTCAAATCTTTCAGTTTTGAT
CTCTAAATTTCCAGAAAATGAGCAACGATAAGGACAGTTTCAATGTCAGCGATCTCACTT
CTGCTCTTAAAGATGAGGATCGAGCTGGTCTTGTCAACGCTCTTAAGAACAAGCTCCAGA
ATCTAGCTGGACAACATTCTGATGTGCTCGAGAATCTGACTCCTAAAATTAGAAGGCGTG
TTGAGGTTTTGCGGGAGATTCAGGGCAAACATGATGAAATAGAGACAAAATTCCGCGAGG
AGAGAGCTGCTCTTGAAGCCAAGTATCAAAAGTTATATCAGCCTTTGTATAACAAGCGTT
ATGAGATTGTGAATGGAGCTACTGAAGTTGAAGGGGCTCCAGAGGATGCTAAGATGGACC
AAGGAGACGAGAAAACTGCAGAAGAGAAAGGAGTCCCTAGTTTCTGGCTGACTGCTCTGA
```

FIGURE 8 (continued)

```
AAAATAATGATGTTATATCTGAAGAGATCACAGAGCGTGATGAAGGAGCCCTTATATATC
TTAAAGATATCAAGTGGTGCAAGATTGAAGAACCAAAGGGATTCAAACTTGAGTTTTTCT
TCGACCAGAATCCTTACTTCAAAAACACCCTATTAACAAAGGCGTATCATATGATTGATG
AAGATGAGCCTCTGCTTGAGAAGGCTATTGGGACAGAGATTGATTGGTATCCTGGAAAAT
GCTTAACTCAGAAGATTCTTAAGAAGAAGCCTAAGAAAGGTGCAAAGAATGCCAAGCCAA
TTACCAAAACTGAAGATTGTGAAAGCTTCTTCAACTTCTTCAATCCTCCCCAAGTTCCTG
ATGATGATGAAGACATTGACGAAGAAGAGCCGAGGAACTTCAGAATCTGATGGAACAAG
ATTATGACATTGGTTCTACAATCCGGGAGAAGATCATACCTCATGCTGTCTCATGGTTTA
CTGGTGAGGCTATTGAGGGAGAGGAGTTTGAAATAGACAATGACGATGAAGATGATATCG
ATGAGGATGAAGATGAGGATGAAGAAGATGAAGACGAAGATGAGGAAGAAGACGACGAAG
ATGAGGAGGAAGAAGTAAGCAAGACCAAAAAGAAGCCATCAGTCTTACACAAGAAAGGAG
GGAGACCTCAGGTTACCGATGATCAACAAGGAGAGAGGCCTCCTGAATGCAAACAACAGT
AAACAAAATCGAAAAGTCTAAACGAAACCAGTAAAAGAAAAACAAATGTTTTGGGTTTT
GAGTGAAGTTTCATGGCCTAGTTTTTTGCTTCCATGTAAGGCAAAATGTTTTGAAGACTG
CTCATAGGAATGTTGCTGTAGGCAAAAGAGTGAGTTTCTCCATGTGGAGATACTTGATAA
ATTATTTTTGGTGCATTTGTTTTTTTTTTTTAATCACTAAGTTGAATTTTGGTGTGTT
CGTCAAAATTATATCTTTTTACCACTTGAATTAAGTCTCTTTTGGTTTCTTTAATTTAAA
AATAAATAAATCTTATCATTGTTTTTTTTGTGTGGACATAAGTGTATTATTCTTATTGTA
AACC
```

SEQ ID NO:29, *Arabidopsis thaliana* NAP1-like, deduced protein sequence (GenBank accession NP_568844)

```
MSNDKDSFNVSDLTSALKDEDRAGLVNALKNKLQNLAGQHSDVLENLTPKIRRRVEVLRE
IQGKHDEIETKFREERAALEAKYQKLYQPLYNKRYEIVNGATEVEGAPEDAKMDQGDEKT
AEEKGVPSFWLTALKNNDVISEEITERDEGALIYLKDIKWCKIEEPKGFKLEFFFDQNPY
FKNTLLTKAYHMIDEDEPLLEKAIGTEIDWYPGKCLTQKILKKKPKKGAKNAKPITKTED
CESFFNFFNPPQVPDDDEDIDEERAEELQNLMEQDYDIGSTIREKIIPHAVSWFTGEAIE
GEEFEIDNDDEDDIDEDEDEEDEDEDEEEDDEDEEEEVSKTKKKPSVLHKKGGRPQVT
DDQQGERPPECKQQ
```

SEQ ID NO:30, coding sequence for *Arabidopsis thaliana* NAP1-like protein (GenBank accession NM_112230)

```
ATGAGCAACGAAGAAAACATCAAATCTGATAATAAGAGCGGCGATTCCTCTGATCTCCCT
ACCATTCCCGCCTTAGATATTGGGGCAGAGGAATGTGATCTTCTTGCAGAGCTTAAGGCA
AGTCACTTCAAATTGTTGATAAAAATTCACACAAACCTAACCTTAAAGCGACCATTTGAT
GTGAAAAAACTCTCACCTAAAGTTACCAAACGTGTTCTGTTCCTCAAAGACATTCAGGTT
ACACACGATGAACTCGAAGAGAAGTTTCTTGCTGAGAAATCTGCATTGGAGGCAACATAT
GATAATCTCTACAAGCCGCTTTTTGCTAAGAGGTATGAAATTGTGAATGGTGTGGTCGAA
GCTGAAGCAGAGAAAGAAGGAGTTCCCAATTTCTGGTTGATTGCAATGAAAACCAATGAA
ATGCTCGCAAATGAGATAACGGAAAGAGATGAGGCAGCATTGAAGTATCTTAAGGACATC
AGATCTTGCAGAGTTGAAGACACTTCAAGAAATTTCAAGCTGGAGTTTCTCTTTGATTCT
AATCTTTACTTCAAGAACTCGGTTCTGTCTAAAACTTACCATGTGAACGATGAAGATGGT
```

```
CCTGTTCTTGAGAAAGTGATTGGAACGGACATAGAATGGTTTCCAGGTAAATGTTTGACT
CATAAGGTTGTTGTGAAGAAGAAAACAAAGAAAGGGCCAAAGAAGGTCAACAACATCCCC
ATGACCAAAACAGAAAACTGCGAGAGTTTCTTCAATTTCTTCAAGCCACCTGAGATTCCT
GAGATTGATGAAGTTGACGATTACGATGATTTTGATACCATTATGACGGAAGAACTACAA
AACCTGATGGACCAAGACTATGACATTGCTGTGACAATCCGAGATAAACTGATCCCTCAT
GCAGTTTCATGGTTTACGGGAGAGGCTCTTGTTGATGAAGACGATTCTGATGATAATGAT
GATGATGATAATGATGAGAAGAGTGACTAA
```

SEQ ID NO:31, *Arabidopsis thaliana* NAP1-like, deduced protein sequence (GenBank accession NP_187993)

```
MSNEENIKSDNKSGDSSDLPTIPALDIGAEECDLLAELKASHFKLLIKIHTNLTLKRPFD
VKKLSPKVTKRVLFLKDIQVTHDELEEKFLAEKSALEATYDNLYKPLFAKRYEIVNGVVE
AEAEKEGVPNFWLIAMKTNEMLANEITERDEAALKYLKDIRSCRVEDTSRNFKLEFLFDS
NLYFKNSVLSKTYHVNDEDGPVLEKVIGTDIEWFPGKCLTHKVVVKKKTKKGPKKVNNIP
MTKTENCESFFNFFKPPEIPEIDEVDDYDDFDTIMTEELQNLMDQDYDIAVTIRDKLIPH
AVSWFTGEALVDEDDSDDNDDDNDEKSD
```

SEQ ID NO: 32, NAP domain of the protein sequence encoded by at1g74560 (SEQ ID NO: 2), the signature is indicated in italics

```
IEKLQEIQDDLEKINEKASDEVLEVEQKYNVIRKPVYDKRNEVIQSIPGFWMTAFLSHPA
LGDLLTEEDQKIFKYLNSLEVEDAKDVKSGYSITFHFTSNPFFEDAKLTKTFTFLEEGTT
KITATPIKWKEGKGLPNGVNHDDKKGNKRALPEE*SFFTWFT*DAQHKEDAGDEIHDEVADI
IKEDLWSNPLTYFNNDADE
```

SEQ ID NO:33
SIEKLQEIQD

PLANTS HAVING IMPROVED GROWTH CHARACTERISTICS AND METHODS FOR MAKING THE SAME BY MODULATING EXPRESSION OF A NUCLEIC ACID SEQUENCE ENCODING A NAP1-LIKE PROTEIN

RELATED APPLICATIONS

This application is a national stage application (under 35 U.S.C. 371) of PCT/EP2005/051403 filed Mar. 25, 2005, which claims benefit of European application 04101388.9 filed Apr. 2, 2004 and U.S. provisional application 60/563,847 filed Apr. 20, 2004.

The present invention concerns a method for improving growth characteristics, and in particular for increasing yield of a plant. More specifically, the present invention concerns a method for increasing yield by modulating expression in a plant of a nucleic acid encoding a protein homologous to the Nucleosome Assembly Protein 1 (NAP1-like protein). The present invention also concerns plants having modulated expression of a nucleic acid encoding a NAP1-like protein, which plants have increased yield relative to corresponding wild type plants.

Given the ever-increasing world population, and the dwindling area of land available for agriculture, it remains a major goal to improve the efficiency of agriculture and to increase the diversity of plants in horticulture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic complements that may not always result in the desirable trait being passed on from parent plants. Advances in molecular biology have allowed mankind to manipulate the germplasm of animals and plants. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits. Traits of particular economic interest are growth characteristics such as high yield.

NAP proteins form a family of related proteins that are known in animals and are reported to be involved in chromatin-related activities. The family of NAP proteins is characterised by the presence of a conserved sequence known as the NAP domain. The NAP domain is described in the Pfam (accession PF00956) and Interpro databases (accession IPR002164). NAP is a component of a multifactor complex that mediates DNA packaging into nucleosomes (Krude, T. and Keller, C. (2001) Cell. Mol. Life Sci. 58, 665-672). During the S phase of the eukaryotic cell division cycle, newly replicated DNA is rapidly assembled into chromatin. This process requires the coordinated action of several factors. In the initial stages, CAF1 (chromatin assembly factor 1) binds histone proteins H3 and H4 and directs them to the replication fork via PCNA binding. Subsequent deposition of histone proteins H2A and H2B is mediated by NAP1 proteins. NAP1 was first described in HeLA cells (von Lindern et al. (1992) Mol. Cell. Biol. 12, 3346-3355) and was later found conserved in all eukaryotes. In addition, NAP proteins are thought to regulate gene transcription and may influence cell differentiation and development.

SET proteins are highly related to NAP proteins and play a role in various cellular processes in humans. In human cells, SET has been shown to be associated with various CDK-cyclin complexes during the regulation of the cell cycle, such as G2/M transition. SET is a potent inhibitor of Protein Phosphatase 2A (PP2A) that is involved in several signalling pathways. The inhibitory activity of SET could be attributed to an acidic C-terminal domain (Canela et al. (2003) J. Biol. Chem. 278, 1158-1164). Other reports show the involvement of SET in DNA repair and transcription. SET is part of a complex that has DNA binding and bending activities mediated by the chromatin-associated protein HMG2. HMG2 facilitates the assembly of nucleoprotein higher-order structures by bending and looping DNA or by stabilizing underwound DNA. HMG2 co-precipitates with SET (Fan et al. (2002) Mol. Cell. Biol. 22, 2810-2820). SET is also reported to inhibit active DNA demethylation (Cervoni et al. (2002) J. Biol. Chem. 277, 25026-25031). The oncoprotein Set/TAF-I, involved in the inhibition of histone acetylation, also inhibits demethylation of ectopically methylated DNA resulting in gene silencing. Set/TAF-I is suggested to play a role in integrating epigenetic states of histones and DNA in gene regulation.

The activity of NAP1 proteins is in part regulated by phosphorylation. It was shown that subcellular localization of NAP1 in *Drosophila* is dependent on its phosphorylation state, which may be controlled by Casein Kinase II (Rodriguez at al (2000) J. Mol. Biol. 298, 225-238). Mammals are reported to possess several NAP1 proteins, while in yeast there is only one known NAP1 protein.

Plant NAP1 orthologues remain largely unknown, although NAP1 proteins were reported from soybean (Yoon et al (1995) Mol. Gen. Genet. 249, 465-473), *Arabidopsis*, tobacco, maize and rice (Dong et al. (2003) Planta 216, 561-570). Phylogenetic analysis of plant NAP1-like genes has revealed that there are two subgroups, one related to NAP1 and the other to the SET protein (FIG. 1). Most likely, later sequence divergence may have occurred since the two *Arabidopsis*, the two maize and the two tobacco sequences cluster together pointing to a more recent gene duplication effect. The *Saccharomyces cerevisiae* genome contains only one NAP-encoding gene, combining the functional properties of both the NAP1 and SET subgroups. Similarly, Template Activating Factor 1 (TAF-I), a homologue of NAP1, combines both PP2a inhibiting activity (Saito et al., Biochem. Biophys. Res. Comm. 259, 471-475, 1999) and chromatin remodelling activity (Kawase et al., Genes Cells 1, 1045-1056, 1996). It is therefore likely that the plant proteins of the NAP/SET family are largely redundant in function, particularly in the group of SET proteins where a lower degree of divergence is observed compared to the NAP group. Furthermore, there is structural evidence that NAP and SET proteins belong to the same family since they share the NAP domain which is followed by a C-terminal acidic region.

Little is known about the function of NAP1-like proteins in plants, although a role in mitosis and cytokinesis has been proposed (Dong et al 2003). The plant orthologues of the NAP1 protein most likely play a different role than their animal counterparts. Based on its nuclear localisation and on sequence similarities with the mammalian SET protein, a role in chromatin remodelling may be expected for the plant proteins. Furthermore, the plant NAP/SET group of proteins could be involved in the regulation of PP2A in plants. PP2A is one of the major phosphatases in plants, acting to a large extent on transcription factors and protein kinases, and proposed to regulate activity of proteins involved in a variety of cellular processes, including cell cycle (Ayaydin et al. (2000) Plant J. 23, 85-96), hormonal actions such as ABA mediated stomatal movement, germination (Kwak et al. (2002) Plant Cell 14, 2849-2861), or auxin transport and root development (Garbers et al 1996 EMBO J. 15, 2115-2124). PP2A is furthermore reported to be involved in photosynthesis and light signalling (Sheen (1993) EMBO J. 12, 3497-3505) and in nitrogen assimilation (Hirose and Yamaya (1999) Plant Physiology 121, 805-812).

To date, no effects on agronomic traits have been described upon modulating the expression of NAP1-like proteins in plants. It has now surprisingly been found that modulating expression of a nucleic acid encoding a NAP1-like protein in a plant gives plants having improved growth and development, in particular increased yield, more particularly increased seed yield when compared to corresponding wild type plants. Therefore according to a first embodiment of the present invention there is provided a method for improving growth and development of a plant, comprising introducing a genetic modification in a plant and selecting for modulated expression in this plant of a nucleic acid sequence encoding a NAP1-like protein. In particular, improved growth and development is increased yield of a plant, more particularly increased seed yield; and the modulated expression is increased expression.

The term NAP1-like protein, as defined herein, refers to any protein comprising a NAP domain and an acidic C-terminal region and having PP2a phosphatase inhibiting activity. The term "NAP domain" as used herein is as defined by the Pfam database by accession number PF00956 (http://www.sanger.ac.uk/Software/Pfam/; Bateman et al., Nucleic Acids Research 30(1):276-280 (2002), see for example Table 1). Preferably, NAP1-like protein sequences useful in the present invention have a NAP domain comprising a (T/S)FF(T/N/S/E/D)(W/F)(L/F) (SEQ ID NO: 34 signature and/or the conserved amino acid sequence as given in SEQ ID NO:33. More preferably the NAP domain is as represented by SEQ ID NO: 32. The term "acidic C-terminal region" or "acidic C-terminus" as used herein refers to the carboxy-terminal end of the protein, which carboxy-terminal end is about 20 to 25 amino acids long, of which at least 13 residues are glutamic and/or aspartic acid.

TABLE 1

Examples of *Arabidopsis* proteins comprising a NAP1 domain

| Gene ID | Pfam profile | Position | Score | e-value | SEQ ID NO: |
|---|---|---|---|---|---|
| at1g18800 | PF00956 | 27-224 | 147.7 | 2e-40 | 20, 21 |
| at1g74560 | PF00956 | 31-229 | 135.0 | 1.3e-36 | 1, 2 |
| at2g19480 | PF00956 | 52-300 | 457.4 | 1.2e-133 | 26, 27 |
| at5g56950 | PF00956 | 52-300 | 473.2 | 2.2e-138 | 28, 29 |
| at4g26110 | PF00956 | 52-301 | 503.4 | 1.7e-147 | 24, 25 |
| at3g13782 | PF00956 | 69-311 | 300.7 | 1.7e-86 | 30, 31 |

Optionally, the NAP1-like protein useful in the methods of the present invention has, besides being an inhibitor of PP2a phosphatases, also chromatin remodelling activities. Methods for measuring inhibition of PP2a phosphatases are known in the art and comprise, for example, assays based on commercially available dye-labelled or fluorochrome-labelled substrates or assays based on measurement of radioactivity in TCA soluble fractions after treatment of [$^{32}$P]-labelled histone H1 with PP2a phosphatase (Saito et al. (1999) Biochem. Biophys. Res. Comm. 259, 471-475) or of radioactivity released from labelled myelin basic protein (Li et al, J. Biol. Chem. 271, 11059-11062, 1996). An alternative method for measuring NAP1-like protein activity is given in Example 6, which is based on the method described by Ulloa et al. (FEBS Letters 330, 85-89, 1993). Chromatin remodelling activities may be assayed in several ways, such as measurement of DNA-binding activity in a gel retardation assay (Fan et al., 2002) or as measurement of histone-binding activity using ELISA (Rodriguez et al. (1997) Genomics 44, 253-265). DNA bending activity may be determined in a ligase-mediated circularization assay (Fan et al., 2002) or in a supercoiling assay (Fujii-Nakata et al. (1992) J. Biol. Chem. 267, 20980-20986; Yoon et al. (1995), Mol. Gen. Gen. 249, 465-473).

Preferably, the NAP1-like protein, comprising a NAP domain and an acidic C-terminal region as described above, is of plant origin. The NAP1-like protein is preferably from a dicotyledonous plant, preferably from the family of Brassicaceae, more preferably from *Arabidopsis thaliana*, most preferably the NAP1-like protein is a protein as represented by SEQ ID NO: 2 or is a homologue, derivative or active fragment thereof, which homologues, derivatives or active fragments comprise a NAP domain and the acidic C-terminus as described above, and which homologues, derivatives or active fragments furthermore have PP2A inhibiting activity. Preferably the NAP1-like proteins are encoded by a nucleic acid as represented by SEQ ID NO: 1 or a nucleic acid capable of hybridising therewith.

The term "NAP1-like protein" includes proteins homologous to the protein presented in SEQ ID NO: 2. Preferred homologues to be used in the methods of the present invention comprise a NAP domain and an acidic C-terminus as described above. Preferably the homologues have a NAP domain comprising a (T/S)FF(T/N/S/E/D)(W/F)(L/F) (SEQ ID NO: 34) signature and/or the conserved sequence of SEQ ID NO:33, and an acidic C-terminus of 20 to 25 residues comprising at least 13 aspartic and/or glutamic acid residues. Additionally, the NAP1 homologues have PP2a inhibiting activity and possess optionally also chromatin-remodelling activities, which can be measured as described above.

Homologues of SEQ ID NO: 2 may be found in various eukaryotic organisms. The closest homologues are generally found in the plant kingdom. Homologues of SEQ ID NO: 2 suitable in the methods of the present invention include two tobacco proteins (SEQ ID NO: 7 and 9), a tomato protein (SEQ ID NO: 23), an alfalfa protein (SEQ ID NO: 11), the *Arabidopsis* protein represented by SEQ ID NO: 21. Other homologues suitable for practising the method according to the invention include for example the *Zea mays* homologues nfa104 (Accession No. AF384036, SEQ ID NO: 13) and nfa103 (Accession No. AF384035, SEQ ID NO: 19); or the *Oryza sativa* homologues (SEQ ID NO: 15 and 17).

Methods for the search and identification of NAP1-like homologues would be well within the realm of persons skilled in the art. Such methods comprise comparison of the sequences represented by SEQ ID NO: 1 or 2, in a computer readable format, with sequences that are available in public databases such as MIPS (http://mips.gsf.de/), GenBank (http://www.ncbi.nlm.nih.gov/Genbank/index.html) or EMBL Nucleotide Sequence Database (http://www.ebi.ac.uk/embl/index.html), using algorithms well known in the art for the alignment or comparison of sequences, such as GAP (Needleman and Wunsch, J. Mol. Biol. 48; 443-453 (1970)), BESTFIT (using the local homology algorithm of Smith and Waterman (Advances in Applied Mathematics 2; 482-489 (1981))), BLAST (Altschul, S. F., Gish, W., Miller, W., Myers, E. W. & Lipman, D. J., J. Mol. Biol. 215:403-410 (1990)), FASTA and TFASTA (W. R. Pearson and D. J. Lipman Proc. Natl. Acad. Sci. USA 85:2444-2448 (1988)). The software for performing BLAST analysis is publicly available through the National Centre for Biotechnology Information. The abovementioned homologues were identified using blast default parameters (BLOSUM62 matrix, gap opening penalty 11 and gap extension penalty 1) and preferably the full length sequences are used for analysis. Alternatively, only the NAP1 domain may be used for comparison, since this domain comprises the major part of the protein.

"Homologues" of a NAP1-like protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

The homologues useful in the method according to the invention have at least 50% sequence identity or similarity (functional identity) to the protein sequence as represented in SEQ ID NO: 2 (GenBank accession NP_177596), alternatively at least 60% or 70% sequence identity or similarity to SEQ ID NO:2. Typically, the homologues have at least 80% sequence identity or similarity, preferably at least 85% sequence identity or similarity, more preferably at least 90% sequence identity or similarity, most preferably at least 95%, 96%, 97%, 98% or 99% sequence identity or similarity to SEQ ID NO:2.

Alternatively, the homologues useful in the method according to the invention have at least 40% sequence identity or similarity (functional identity) to the protein sequence as represented in GenBank accession NP_568844 (SEQ ID NO: 29), alternatively at least 50%, 60% or 70% sequence identity or similarity to SEQ ID NO:29. Typically, the homologues have at least 80% sequence identity or similarity to SEQ ID NO:29, preferably at least 85% sequence identity or similarity, further preferably at least 90% sequence identity or similarity, most preferably at least 95%, 96%, 97%, 98% or 99% sequence identity or similarity to SEQ ID NO:29.

The percentage of identity may be calculated starting from full-length protein sequences or with certain (preferably conserved) regions of such a sequence, using alignment programs based on the Needleman and Wunsch algorithm (such as GAP), using the BLOSUM62 matrix, a gap opening penalty of 10 and a gap extension penalty of 0.5. For example the NAP domain as given in SEQ ID NO:32 may be used as query. The identification of such domains in a protein sequence would be well within the realm of the person skilled in the art and involve a computer readable format of the nucleic acids used in the methods of the present invention, the use of alignment software programs and the use of publicly available information on protein domains, conserved motifs and boxes. An integrated search may be done using the INTERPRO database (Mulder et al., (2003) Nucl. Acids Res. 31, 315-318, http://www.ebi.ac.uk/interpro/scan.html) which combines several databases on protein families, domains and functional sites, such as the PRODOM (Servant et al., (2002) Briefings in Bioinformatics 3, 246-251, http://prodes.toulouse.inra.fr/prodom/2002.1/html/home.php), PIR (Huang et al. (2003) Nucl. Acids Res. 31, 390-392, http://pir.georgetown.edu/) or Pfam (Bateman et al. (2002) Nucl. Acids Res. 30, 276-280, http://pfam.wustl.edu/) databases. Sequence analysis programs designed for motif searching may be used for identification of conserved fragments, regions and domains as mentioned above. Suitable computer programs include for example MEME (Bailey and Elkan (1994) Proceedings of the Second International Conference on Intelligent Systems for Molecular Biology, pp. 28-36, AAAI Press, Menlo Park, Calif., http://meme.sdsc.edu/meme/website/intro.html).

Homologous proteins may be grouped in "protein families". A protein family may be defined by functional and sequence similarity analysis, such as, for example, Clustal W. A neighbour-joining tree of the proteins homologous to NAP1-like may be generated by the Clustal W program and gives a good overview of its structural and ancestral relationship. In a particular embodiment of the present invention, the NAP1-like homologue(s) belong(s) to the same protein family as the protein corresponding to SEQ ID NO: 2.

In the *Arabidopsis* genome, two family members of the NAP1-like protein were identified (NM_177596 (SEQ ID NO: 2), NP_564063 (SEQ ID NO: 21)). Family members of the NAP1-like protein may also be identified in other plants such as rice or other monocotyledonous plants. Advantageously these family members are also useful in the methods of the present invention.

Two special forms of homology, orthologous and paralogous, are evolutionary concepts used to describe ancestral relationships of genes. The term "paralogous" relates to homologous genes that result from one or more gene duplications within the genome of a species. The term "orthologous" relates to homologous genes in different organisms due to ancestral relationship of these genes. The term "homologues" as used herein also encompasses paralogues and orthologues of the proteins useful in the methods according to the invention.

Orthologous genes may be identified by querying one or more gene databases with a query gene of interest, using for example the BLAST program. The highest-ranking subject genes that result from the search are then again subjected to a BLAST analysis, and only those subject genes that match again with the query gene are retained as true orthologous genes. For example, to find a rice orthologue of an *Arabidopsis thaliana* gene, one may perform a BLASTN or TBLASTX analysis on a rice database (such as (but not limited to) the *Oryza sativa* Nipponbare database available at the NCBI (http://www.ncbi.nlm.nih.gov) or the genomic sequences of rice (cultivars indica or japonica)). In a next step, the obtained rice sequences are used in a reverse BLAST analysis using an *Arabidopsis* database. The results may be further refined when the resulting sequences are analysed with ClustalW and visualised in a neighbour joining tree. This method may be used to identify orthologues from many different species.

"Homologues" of a NAP1-like encompass proteins having amino acid substitutions, insertions and/or deletions relative to the unmodified protein in question. "Substitutional variants" of a protein are those in which at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues, and deletions will range from about 1 to 20 residues. Preferably, amino acid substitutions comprise conservative amino acid substitutions. "Insertional variants" of a protein are those in which one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag·100 epitope, c-myc epitope, Flag®-epitope, lacZ, CMP (calmodulin-binding peptide), HA epitope, protein C epitope and VSV epitope. "Deletion variants" of a protein are characterised by the removal of one or more amino acids from the protein. Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The term "derivatives" of a NAP1-like protein refers to peptides, oligopeptides, polypeptides, proteins and enzymes which may comprise substitutions, deletions or additions of naturally and non-naturally occurring amino acid residues compared to the amino acid sequence of the naturally-occurring form of the NAP1-like protein (such as the protein presented in SEQ ID NO: 2). "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence such as, for example, a reporter molecule which is bound to facilitate its detection, and non-naturally occurring amino acid residues relative to the amino acid sequence of a naturally-occurring protein.

"Active fragments" of a NAP1-like protein encompasses at least the amount of amino acid residues, sufficient to retain similar biological and/or functional activity compared to the naturally occurring protein. A preferred active fragment of a NAP1-like protein comprises at least a NAP domain (Pfam 00956) and an acidic C-terminal domain enriched in D and/or E residues as described above, a more preferred active fragment furthermore comprises the conserved sequence of SEQ ID NO:33.

The term NAP1-like nucleic acid/gene, as defined herein, refers to any nucleic acid encoding a NAP1-like protein as defined above, or the complement thereof. The nucleic acid may be derived (either directly or indirectly (if subsequently modified)) from any source provided that the nucleic acid, when expressed in a plant, leads to modulated expression of a NAP-like nucleic acid/gene or modulated activity and/or levels of a NAP1-like protein. The nucleic acid may be isolated from a eukaryotic source, such as yeast or fungi, plants (including algae) or animals (including humans). This nucleic acid may be substantially modified from its native form in composition and/or genomic environment through deliberate human manipulation. The nucleic acid sequence is preferably a homologous nucleic acid sequence, i.e. a nucleic acid sequence encoding a protein structurally and/or functionally related to SEQ ID NO:2, preferably obtained from a plant, whether from the same plant species or different. Preferably, the nucleic acid is as represented by SEQ ID NO: 1 or a portion thereof or a nucleic acid sequence capable of hybridising therewith, which hybridising sequence encodes proteins having NAP1-like protein activity as described above; or it is a nucleic acid encoding an amino acid represented by SEQ ID NO: 2 or encoding a homologue, derivative or active fragment thereof. This term also encompasses variants of the nucleic acid encoding a NAP1-like protein due to the degeneracy of the genetic code; allelic variants; and different splice variants of the nucleic acid encoding a NAP1-like protein, including variants that are interrupted by one or more intervening sequences.

Advantageously, the method according to the present invention may also be practised using portions of a nucleic acid sequence encoding a NAP1-like protein as defined above, such as the NAP1-like protein encoded by SEQ ID NO: 1, or by using sequences that hybridise to a nucleic acid sequence encoding a NAP1-like protein as defined above, such as SEQ ID NO: 1, preferably under stringent conditions, (which hybridising sequences encode proteins having NAP1-like activity), or by using nucleic acids encoding homologues, derivatives or active fragments of a NAP1-like protein, such as the one represented by SEQ ID NO:2.

Portions of a DNA sequence refer to a piece of DNA derived or prepared from an original (larger) DNA molecule, which DNA portion, when expressed in a plant, gives rise to plants having improved growth characteristics. Preferably, the improved growth characteristics are increased yield, more preferably increased seed yield, most preferably the increased seed yield comprises one or more of increased harvest index, increased total weight of seeds and increased number of filled seeds. The portion may comprise many genes, with or without additional control elements, or may contain just spacer sequences etc.

The present invention also encompasses nucleic acid sequences capable of hybridising with a nucleic acid sequence encoding a NAP1-like protein, which nucleic acid sequences may also be useful in practising the methods according to the invention. The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process may also occur with one of the complementary nucleic acids immobilised to a matrix such as magnetic beads, Sepharose beads or any other resin. Tools in molecular biology relying on such a process include the isolation of poly (A$^+$) mRNA. The hybridisation process may furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and micro array hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition.

For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C.

High stringency conditions for hybridisation thus include high temperature and/or low salt concentration (salts include NaCl and $Na_3$-citrate) but may also be influenced by the inclusion of formamide in the hybridisation buffer and/or lowering the concentration of compounds such as SDS (sodium dodecyl sulphate) in the hybridisation buffer and/or exclusion of compounds such as dextran sulphate or polyethylene glycol (promoting molecular crowding) from the hybridisation buffer. Sufficiently low stringency hybridisation conditions are particularly preferred for the isolation of nucleic acids homologous to the DNA sequences useful in the methods of the invention defined supra. Elements contributing to homology include allelism, degeneration of the genetic code and differences in preferred codon usage. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ (temperature under defined ionic strength and pH, at which 50% of the target sequence hybridises to a perfectly matched probe) decreases about 1° C. per % base mismatch.

"Stringent hybridisation conditions" and "stringent hybridisation wash conditions" in the context of nucleic acid hybridisation experiments such as Southern and Northern hybridisations are sequence dependent and are different under different environmental parameters. For example, longer sequences hybridise specifically at higher temperatures. Specificity is typically the function of post-hybridisation washes. Critical factors of such washes include the ionic strength and temperature of the final wash solution.

Generally, stringent conditions are selected to be about 50° C. lower than the thermal melting point ($T_m$) for the specific sequence at a defined ionic strength and pH. The $T_m$ is dependent upon the solution conditions and the base composition of the probe, and may be calculated using the following equation:

$$T_m = 79.8° C. + (18.5 \times \log [Na^+]) + (58.4° C. \times \%[G+C]) - (820 \times (\#bp \text{ in duplex})^{-1}) - (0.5 \times \% \text{ formamide})$$

Alternative formula's, depending on the types of hybrids, are known in the art, for example:

DNA-DNA hybrids (Meinkoth and Wahl, Anal. Biochem., 138: 267-284, 1984):

$$T_m = 81.5° C. + 16.6 \times \log [Na^+]^a + 0.41 \times \%[G/C^b] - 500 \times [L^c]^{-1} - 0.61 \times \% \text{ formamide}$$

DNA-RNA or RNA-RNA hybrids:

$$T_m = 79.8 + 18.5(\log_{10} [Na^+]^a) + 0.58(\% G/C^b) + 11.8(\% G/C^b)^2 - 820/L^c$$

oligo-DNA or oligo-$RNA^d$ hybrids:

For <20 nucleotides: $T_m = 2(l_n)$

For 20-35 nucleotides: $T_m = 22 + 1.46 (l_n)$

[a] or for other monovalent cation, but only accurate in the 0.01-0.4 M range.

[b] only accurate for % GC in the 30% to 75% range.

[c] L=length of duplex in base pairs.

[d] Oligo, oligonucleotide; $l_n$, effective length of primer=2×(no. of G/C)+(no. of A/T).

Note: for each 1% formamide, the $T_m$ is reduced by about 0.6 to 0.7° C., while the presence of 6M urea reduces the $T_m$ by about 30° C.

More preferred stringent conditions are when the temperature is 20° C. below $T_m$, and the most preferred stringent conditions are when the temperature is 10° C. below $T_m$. Non-specific binding may also be controlled using any one of a number of known techniques such as, for example, blocking the membrane with protein containing solutions, additions of heterologous RNA, DNA, and SDS to the hybridisation buffer, and treatment with Rnase.

Wash conditions are typically performed at or below hybridisation stringency. Generally, suitable stringent conditions for nucleic acid hybridisation assays or gene amplification detection procedures are as set forth above. More or less stringent conditions may also be selected.

For the purposes of defining the level of stringency, reference can conveniently be made to Sambrook et al. (2001) Molecular Cloning: a laboratory manual, $3^{rd}$ Edition Cold Spring Harbor Laboratory Press, CSH, New York or to Current Protocols in Molecular Biology, John Wiley & Sons, N.Y. (1989). An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed such as medium stringent conditions. Examples of medium stringent conditions include 1-4×SSC/0.25% w/v SDS at ≧45° C. for 2-3 hours. An example of high stringency conditions includes 0.1-1×SSC/0.1% w/v SDS at 60° C. for 1-3 hours. The skilled artisan is aware of various parameters which may be altered during hybridisation and washing and which will either maintain or change the stringency conditions. For example, another stringent hybridisation condition is hybridisation at 4×SSC at 65° C., followed by a washing in 0.1×SSC, at 65° C. for about one hour. An alternative example of stringent hybridisation conditions is in 50% formamide, 4×SSC at 42° C. Still another example of stringent conditions include hybridisation at 62° C. in 6×SSC, 0.05× BLOTTO and washing at 2×SSC, 0.1% w/v SDS at 62° C.

The methods according to the present invention may also be practised using an alternative splice variant of a nucleic acid sequence encoding a NAP1-like protein. The term alternative splice variant as used herein encompasses variants of a nucleic acid sequence in which selected introns and/or exons have been excised, replaced or added. Such variants will be ones in which the biological activity of the protein remains unaffected, which can be achieved by selectively retaining functional segments of the protein. Such splice variants may be found in nature or can be manmade. Methods for making such splice variants are well known in the art. Therefore according to another aspect of the present invention, there is provided, a method for improving the growth characteristics of plants, comprising modulating expression in a plant of an alternative splice variant of a nucleic acid sequence encoding a NAP1-like protein and/or by modulating activity and/or levels of a NAP1-like protein encoded by the alternative splice variant. Preferably, the splice variant is a splice variant of the sequence represented by SEQ ID NO: 1. Preferably the improved growth characteristics are increased yield, more preferably increased seed yield, most preferably increased seed yield comprises increased harvest index, increased number of filled seeds and/or increased total weight of seeds.

Advantageously, the methods according to the present invention may also be practised using allelic variants of a nucleic acid sequence encoding a NAP1-like protein, preferably an allelic variant of a sequence represented by SEQ ID NO: 1. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest NAP1-like of sequence variants in naturally occurring polymorphic strains of most organisms. They are helpful in mapping genes and discovery of genes and gene functions. They are furthermore helpful in identification of genetic loci, e.g. plant genes, involved in determining processes such as growth rate, plant size and plant yield, plant vigor, disease resistance, stress tolerance etc.

The activity of a NAP1-like protein or a homologue thereof may also be modulated (increased or decreased) by introducing a genetic modification (preferably in the locus of a NAP1-like gene). The locus of a gene as defined herein is taken to mean a genomic region, which includes the gene of interest and 10 KB up- or downstream of the coding region. The term "genetic modification" refers to a change by human intervention in the genetic content of a cell compared to a wild type cell and includes techniques like genetic engineering, breeding or mutagenesis. The change in genetic content comprises modifications of the genome and includes addition, deletion and substitution of genetic material in the chromosomes of a plant cell as well as in episomes. The term also encompasses the addition of extrachromosomal information to a plant cell. Preferably, the genetic modification results in modulated expression of a NAP1-like nucleic acid, more preferably in increased expression of a NAP1-like nucleic acid.

The genetic modification may be introduced, for example, by any one (or more) of the following methods: TDNA activation, TILLING, site-directed mutagenesis, homologous recombination or by introducing and expressing in a plant cell a nucleic acid encoding a NAP1-like protein or a homologue thereof. Following introduction of the genetic modification, there follows a step of selecting for moduated activity of a NAP1-like protein. Preferably the modulated activity of a NAP1-like protein is increased activity, which increase in activity gives plants having improved growth characteristics such as increased seed yield. The selection step may be based on monitoring the presence or absence of improved growth characteristics, or on monitoring the presence or absence of selectable or screenable marker genes linked an introduced nucleic acid of interest.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a NAP-like gene using the technique of TILLING (Targeted Induced Local Lesions IN Genomes). This is a mutagenesis technology useful to generate and/or identify, and to eventually isolate mutagenised variants of a NAP1-like nucleic acid encoding a polypeptide capable of exhibiting NAP1-like activity. TILLING also allows selection of plants carrying such mutant variants. These mutant variants may even exhibit higher NAP1-like activity than that exhibited by the gene in its natural form. TILLING combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. 2000 April; 18(4):455-7, reviewed by Stemple 2004 (TILLING-a high-throughput harvest for functional genomics. Nat Rev Genet. 2004 February; 5(2):145-40.)).

Site-directed mutagenesis may be used to generate variants of NAP1-like nucleic acids or portions thereof. Several methods are available to achieve site-directed mutagenesis, the most common being PCR based methods (current protocols in molecular biology. Wiley Eds. http://www.4ulr.com/products/currentprotocols/index.html).

TDNA activation, TILLING and site-directed mutagenesis are examples of technologies that enable the generation of novel alleles and NAP1-like variants.

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. Extrachromosomal homologous recombination and gene targeting in plant cells after *Agrobacterium*-mediated transformation. 1990 EMBO J. 1990 October; 9(10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 April; 15(2):132-8). The nucleic acid to be targeted (which may be a NAP1-like nucleic acid or variant thereof as hereinbefore defined) need not be targeted to the locus of a NAP1-like gene, but may be introduced in, for example, regions of high expression. The nucleic acid to be targeted may be an improved allele used to replace the endogenous gene or may be introduced in addition to the endogenous gene.

NAP1-like proteins have a typical domain organisation, consisting of a NAP domain followed by an acidic C-terminal region. Therefore, it is envisaged that engineering of the domains of the NAP1-like protein in such a way that the activity of the NAP1-like protein is retained or modified, is useful for performing the methods of the invention. A preferred type of variants includes those generated by domain deletion, stacking or DNA shuffling (see for example He et al., Science 288, 2360-2363, 2000; or U.S. Pat. Nos. 5,811,238 and 6,395,547), provided that the resulting NAP1-like protein comprises a NAP domain and an acidic C-terminal region of 20 to 25 amino acids comprising at least 13 glutamic and/or aspartic acid residues. Directed evolution may also be used to generate variants of nucleic acids encoding a NAP1-like protein. This consists of iterations of DNA shuffling followed by appropriate screening and/or selection to generate variants of NAP1-like nucleic acids or portions thereof encoding NAP1-like polypeptides or homologues or portions thereof having an modified biological activity (Castle et al., (2004) Science 304(5674): 1151-4; U.S. Pat. Nos. 5,811,238 and 6,395,547).

Accordingly, as another aspect of the invention, there is provided a method for improving plant growth and development when compared to corresponding wild type plants, preferably for increasing plant yield, more preferably for increasing seed yield of a plant, comprising modulating expression, preferably increasing expression in a plant of a nucleic acid sequence encoding a NAP1-like protein and/or modulating activity and/or levels in a plant of a NAP1-like protein, preferably increasing activity and/or levels of a NAP1-like protein, wherein the nucleic acid sequence and the proteins include variants chosen from:
  (i) a nucleic acid encoding a NAP1-like protein, wherein the NAP1-like protein is preferably as represented by SEQ ID NO: 1 or encodes a NAP1-like protein as represented by SEQ ID NO: 2;
  (ii) an alternative splice variant of a nucleic acid sequence encoding a NAP1-like protein or wherein said NAP1-like protein is encoded by a splice variant;
  (iii) an allelic variant of a nucleic acid sequence encoding a NAP1-like protein or wherein said NAP1-like protein is encoded by an allelic variant;
  (iv) sequence capable of hybridising to a NAP1-like encoding nucleic acid, preferably under stringent conditions;
  (v) a NAP1-like protein
  (vi) a NAP1-like protein as represented by SEQ ID NO: 2
  (vii) homologues and derivatives of a NAP1-like protein, preferably of the NAP1-like protein presented in SEQ ID NO:2,
  and wherein said NAP1-like protein comprises a NAP domain and an acidic C-terminal, and has PP2a phosphatase inhibiting activity.

Preferably, the increased seed yield comprises one or more of increased harvest index, increased number of filled seeds and/or increased total weight of seeds.

In the methods of the present invention modulated expression, and in particular increased expression, of a nucleic acid is envisaged. Modulating expression (increasing or decreasing expression) of a nucleic acid encoding a NAP1-like protein or modulation of the activity and/or levels of the NAP1-like protein itself encompasses altered expression of a gene and/or altered activity and/or levels of a gene product, namely a polypeptide, in specific cells or tissues. Altered (increased or decreased) expression of a gene and/or altered (increased or decreased) activity and/or levels of a gene product may be effected, for example by chemical means and/or recombinant means. Modulating expression of a gene and/or levels of a gene product and/or modulating activity of a gene product may be effected directly through the modulation of expression of a NAP1-like-encoding gene and/or directly through the modulation of the activity and/or levels of a NAP1-like protein. The modulated expression may result from altered expression levels of an endogenous NAP1-like gene and/or may result from modulated expression of a NAP1-like encoding nucleic acid that was previously introduced in a plant. Similarly, modulated levels and/or activity of a NAP1-like protein may be the result of altered expression levels of an endogenous NAP1-like gene and/or may result from altered expression of a NAP1-like encoding nucleic acid that was previously introduced into a plant. Additionally or alternatively, the modulation of expression as mentioned above is effected in an indirect way, for example it may be effected as a result of decreased or increased levels and/or activity of factors that control the expression of a NAP1-like gene or that influence the activity and/or levels of the NAP1-like protein.

According to a preferred embodiment of the present invention, modulation of expression of a nucleic acid encoding a NAP1-like protein and/or modulation of activity and/or levels of the NAP1-like protein itself is effected by recombinant means. Such recombinant means may comprise a direct and/or indirect approach for modulation of expression of a nucleic acid and/or for modulation of the activity and/or levels of a protein.

A direct and preferred approach for modulating expression of a NAP1-like gene or modulating the activity and/or levels of a NAP1-like protein, comprises introducing into a plant an isolated nucleic acid sequence encoding a NAP1-like protein or a homologue, derivative or active fragment thereof. The nucleic acid may be introduced into a plant by, for example, transformation. Therefore, according to a preferred aspect of the present invention, there is provided a method for improving growth and development of a plant, in particular for increasing yield of a plant comprising a genetic modification of the plant, which genetic modification comprises introducing a NAP1-like encoding nucleic acid into a plant. Preferably the increased plant yield is increased seed yield, more preferably comprises one or more of increased harvest index, increased number of filled seeds or increased total weight of seeds.

According to a preferred aspect of the present invention, enhanced or increased expression of a nucleic acid is envisaged. Methods for obtaining enhanced or increased expression of genes or gene products are well documented in the art and include, for example, overexpression driven by a suitable (preferably strong) promoter, the use of transcription enhancers or translation enhancers. The term overexpression as used herein means any form of expression that is additional to the original wild-type expression level. Preferably the nucleic acid to be introduced into the plant and/or the nucleic acid that is to be overexpressed in the plants is in sense direction with respect to the promoter to which it is operably linked. Preferably, the nucleic acid to be overexpressed encodes a NAP1-like protein, further preferably the nucleic acid sequence encoding the NAP1-like protein is isolated from a dicotyledonous plant, preferably of the family Brassicaceae, further preferably the sequence is isolated from *Arabidopsis thaliana*, most preferably the nucleic acid sequence is as represented by SEQ ID NO: 1 or a portion thereof, or encodes an amino acid sequence as represented by SEQ ID NO: 2 or a homologue, derivative or active fragment thereof. Alternatively, the nucleic acid sequence encoding the NAP1-like protein is as represented in SEQ ID NO: 20 (GenBank Accession Number NM_101738) or is a portion thereof, or encodes an amino acid sequence as represented in SEQ ID NO: 21 (GenBank Accession Number NP-564063) or encodes a homologue, derivative or active fragment thereof. It should be noted that the applicability of the invention does not rest upon the use of the nucleic acid represented by SEQ ID NO: 1, nor upon the nucleic acid sequence encoding the amino acid sequence of SEQ ID NO: 2, but that other nucleic acid sequences encoding homologues, derivatives or active fragments of SEQ ID NO: 2, or portions of SEQ ID NO: 1, or sequences hybridising with SEQ ID NO: 1 may be used in the methods of the present invention. In particular, homologues from other species such as tobacco (SEQ ID NO: 7 or 9), maize (SEQ ID NO: 13 or 19), *Medicago sativa* (SEQ ID NO: 11), tomato (SEQ ID NO: 23) or rice (SEQ ID NO: 15 or 17) are also useful in the methods of the present invention.

The present invention relates to methods to improve growth characteristics of a plant or to methods to produce plants with improved growth characteristics, wherein the growth characteristics include increased yield, comprising any one or more of: increased number of tillers, increased number of first panicles (being the tallest panicle and all the panicles that overlap with the tallest panicle when aligned vertically), increased number of second panicles, increased total number of seeds, increased number of filled seeds, increased total seed weight per plant, increased harvest index, increased thousand kernel weight. The present invention also provides methods to improve one of the above mentioned growth characteristics, without causing a penalty on one of the other growth characteristics, for example increase of the number of filled seeds while retaining the same number of spikelets per panicle.

The term "increased yield" encompasses an increase in biomass in one or more parts of a plant relative to the corresponding part(s) of wild-type plants. The term encompasses an increase in seed yield, which includes an increase in the biomass of the seed (seed weight) and/or an increase in the number of (filled) seeds and/or in the size of the seeds and/or an increase in seed volume, each relative to corresponding wild-type plants. Depending on the crop, the plant parts in question may be above-ground biomass (e.g. corn, when used as silage, sugarcane), roots (e.g. sugar beet), fruit (e.g. tomato), cotton fibres, or any other part of the plant which is of economic value. Taking rice as an example, a yield increase may be manifested by an increase in one or more of the following: number of panicles per plant, number of spikelets per panicle, number of flowers per panicle, increase in the seed filling rate, increase in thousand kernel weight, among others. For maize, the increase of seed yield may be reflected in for example an increase of rows (of seeds) per ear and/or an increased number of kernels per row. An increase in seed size and/or volume may also influence the composition of seeds. An increase in seed yield could be due to an increase in the number and/or size of flowers. An increase in yield might also increase the harvest index, which is expressed as a ratio of the yield of harvestable parts, such as seeds, over the total biomass; or thousand kernel weight. Increased yield also encompasses the capacity for planting at higher density (number of plants per hectare or acre).

Also modified cell division may contribute to yield increase. The term "modified cell division" encompasses an increase or decrease in cell division or an abnormal cell division/cytokinesis, altered plane of division, altered cell polarity, altered cell differentiation. The term also comprises phenomena such as endomitosis, acytokinesis, polyploidy, polyteny and endoreduplication.

It can be envisaged that plants having increased yield also exhibit a modified growth rate when compared to corresponding wild-type plants. The term "modified growth rate" as used herein encompasses, but is not limited to, a faster rate of growth in one or more parts of a plant (including seeds), at one or more stages in the life cycle of a plant. Plants with improved growth may show a modified growth curve and may have modified values for their $T_{mid}$ or $T_{90}$ (respectively the time needed to reach half of their maximal size or 90% of their maximal size, each relative to corresponding wild-type plants). The term "improved growth" encompasses enhanced vigour, earlier flowering, modified cycling time.

According to a preferred feature of the present invention, performance of the methods according to the present invention results in plants having increased yield, in particular plants having increased seed yield. Preferably, the increased seed yield includes at least an increase in any one or more of number of filled seeds, total seed weight, and harvest index, each relative to control plants. Therefore, according to the present invention, there is provided a method for increasing yield of plants, which method comprises modulating expression of a nucleic acid sequence encoding a NAP1-like protein and/or modulating activity of the NAP1-like protein itself in a plant, preferably wherein the NAP1-like protein is encoded by a nucleic acid sequence represented by SEQ ID NO: 1 or a portion thereof or by sequences capable of hybridising therewith or wherein the NAP1-like protein is represented by SEQ ID NO: 2 or is a homologue, derivative or active fragment thereof. Alternatively, the NAP1-like protein may be encoded by nucleic acid sequences as represented in SEQ ID NO: 20 (GenBank Accession Number NM_101738), SEQ ID NO: 6, 8, 10, 12, 14, 16, 18 or 22, or by a portion thereof or by sequences capable of hybridising therewith, or the NAP1-like protein may be as represented in SEQ ID NO: 21 (GenBank Accession Number NP_564063), SEQ ID NO: 7, 9, 11, 13, 15, 17, 19, 23 or may be a homologue, derivative or active fragment of any thereof.

The methods of the present invention are favourable to apply to crop plants because the methods of the present invention are used to increase one or more of the total seed weight, number of filled seeds and harvest index of a plant. Therefore, the methods of the present invention are particularly useful for crop plants cultivated for their seeds, such as cereals, sunflower, soybean, pea, flax, lupines, canola. Accordingly, a particular embodiment of the present invention relates to a method to increase seed yield (increased total seed weight, increased number of filled seeds and/or to increase harvest index) of a cereal.

According to a further embodiment of the present invention, genetic constructs and vectors to facilitate introduction and/or expression of the nucleotide sequences useful in the methods according to the invention are provided. Therefore, according to a second embodiment of the present invention, there is provided a gene construct for expression in a plant, comprising:

(i) a nucleic acid sequence encoding a NAP1-like protein;
(ii) one or more control sequences capable of driving expression in a plant of the nucleic acid sequence of (i); and optionally
(iii) a transcription termination sequence.

Constructs useful in the methods according to the present invention may be created using recombinant DNA technology well known to persons skilled in the art. The gene constructs may be inserted into vectors, which may be commercially available, suitable for transforming into plants and suitable for expression of the gene of interest in the transformed cells. The genetic construct may be an expression vector wherein the nucleic acid sequence is operably linked to one or more control sequences allowing expression in prokaryotic and/or eukaryotic host cells.

According to a preferred embodiment of the invention, the genetic construct is an expression vector designed to overexpress the nucleic acid sequence. The nucleic acid sequence capable of modulating expression of a nucleic acid encoding a NAP1-like protein and/or activity of the NAP1-like protein itself may be a nucleic acid sequence encoding a NAP1-like protein or a homologue, derivative or active fragment thereof, such as any of the nucleic acid sequences described hereinbefore. A preferred nucleic acid sequence is the sequence represented by SEQ ID NO: 1 or a portion thereof or sequences capable of hybridising therewith or a nucleic acid sequence encoding a protein represented by SEQ ID NO: 2 or a homologue, derivative or active fragment thereof. Preferably, this nucleic acid is cloned in sense orientation relative to the control sequence to which it is operably linked.

Plants are transformed with a vector comprising the sequence of interest (i.e., the nucleic acid sequence capable of modulating expression of nucleic acid encoding a NAP1-like protein), which sequence is operably linked to one or more control sequences (at least a promoter). The terms "regulatory element", "control sequence" and "promoter" are all used herein interchangeably and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence depending on the desired outcome. Preferably, the nucleic acid sequence encoding a NAP1-like protein is operably linked to a constitutive promoter. The term "constitutive" as defined herein refers to a promoter that is expressed predominantly in at least one tissue or organ and predominantly at any life stage of the plant. Preferably the promoter is expressed predominantly throughout the plant. Preferably, the constitutive promoter is the GOS2 promoter from rice, or a promoter of similar strength and/or a promoter with a similar expression pattern. Alternatively, tissue specific promoters may be used. For example, in cases where increased seed yield is envisaged, the use of seed preferred, flower preferred, meristem preferred promoters or promoters active in dividing cells can be contemplated. Promoter strength and/or expression pattern may be analysed for example by coupling the promoter to a reporter gene and assay the expression of the reporter gene in various tissues of the plant. One suitable reporter gene well known to a person skilled in the art is beta-glucuronidase.

Examples of alternative promoters with their respective expression pattern are presented in Table 2, and these promoters or derivatives thereof may be useful for the methods of the present invention.

TABLE 2

Examples of promoters for use in the performance of the present invention

| Gene source | Expresssion pattern | Reference |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| rice cyclophilin | constitutive | Buchholz et al, Plant Mol Biol. 25(5): 837-43, 1994 |
| maize H3 histone | constitutive | Lepetit et al, Mol. Gen. Genet. 231: 276-285, 1992 |
| actin 2 | constitutive | An et al, Plant J. 10(1); 107-121, 1996 |
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al Plant Mol Biol, 14(3): 323-32 1990 |
| napA | seed | Stalberg, et al, Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley ltr1 promoter | endosperm | |

TABLE 2-continued

Examples of promoters for use in the performance of the present invention

| Gene source | Expresssion pattern | Reference |
|---|---|---|
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| AtPRP4 | flowers | http://salus.medium.edu/mmg/tierney/html |
| chalcone synthase (chsA) | flowers | Van der Meer, et al., Plant Mol. Biol. 15, 95-109, 1990. |
| LEAFY | shoot meristem | Weigel et al., Cell 69: 843-859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| Tobacco (*N. sylvestris*) cyclin B1; 1 | Dividing cells/ meristematic tissue | Trehin et al. 1997 Plant Mol. Biol. 35, 667-672. |
| *Catharanthus roseus* Mitotic cyclins CYS (A-type) and CYM (B-type) | Dividing cells/ meristematic tissue | Ito et al. 1997 Plant J. 11, 983-992 |
| *Arabidopsis* cyc1At (=cyc B1; 1) and cyc3aAt (A-type) | Dividing cells/ meristematic tissue | Shaul et al. 1996 Proc. Natl. Acad. Sci. U.S.A 93, 4868-4872. |
| *Arabidopsis* tef1 promoter box | Dividing cells/ meristematic tissue | Regad et al. 1995 Mol. Gen. Genet. 248, 703-711. |
| *Catharanthus roseus* cyc07 | Dividing cells/ meristematic tissue | Ito et al. 1994 Plant Mol. Biol. 24, 863-878. |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

In a preferred embodiment, the genetic construct as mentioned above, comprises a NAP1-like gene in sense orientation coupled to a promoter that is preferably a constitutive promoter, such as the rice GOS2 promoter. Therefore, another aspect of the present invention is a vector construct carrying an expression cassette essentially similar to SEQ ID NO: 3, comprising the rice GOS2 promoter, the *Arabidopsis* NAP1-like gene and the T-zein+T-rubisco deltaGA transcription terminator sequence. A sequence essentially similar to SEQ ID NO: 3 encompasses a nucleic acid encoding a protein homologous to SEQ ID NO: 2 or hybridising to SEQ ID NO: 1, which nucleic acid is operably linked to a rice GOS2 promoter or a promoter with a similar expression pattern and/or which nucleic acid is linked to a transcription termination sequence.

Therefore according to another aspect of the invention, there is provided a gene construct, comprising an expression cassette in which is located a nucleic acid sequence encoding an NAP1-like protein, chosen from the group comprising:
  (i) a nucleic acid sequence represented by SEQ ID NO: 1 or the complement strand thereof;
  (ii) a nucleic acid sequence encoding an amino acid sequence represented by SEQ ID NO: 2 or homologues, derivatives or active fragments thereof;
  (iii) a nucleic acid sequence capable of hybridising (preferably under stringent conditions) with a nucleic acid sequence of (i) or (ii) above, which hybridising sequence preferably encodes a protein having NAP1-like protein activity;
  (iv) a nucleic acid sequence according to (i) to (iii) above which is degenerate as a results of the genetic code;
  (v) nucleic acid sequence which is an allelic variant to the nucleic acid sequences according to (i) to (iii);
  (vi) nucleic acid sequence which is an alternative splice variant to the nucleic acid sequences according to (i) to (iii);

The present invention also encompasses plants obtainable by the methods according to the present invention. The present invention therefore provides plants obtainable by the methods of the present invention, which plants have increased yield and which plants have modulated NAP1-like protein activity and/or levels and/or modulated expression of a nucleic acid encoding a NAP1-like protein. Preferably, the plants are transgenic plants comprising an isolated nucleic acid sequence encoding a NAP1-like protein, characterized in that the transgenic plant has been selected for having increased yield. Further preferably, the transgenic plant has been selected for modulated expression of a nucleic acid encoding a NAP1-like protein. Furthermore preferably, the transgenic plant has been selected for modulated expression of a nucleic acid encoding a NAP1-like protein as represented by SEQ ID NO:2

According to a third embodiment of the present invention, there is provided a method for the production of transgenic plants having improved growth characteristics, comprising introduction and expression in a plant of a nucleic acid encoding a NAP1-like protein as described above. Preferably, the improved growth characteristics comprise increased yield, more preferably increased seed yield, most preferably comprising one or more of increased number of filled seeds, increased harvest index or increased total weight of seeds.

More specifically, the present invention provides a method for the production of transgenic plants having increased yield, which method comprises:
  (i) introducing into a plant cell a nucleic acid sequence encoding a NAP1-like protein;
  (ii) regenerating and/or growing a plant from a transgenic plant cell.

The NAP1-like protein itself and/or the NAP1-like nucleic acid itself may be introduced directly into a plant cell or into the plant itself (including introduction into a tissue, organ or any other part of the plant). According to a preferred feature of the present invention, the nucleic acid is preferably introduced into a plant by transformation. The nucleic acid is preferably as represented by SEQ ID NO: 1 or a portion thereof or sequences capable of hybridising therewith, or is a nucleic acid encoding an amino acid sequence represented by SEQ ID NO: 2 or a homologue, derivative or active fragment thereof. Alternatively, the nucleic acid sequence is as represented in SEQ ID NO: 20 (GenBank Accession Number NM__101738), SEQ ID NO: 6, 8, 10, 12, 14, 16, 18, 22 or a portion thereof or sequences capable of hybridising with any of the aforementioned sequences. The amino acid sequence may alternatively be a sequence as represented in SEQ ID NO: 21 (GenBank Accession Number NP__564063), SEQ ID NO: 7, 9, 11, 13, 15, 17, 19, 23 or homologues, derivatives or active fragments thereof.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell can then be used to regenerate a transformed plant in a manner known to persons skilled in the art.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing an NAP1-like gene are preferably produced via *Agrobacterium*-mediated transformation using any of the well known methods for rice transformation, such as described in any of the following: European patent application EP 1198985 A1, Aldemita and Hodges (Planta, 199, 612-617, 1996); Chan et al. (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated nucleic acid molecule encoding a protein capable of modulating levels and/or activity of a NAP1-like protein, preferably wherein the protein is a NAP1-like protein. Preferred host cells according to the invention are plant cells. Therefore, the invention also encompasses host cells or transgenic plants having altered growth characteristics, characterized in that the host cell or transgenic plant has modulated expression of a nucleic acid sequence encoding a NAP1-like protein and/or modulated activity and/or level of a NAP1-like protein. Preferably, the altered growth characteristics comprise increased yield, more preferably increased seed yield.

The invention also extends to harvestable parts of a plant such as, but not limited to, seeds, leaves, fruits, flowers, stems or stem cultures, rhizomes, roots, tubers and bulbs. The invention furthermore relates to products directly derived from a harvestable part of such a plant, such as dry pellets or powders, oil, fat and fatty acids, starch or proteins.

The term "plant" as used herein encompasses whole plants, ancestors and progeny of the plants and plant parts, plant cells, tissues and organs. The term "plant" also therefore encompasses suspension cultures, embryos, meristematic regions, callus tissue, leaves, flowers, fruits, seeds, roots (including rhizomes and tubers), shoots, bulbs, stems, gametophytes, sporophytes, pollen, and microspores. Plants that are particularly useful in the methods of the invention include algae, ferns, and all plants which belong to the superfamily Viridiplantae, in particular monocotyledonous and dicotyledonous plants, including fodder or forage legumes, ornamental plants, food crops, trees, or shrubs selected from the list comprising *Abelmoschus* spp., *Acer* spp., *Actinidia* spp., *Agropyron* spp., *Allium* spp., *Amaranthus* spp., *Ananas comosus*, *Annona* spp., *Apium graveolens*, *Arabidopsis thaliana*, *Arachis* spp., *Artocarpus* spp., *Asparagus officinalis*, *Avena sativa*, *Averrhoa carambola*, *Benincasa hispida*, *Bertholletia excelsea*, *Beta vulgaris*, *Brassica* spp., *Cadaba farinosa*, *Camellia sinensis*, *Canna indica*, *Capsicum* spp., *Carica papaya*, *Carissa macrocarpa*, *Carthamus tinctorius*, *Carya* spp., *Castanea* spp., *Cichorium endivia*, *Cinnamomum* spp., *Citrullus lanatus*, *Citrus* spp., *Cocos* spp., *Coffea* spp., *Cola* spp., *Colocasia esculenta*, *Corylus* spp., *Crataegus* spp., *Cucumis* spp., *Cucurbita* spp., *Cynara* spp., *Daucus carota*, *Desmodium* spp., *Dimocarpus longan*, *Dioscorea* spp., *Diospyros* spp., *Echinochloa* spp., *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp., *Gossypium hirsutum*, *Heianthus* spp., *Hibiscus* spp., *Hordeum* spp., *Ipomoea batatas*, *Juglans* spp., *Lactuca sativa*, *Lathyrus* spp., *Lemna* spp., *Lens culinaris*, *Linum usitatissimum*, *Litchi chinensis*, *Lotus* spp., *Luffa acutangula*, *Lupinus* spp., *Macrotyloma* spp., *Malpighia emarginata*, *Malus* spp., *Mammea americana*, *Mangifera indica*, *Manihot* spp., *Manilkara zapota*, *Medicago sativa*, *Melilotus* spp., *Mentha* spp., *Momordica* spp., *Morus nigra*, *Musa* spp., *Nicotiana* spp., *Olea* spp., *Opuntia* spp., *Ornithopus* spp., *Oryza* spp., *Panicum miliaceum*, *Passiflora edulis*, *Pastinaca sativa*, *Persea* spp., *Pefroselinum crispum*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Rubus* spp., *Saccharum* spp., *Sambucus* spp., *Secale cereale*, *Sesamum* spp., *Solanum* spp., *Sorghum bicolor*, *Spinacia* spp., *Syzygium* spp., *Tamarindus indica*, *Theobroma cacao*, *Trifolium* spp., *Triticosecale rimpaui*, *Triticum* spp., *Vaccinium* spp., *Vicia* spp., *Vigna* spp., *Vitis* spp., *Zea mays*, *Zizania palustris*, *Ziziphus* spp., amongst others.

According to a preferred feature of the present invention, the plant is a crop plant comprising soybean, sunflower, canola, alfalfa, rapeseed or cotton. Further preferably, the plant according to the present invention is a monocotyledonous plant such as sugarcane, most preferably a cereal, such as rice, maize, wheat, millet, barley, oats, sorghum.

The present invention also encompasses the use of nucleic acids encoding a NAP1-like protein, portions or variants thereof and the use of NAP1-like polypeptides, homologues or derivatives thereof.

One such use relates to improving the growth characteristics of plants, in particular in improving yield, especially seed yield. The seed yield may include one or more of the following: increased number of seeds, increased number of filled seeds, increased total seed weight, increased harvest index, increased thousand kernel weight, seed filling rate, among others. Preferably, the NAP1-like protein or the nucleic acid encoding a NAP1-like protein is of plant origin, more preferably from a dicotyledonous plant, furthermore preferably from the family of Brassicaceae, most preferably, the NAP1-like protein is encoded by SEQ ID NO:1 or is as represented by SEQ ID NO:2.

NAP1-like nucleic acids or variants thereof or NAP1-like polypeptides or homologues thereof may find use in breeding programmes in which a DNA marker is identified that may be genetically linked to a NAP1-like gene or variant thereof. The NAP1-like gene or variants thereof or NAP1-like protein or homologues thereof may be used to define a molecular marker. This DNA or protein marker may then be used in breeding programmes to select plants having improved growth characteristics. The NAP1-like gene or variant thereof may, for example, be a nucleic acid as represented by SEQ ID NO: 1, or a nucleic acid encoding any of the above mentioned homologues.

Allelic variants of a gene encoding a NAP1-like protein may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give rise to improved growth characteristics in a plant, such as increased seed yield. Selection is typically carried out by monitoring growth performance of plants containing different allelic variants of the sequence in question, for example, different allelic variants of SEQ ID NO: 1, or of nucleic acids encoding any of the above mentioned plant homologues. Growth performance may be monitored in a greenhouse or in the field. Further optional steps include crossing plants, in which the superior allelic variant resulting in increased seed yield was identified, with another plant. This could be used, for example, to make a combination of interesting phenotypic features.

A NAP1-like nucleic acid or variant thereof may also be used as probes for genetically and physically mapping the genes that they are a part of, and as markers for traits linked to those genes. Such information may be useful in plant breeding in order to develop lines with desired phenotypes. Such use of NAP1-like nucleic acids or variants thereof requires only a nucleic acid sequence of at least 10 nucleotides in length. The NAP1-like nucleic acids or variants thereof may be used as restriction fragment length polymorphism (RFLP) markers. Southern blots of restriction-digested plant genomic DNA may be probed with the NAP1-like nucleic acids or variants thereof. The resulting banding patterns may then be subjected to genetic analyses using computer programs such as MapMaker (Lander et al. (1987) Genomics 1, 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the NAP1-like nucleic acid or variant thereof in the genetic map previously obtained using this population (Botstein et al. (1980) Am. J. Hum. Genet. 32, 314-331).

The production and use of plant gene-derived probes for use in genetic mapping is described in Bematzky and Tanksley (Plant Mol. Biol. Reporter 4, 37-41, 1986). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Nonmammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7, 149-154). Although current methods of FISH mapping favour use of large clones (several to several hundred kb; see Laan et al. (1995) Genome Res. 5, 13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med. 11, 95-96), polymorphism of PCR-amplified fragments (CAPS; Sheffield et al. (1993) Genomics 16, 325-332), allele-specific ligation (Landegren et al. (1988) Science 241, 1077-1080), nucleotide extension reactions (Sokolov (1990) Nucleic Acid Res. 18, 3671), Radiation Hybrid Mapping (Walter et al. (1997) Nat. Genet. 7, 22-28) and Happy Mapping (Dear and Cook (1989) Nucleic Acid Res. 17, 6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In this way, generation, identification and/or isolation of modified plants with altered NAP1-like activity displaying improved growth characteristics can be performed.

NAP1-like nucleic acids or variants thereof or NAP1-like polypeptides or homologues thereof may also find use as growth regulators. Since these molecules have been shown to be useful in improving the growth characteristics of plants, they would also be useful growth regulators, such as herbicides or growth stimulators. The present invention therefore provides a composition comprising a NAP1-like nucleic acid or variant thereof or a NAP1-like polypeptide or homologue thereof, together with a suitable carrier, diluent or excipient, for use as a growth regulator, preferably as a growth promoter, more preferably for increasing yield.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features. Accordingly, the methods of the present invention may also be used in so-called "gene stacking" procedures.

DESCRIPTION OF FIGURES

The present invention will now be described with reference to the following figures in which:

FIG. 5 Alignment of the *Arabidopsis thaliana* NAP-like protein (AtNAP1-like) and the *Medicago sativa* NAP1-like protein (MsNAP-like) using the Needleman and Wunsch algorithm. The gap opening penalty was set on 10, the gap extension penalty was 0.5. With these settings, the sequence identity was 71.2% and sequence homology 84.5%.

FIG. 6 The NAP1-like protein has a nuclear localisation in plants. A) The *Medicago* NAP1-like protein has been shown to be localised in the nucleus of cultured alfalfa cells by indirect immunofluorescence using an antibody raised against the purified protein (left picture of panel A). To confirm the nuclear localisation, the nuclei were stained in parallel with the fluorescent dye DAPI, (right picture of panel A). In the insert the arrow points to a metaphase cell. A faint fluorescence indicates low abundance of the NAP1-like protein around the chromosomes in metaphase cells without a nuclear compartment. B) The transiently expressed *Arabidopsis* NAP1-like protein, fused to GFP, is localised to the nucleus in *Arabidopsis* cells following a PEG-mediated uptake of the gene construct into protoplasts.

FIG. 8 Examples of sequences useful in performing the methods according to the present invention.

EXAMPLES

The present invention will now be described with reference to the following examples, which are by way of illustration alone.

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (Current Protocols in Molecular Biology. New York: John Wiley and Sons, 1998). Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

Figure 1:
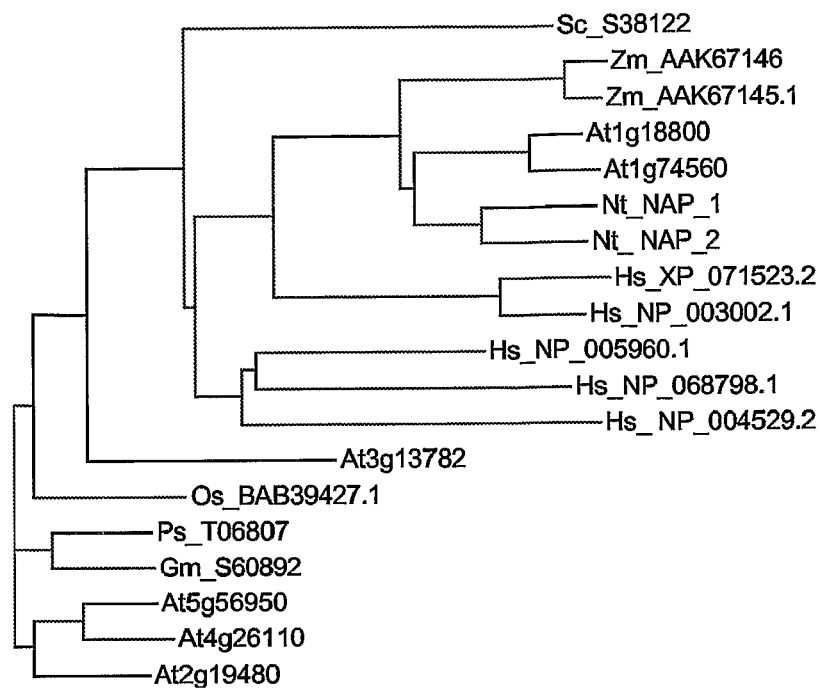
FIG. 1 Phylogenetic tree representing the relationships among NAP and SET proteins from yeast, man and plants. The tree was established by the AlignX program of VNTI Suite 5.5 (Informax, http://www.informaxinc.com/). The matrix used to generate the multiple alignment is Blosum62 and the alignment parameters used were: Gap Opening penalty, 10; Gap Extension penalty, 0.5; Gap separation penalty range, 8; % identity for alignment delay, 40. The Phylogenetic tree is built using the Neighbor Joining method of Saitou and Nei. GenBank and MIPS (for *Arabidopsis thaliana*) accession numbers of the sequences used in the alignment are indicated in the tree. At: *Arabidopsis thaliana*, Gm: *Glycine max*, Nt: *Nicotiana tabacum* (sequences derived from WO 03/085115), Os: *Oryza sativa*, Ps: *Pisum sativum*, Zm: *Zea mays*, Hs: *Homo sapiens*, Sc: *Saccharomyces cerevisiae*.
Figure 2:
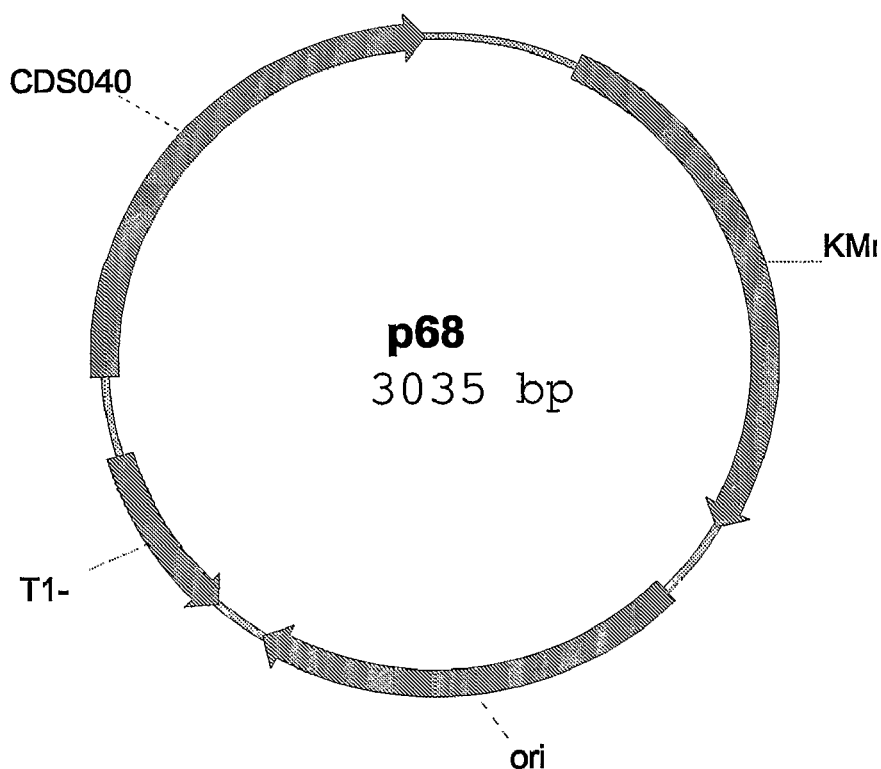
FIG. 2 Schematic presentation of the entry clone p68, containing CDS0406 within the AttL1 and AttL2 sites for Gateway® cloning in the pDONR201 backbone. CDS0406 is the internal code for the *Arabidopsis* NAP1-like coding sequence. This vector contains also a bacterial kanamycine-resistance cassette and a bacterial origin of replication.

The *Arabidopsis* NAP1-like (internal reference CDS0406) was amplified by PCR using as template an Arabidopsis thaliana seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of $1.59 \times 10^7$ cfu. Original titer was determined to be $9.6 \times 10^5$ cfu/ml, after first amplification of $6 \times 10^{11}$ cfu/ml. After plasmid extraction, 200 ng of template was used in a 50 µl PCR mix. Primers prm1505 (SEQ ID NO: 4) and prm1506 (SEQ ID NO: 5), which include the AttB sites for Gateway recombination, were used for PCR amplification. PCR was performed using Hifi Taq DNA polymerase in standard conditions. A PCR fragment of 771 bp was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p68 (FIG. 2). Plasmid pDONR201 was purchased from Invitrogen, as part of the Gateways technology.

Example 2

Vector Construction

Figure 3:
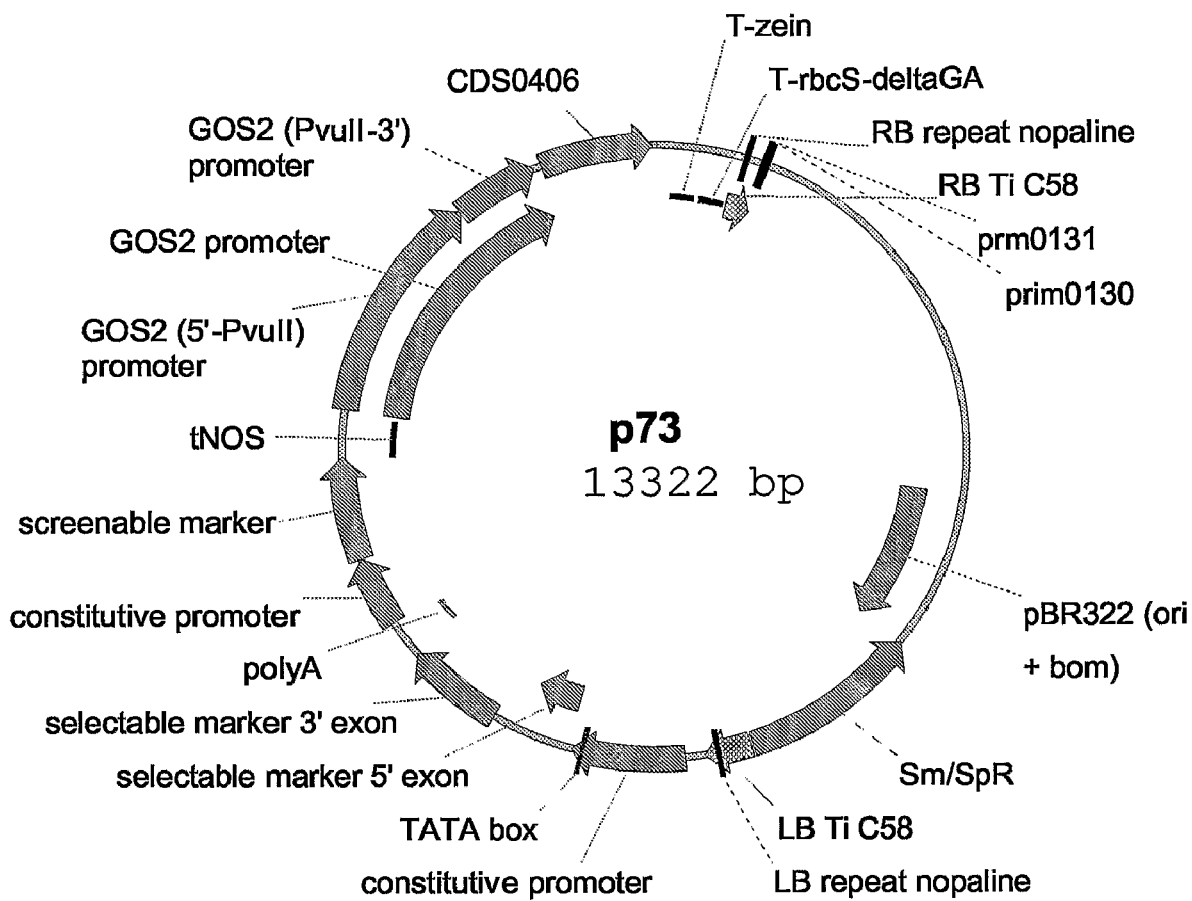
FIG. 3 Binary vector for the expression in *Oryza sativa* of the *Arabidopsis* NAP1-like gene (CDS0406) under the control of the Gos2 promoter (PRO0129). This vector contains a T-DNA derived from the Ti Plasmid, limited by a left border (LB repeat, LB Ti C58) and a right border (RB repeat, RB Ti C58)). From the left border to the right border, this T-DNA contains: a cassette for antibiotic selection of transformed plants; a selectable marker cassette for visual screening of transformed plants and the PRO0129-CDS0406-zein and rbcS-deltaGA double terminator cassette for expression of the *Arabidopsis* NAP1-like gene. This vector also contains an origin of replication from pBR322 for bacterial replication and a selectable marker (Spe/SmeR) for bacterial selection with spectinomycin and streptomycin.

The entry clone p68 was subsequently used in an LR reaction with p0640, a destination vector used for *Oryza sativa* transformation. This vector contains as functional elements within the T-DNA borders: a plant selectable marker; a visual marker expression cassette; and a Gateway cassette intended for LR in vivo recombination with the sequence of interest already cloned in the entry clone. A GOS2 promoter for constitutive expression (PRO0129) is located upstream of this Gateway cassette. After the LR recombination step, the resulting expression vector p73 (FIG. 3) can be transformed into the *Agrobacterium* strain LBA4404 and subsequently to *Oryza sativa* plants.

Example 3

Rice Transformation

Mature dry seeds of *Oryza sativa* japonica cultivar Nipponbare were dehusked. Sterilization was done by incubating the seeds for one minute in 70% ethanol, followed by 30 minutes in 0.2% $HgCl_2$ and by 6 washes of 15 minutes with sterile distilled water. The sterile seeds were then germinated on a medium containing 2,4-D (callus induction medium). After a 4-week incubation in the dark, embryogenic, scutellum-derived calli were excised and propagated on the same medium. Two weeks later, the calli were multiplied or propagated by subculture on the same medium for another 2 weeks. 3 days before co-cultivation, embryogenic callus pieces were sub-cultured on fresh medium to boost cell division activity. The *Agrobacterium* strain LBA4404 harbouring the binary vector p73 was used for co-cultivation. The *Agrobacterium* strain was cultured for 3 days at 28° C. on AB medium with the appropriate antibiotics. The bacteria were then collected and suspended in liquid co-cultivation medium at an $OD_{600}$ of about 1. The suspension was transferred to a petri dish and the calli were immersed in the suspension during 15 minutes. Next, the callus tissues were blotted dry on a filter paper, transferred to solidified co-cultivation medium and incubated for 3 days in the dark at 25° C. Thereafter, co-cultivated callus was grown on 2,4-D-containing medium for 4 weeks in the dark at 28° C. in the presence of a selective agent at a suitable concentration. During this period, rapidly growing resistant callus islands developed. Upon transfer of this material to a regeneration medium and incubation in the light, the embryogenic potential was released and shoots developed in the next four to five weeks. Shoots were excised from the callus and incubated for 2 to 3 weeks on an auxin-containing medium from which they were transferred to soil. Hardened shoots were grown under high humidity and short days in a greenhouse. Finally seeds were harvested three to five months after transplanting. The method yielded single locus transformants at a rate of over 50% (Aldemita and Hodges, Planta 199, 612-617, 1996; Chan et al., Plant Mol. Biol. 22(3), 491-506, 1993; Hiei et al., Plant J. 6(2), 271-282, 1994).

Example 4

Evaluation of Transformants: Vegetative Growth Measurements

Approximately 15 to 20 independent T0 transformants were generated. The primary transformants were transferred from tissue culture chambers to a greenhouse for growing and harvest of T1 seed. Five events of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by visual marker screening. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

These parameters were derived in an automated way from the digital images using image analysis software and were analysed statistically. A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "Null segregants" or "Nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Vegetative growth and seed yield were measured according to the methods as described above. The inventors surprisingly found that the total weight of seeds, the number of filled seeds and the harvest index were increased in the rice plants transformed with the NAP1-like gene when compared the control plants without the NAP1-like gene.

The data obtained in the first experiment were confirmed in a second experiment with T2 plants. Four lines that had the correct expression pattern were selected for further analysis. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation.

A total number of 160 NAP1-like transformed plants were evaluated in the T2 generation, that is 40 plants per event of which 20 positives for the transgene, and 20 negatives.

Example 5

Evaluation of Transformants: Measurement of Seed-Related Parameters

Upon analysis of the seeds as described above, the inventors found that plants transformed with the NAP1-like gene construct had a higher number of filled seeds, a higher total weight of seeds and an increased harvest index compared to plants lacking the NAP1-like transgene. Positive results obtained for plants in the T1 generation were again obtained in the T2 generation. Not only individual transgenic lines scored significantly better than the corresponding nullizygous control lines, but there was also a significant positive overall effect when all plants of all tested T2 events were evaluated, strongly indicating a global gene effect. An overview of the data is given in Table 3.

TABLE 3

| parameter | T1 plants % increase | p-value | T2 plants % increase | p-value | Combined analyis p-value |
|---|---|---|---|---|---|
| Total weight of seeds | 24 | 0.0076 | 28 | 0.0013 | 0.0006 |
| Number of filled seeds | 17 | 0.0352 | 28 | 0.0013 | 0.0003 |
| Harvest Index | 15 | 0.0085 | 17 | 0.0025 | 0.0003 |

The % increase presents the average increase for all tested events. The p-value stands for the p-value derived from the F-test.

Number of Filled Seeds

The number of filled seeds was determined by counting the number of filled husks that remained after the separation step. 4 of the 5 tested lines showed an increase in filled seed number, mounting up to 37%. There was an overall increase of 17% in the number of filled seeds produced by transgenic plants relative to corresponding null segregants, which increase is statistically significant (p-value 0.0352). In the T2 generation, there was increase for all tested lines, ranging between 14 and 46%. The mean increase for the T2 lines was 28%, this mean increase was also statistically significant (p-value of 0.0013). The combined analysis of T1 and T2 data also confirmed that the global gene effect was highly significant (p-value of 0.0003).

Total Seed Yield

The total seed yield (total weight of seeds) per plant was measured by weighing all filled husks harvested from a plant. All transgenic T1 lines showed an increase in total seed weight, which varied between 8 and 43%. On average, the increase in seed yield was 24% and this overall effect from the presence of the transgene on seed yield was significant, as evidenced by a P-value for the F test of 0.0076. These results were also observed in the T2 generation. The 4 tested lines had a yield increase between 14 and 48% with an average of 28%. This mean increase was statistically significant (p-value of 0.0013) and also the combined analysis of the T1 and T2 plants showed there was a global gene effect (p-value of 0.0006).

Harvest Index

The harvest index in the present invention is defined as the ratio between the total seed yield and the above ground area (mm$^2$), multiplied by a factor 10$^6$. 4 of the 5 tested lines showed an increased harvest index, ranging between 9 and 48%. There was a significant overall gene effect (an effect associated with of the presence of the transgene) on harvest index (an overall increase of 15%), with a statistically significant p-value for the F test of 0.085. Similar results were obtained for T2 plants. The harvest index for the individual lines was increased between 12 and 34% with a significant mean of 17% (p-value of 0.0025). Here too, the combined analysis of the T1 and T2 data showed a global gene effect (p-value 0.003).

It is known to persons skilled in the art that the expression of transgenes in plants, and hence also the phenotypic effect due to expression of such transgene, can differ among different independently obtained transgenic lines and progeny thereof. The transgenes present in different independently obtained transgenic plants differ from each other by the chromosomal insertion locus as well as by the number of transgene copies inserted in that locus and the configuration of those transgene copies in that locus. Differences in expression levels can be ascribed to influence from the chromosomal context of the transgene (the so-called position effect) or from silencing mechanisms triggered by certain transgene configurations (e.g. inwards facing tandem insertions of transgenes are prone to silencing at the transcriptional or post-transcriptional level). Notwithstanding these possible causes of variation, the data show that transgenic plants expressing the NAP1-like gene consistently gave a higher number of filled seeds, a higher total weight of seeds, as well as an increased Harvest Index, each relative to corresponding non-transgenic plants. The observed increases were significant in both T1 and T2 generation, which is a strong argument for a global gene effect as evidenced by the p-values of the combined analysis.

Example 6

Characterisation of a *Medicago sativa* NAP1-Like Protein

Materials and Methods

Isolation of the Full-Length cDNA Clone of the Putative Alfalfa PP2A-Inhibitor

An isolated cDNA fragment coding for a part of an alfalfa (*Medicago sativa*) putative NAP1-like protein has been used to isolate the full-length clone from an alfalfa root-nodule λ-ZAP phage cDNA library (Savoure et al. Plant Mol. Biol. 27, 1059-1070; 1995) using standard screening procedures as described by the manufacturer (Stratagene). 400 000 plaques were screened, 20 clones were retained, of which 18 were positive in the second hybridization screen. 8 of these clones were selected for further work and converted into phagemids from individual phages. Four clones were sequenced and two of them proved to be the full-length cDNA clones of the putative NAP1-like protein. One of the clones (Ms10.1) was used for further work (SEQ ID NO: 10, encoding the protein of SEQ ID NO: 11).

Production and Purification of the *Medicago* NAP1-Like Protein

Figure 4:
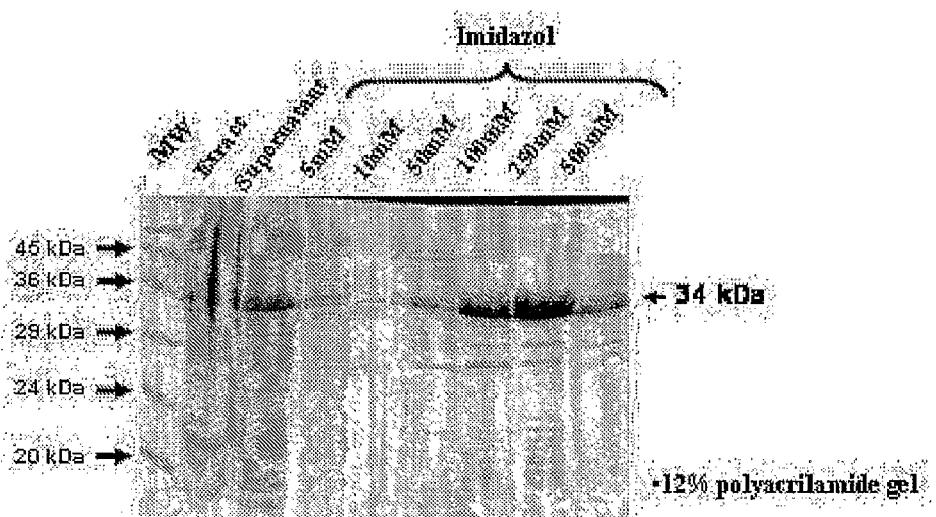
FIG. 4 The *Medicago* NAP1-like protein was expressed in *E. coli* and purified from crude cell extract by affinity chromatography via the 6×HIS-tag. Elution of the 34 kD protein at different imidazol concentrations from the nickel-agarose resin is visualised by Western blotting using anti-6×HIS antibody (Sigma, St Louis, USA).

The cDNA sequence coding for the *Medicago sativa* NAP1-like protein was inserted into the NcoI/XhoI site of the pENTRY4 Gateway® vector (Invitrogen) and subsequently introduced into the pDEST17 bacterial expression vector. The pDEST17 vector allowed the expression of the NAP1-like protein in BL21 *E. coli* cells as a 6×HIS-tagged protein. The 34 kDa NAP1-like protein was purified by affinity chromatography using a nickel agarose resin (Sigma) (FIG. 4).

Phosphatase Activity Measurements

Potential phosphatase-inhibiting activity of the *Medicago saliva* NAP1-like protein was tested in vitro on Protein Phosphatase 2A (PP2A) catalytic subunits purified from rabbit skeletal muscle using $^{32}$P-isotope-labelled glycogen phosphorylase and histone H2A proteins as substrates according to Ulloa et al. (1993).

Intracellular Localization of the MsNAP1-Like and AtNAP1-Like Proteins

Polyclonal anti-MsNAP1-like antibodies were raised in rabbits against the purified 6×HIS-tagged protein using a standard immunization protocol.

Protoplasts were isolated from suspension cultured alfalfa (*Medicago sativa*) cells and fixed by 6% formaldehyde. The cells were than attached to poly-L-lysine coated glass slides and exposed to the anti-MsNAP1-like antiserum (200× diluted in PBS), washed and exposed to FITC-conjugated goat anti-rabbit secondary antibody (SIGMA, 100× dilution). Nuclei were stained with DAPI (0.02 mg/ml) in parallel and photographed with a Nikon TE300 fluorescent microscope and a SPOT II colour CCD camera.

The coding region of the *Arabidopsis thaliana* orthologue of the *Medicago saliva* NAP1-like protein (SEQ ID NO: 1), was inserted in frame with the green fluorescent protein (GFP) into the Gateway®-compatible plant expression vector (pK7WGF2). Protoplasts were isolated and transfected with the purified plasmid DNA using standard procedures. Transient expression was recorded one or two days after transfection by fluorescence microscopy.

Results

*Arabidopsis* and *Medicago* NAP1-Like Proteins are Localised in the Nucleus

The NAP1-like protein of *Medicago sativa* was highly homologous to *Arabidopsis* NAP1-like protein: the sequence identity was 71.2% and sequence similarity was 84.5% (FIG. 5). Using the anti-MsNAP1-like antibodies, indirect immunofluorescence revealed that the antibodies recognised a protein that was localized to the nuclei of suspension cultured alfalfa cells. This localisation was verified by the nuclear stain, DAPI. Faint fluorescence was associated with the chromosomes in metaphase cells (FIG. 6.A, insert).

The GFP-tagged *Arabidopsis* NAP1-like-protein was also exclusively localised to the nuclei of suspension cultured *Arabidopsis* cells (FIG. 6.B).

Figure 7:
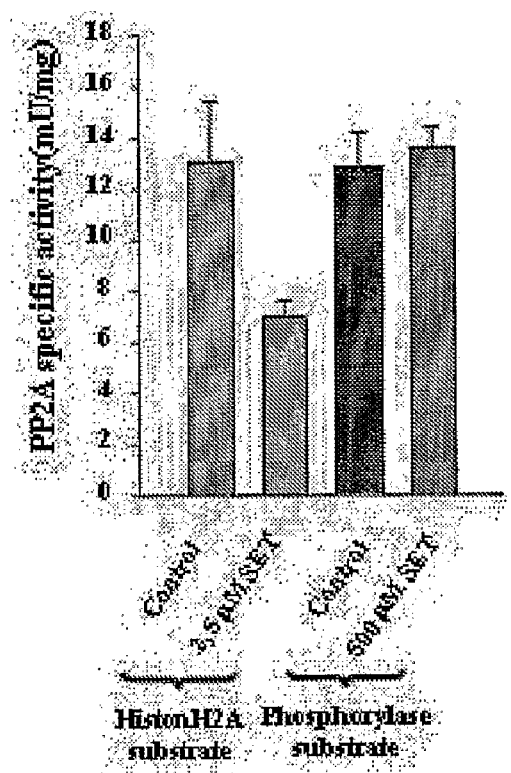
FIG. 7 The purified *Medicago* NAP1-like protein inhibits in vitro phospho-histone H2B dephosphorylation activity of PP2A (purified from rabbit skeletal muscle), but has no influence on the dephosphorylation of the glycogen phosphorylase by the same enzyme.

2) The Alfalfa NAP1-Like Protein Inhibits In Vitro PP2a Phosphatase Activity on a Phospho-Histone Substrate Purified alfalfa NAP1-like_protein was added at various concentrations to reaction mixtures containing the catalytic subunits of rabbit skeletal muscle PP2A and phosphorylated histone H2A, or glycogen phosphorylase as substrate. It was observed that the NAP1-like_protein had no influence on the dephosphorylation of the glycogen phosphorylase even at 500 mM concentration, but already 2.5 mM concentration of the NAP1-like_protein efficiently inhibited PP2A activity on the phospho-histonH2A substrate (50% decrease in activity) (FIG. 7).

CONCLUSION

The *Medicago sativa* and *Arabidopsis thaliana* NAP1-like proteins show both structurally and functionally resemblance. Plant NAP1-like_proteins inhibit in vitro phosphatase (PP2A) activity on histone substrates, indicating a possible in vivo role on chromatin organisation and gene transcription.

SEQUENCE LISTING

```
<160> NUMBER OF SEQ ID NOS: 34

<210> SEQ ID NO 1
<211> LENGTH: 1075
<212> TYPE: DNA
<213> ORGANISM: Arabidopsis thaliana

<400> SEQUENCE: 1
gtgacggaac cacaagaaga gaagagacca aaaggaggag ccaaaatcct ctctttcttt      60
ggaattaggg tttcctcaaa ggaagtgaac tgaaaatggt cgcggacaag agcaagaagt     120
cgaaaattga agagaaaggc gaagaagaaa acttggagca aatcgacgca gagcttgttc     180
tctcaattga gaagcttcag gagattcaag acgacctcga gaagattaac gaaaaggcca     240
gtgacgaggt cttggaagta gagcagaaat ataacgtgat acggaaacct gtctatgaca     300
agcgcaatga agttatccaa tcgattcctg gcttttggat gactgctttt ttgagtcatc     360
ctgccttagg cgacctcttg actgaagaag accaaaagat tttttaagtac ttgaactctc     420 tggaagtgga ggatgccaaa gatgtgaaat ctggatactc tataactttt cacttcactt     480
caaacccgtt ctttgaggat gccaagctta ccaagacatt tactttcctt gaagaaggaa     540
caacaaaaat cactgcaact cctatcaaat ggaaggaggg caagggcttg ccaaatggag     600
tgaaccatga tgataagaaa ggaaataaac gtgcattgcc agaggagagt ttctttactt     660
ggtttactga tgctcaacat aaggaagatg ctggggatga gattcatgat gaggttgctg     720
atattatcaa ggaagatctc tggtccaacc ctctcaccta cttcaacaat gatgctgatg     780
aagaggattt tgatggagat gatgatggtg acgaagaggg agaagaagac gatgacgatg     840
aagaggagga agatggtgag gaatgatggg agcccaaaga taacacattg ctggcttgct     900
tctataacag atgtgtaaag tttgtgttat gaggttctca attttagcaa tgatgagact     960
aagctttctc ttttggaata tttagtttat ttactatcaa tagctacatt ctgtttgtac    1020
gaaccatgtc atcatccatg tcctaaatct tgccataact acatctgttt ttcgc         1075
```

-continued

<210> SEQ ID NO 2
<211> LENGTH: 256
<212> TYPE: PRT
<213> ORGANISM: Arabidopsis thaliana

<400> SEQUENCE: 2

Met Val Ala Asp Lys Ser Lys Lys Ser Lys Ile Glu Glu Lys Gly Glu
1               5                   10                  15

Glu Glu Asn Leu Glu Gln Ile Asp Ala Glu Leu Val Leu Ser Ile Glu
            20                  25                  30

Lys Leu Gln Glu Ile Gln Asp Asp Leu Glu Lys Ile Asn Glu Lys Ala
        35                  40                  45

Ser Asp Glu Val Leu Glu Val Glu Gln Lys Tyr Asn Val Ile Arg Lys
    50                  55                  60

Pro Val Tyr Asp Lys Arg Asn Glu Val Ile Gln Ser Ile Pro Gly Phe
65                  70                  75                  80

Trp Met Thr Ala Phe Leu Ser His Pro Ala Leu Gly Asp Leu Leu Thr
                85                  90                  95

Glu Glu Asp Gln Lys Ile Phe Lys Tyr Leu Asn Ser Leu Glu Val Glu
            100                 105                 110

Asp Ala Lys Asp Val Lys Ser Gly Tyr Ser Ile Thr Phe His Phe Thr
        115                 120                 125

Ser Asn Pro Phe Phe Glu Asp Ala Lys Leu Thr Lys Thr Phe Thr Phe
    130                 135                 140

Leu Glu Glu Gly Thr Thr Lys Ile Thr Ala Thr Pro Ile Lys Trp Lys
145                 150                 155                 160

Glu Gly Lys Gly Leu Pro Asn Gly Val Asn His Asp Lys Lys Gly
                165                 170                 175

Asn Lys Arg Ala Leu Pro Glu Glu Ser Phe Phe Thr Trp Phe Thr Asp
            180                 185                 190

Ala Gln His Lys Glu Asp Ala Gly Asp Glu Ile His Asp Glu Val Ala
        195                 200                 205

Asp Ile Ile Lys Glu Asp Leu Trp Ser Asn Pro Leu Thr Tyr Phe Asn
    210                 215                 220

Asn Asp Ala Asp Glu Glu Asp Phe Asp Gly Asp Asp Gly Asp Glu
225                 230                 235                 240

Glu Gly Glu Glu Asp Asp Asp Glu Glu Glu Asp Gly Glu Glu
                245                 250                 255

<210> SEQ ID NO 3
<211> LENGTH: 3560
<212> TYPE: DNA
<213> ORGANISM: Artificial sequence
<220> FEATURE:
<223> OTHER INFORMATION: expression cassette

<400> SEQUENCE: 3
aatccgaaaa gtttctgcac cgttttcacc ccctaactaa caatataggg aacgtgtgct    60
aaatataaaa tgagaccttaa tatatgtagc gctgataact agaactatgc aagaaaact   120 catccaccta ctttagtggc aatcgggcta aataaaaaag agtcgctaca ctagtttcgt   180
tttccttagt aattaagtgg gaaaatgaaa tcattattgc ttagaatata cgttcacatc   240
tctgtcatga agttaaatta ttcgaggtag ccataattgt catcaaactc ttcttgaata   300
aaaaaatctt tctagctgaa ctcaatgggt aaagagagag attttttta aaaaaataga   360 atgaagatat tctgaacgta ttggcaaaga tttaaacata taattatata attttatagt   420

-continued

| | |
|---|---|
| ttgtgcattc gtcatatcgc acatcattaa ggacatgtct tactccatcc caattttttat | 480 |
| ttagtaatta aagacaattg acttattttt attatttatc tttttttcgat tagatgcaag | 540 |
| gtacttacgc acacactttg tgctcatgtg catgtgtgag tgcacctcct caatacacgt | 600 |
| tcaactagca acacatctct aatatcactc gcctatttaa tacatttagg tagcaatatc | 660 |
| tgaattcaag cactccacca tcaccagacc acttttaata atatctaaaa tacaaaaaat | 720 |
| aattttacag aatagcatga aaagtatgaa acgaactatt taggttttttc acatacaaaa | 780 |
| aaaaaaagaa ttttgctcgt gcgcgagcgc caatctccca tattgggcac acaggcaaca | 840 |
| acagagtggc tgcccacaga acaacccaca aaaacgatg atctaacgga ggacagcaag | 900 |
| tccgcaacaa ccttttaaca gcaggctttg cggccaggag agaggaggag aggcaaagaa | 960 |
| aaccaagcat cctcctcctc ccatctataa attcctcccc cctttttcccc tctctatata | 1020 |
| ggaggcatcc aagccaagaa gagggagagc accaaggaca cgcgactagc agaagccgag | 1080 |
| cgaccgcctt cttcgatcca tatcttccgg tcgagttctt ggtcgatctc ttccctcctc | 1140 |
| cacctcctcc tcacagggta tgtgcccttc ggttgttctt ggatttattg ttctaggttg | 1200 |
| tgtagtacgg gcgttgatgt taggaaaggg gatctgtatc tgtgatgatt cctgttcttg | 1260 |
| gatttgggat agaggggttc ttgatgttgc atgttatcgg ttcggtttga ttagtagtat | 1320 |
| ggttttcaat cgtctggaga gctctatgga aatgaaatgg tttagggtac ggaatcttgc | 1380 |
| gattttgtga gtaccttttg tttgaggtaa atcagagca ccggtgattt tgcttggtgt | 1440 |
| aataaaagta cggttgtttg gtcctcgatt ctggtagtga tgcttctcga tttgacgaag | 1500 |
| ctatcctttg tttattccct attgaacaaa aataatccaa ctttgaagac ggtcccgttg | 1560 |
| atgagattga atgattgatt cttaagcctg tccaaaattt cgcagctggc ttgtttagat | 1620 |
| acagtagtcc ccatcacgaa attcatggaa acagttataa tcctcaggaa caggggattc | 1680 |
| cctgttcttc cgatttgctt tagtcccaga attttttttc ccaaatatct taaaaagtca | 1740 |
| cttttctggtt cagttcaatg aattgattgc tacaaataat gctttttatag cgttatccta | 1800 |
| gctgtagttc agttaatagg taataccccct atagtttagt caggagaaga acttatccga | 1860 |
| tttctgatct ccattttttaa ttatatgaaa tgaactgtag cataagcagt attcatttgg | 1920 |
| attattttttt ttattagctc tcaccccttc attattctga gctgaaagtc tggcatgaac | 1980 |
| tgtcctcaat tttgttttttca aattcacatc gattatctat gcattatcct cttgtatcta | 2040 |
| cctgtagaag tttctttttttg gttattcctt gactgcttga ttacagaaag aaatttatga | 2100 |
| agctgtaatc gggatagtta tactgcttgt tcttatgatt catttccttt gtgcagttct | 2160 |
| tggtgtagct tgccactttc accagcaaag ttcatttaaa tcaactaggg atatcacaag | 2220 |
| tttgtacaaa aaagcaggct tcacaatggt cgcggacaag agcaagaagt cgaaaattga | 2280 |
| agagaaaggc gaagaagaaa acttggagca aatcgacgca gagcttgttc tctcaattga | 2340 |
| gaagcttcag gagattcaag acgacctcga gaagattaac gaaaaggcca gtgacgaggt | 2400 |
| cttggaagta gagcagaaat ataacgtgat acggaaacct gtctatgaca agcgcaatga | 2460 |
| agttatccaa tcgattcctg gcttttggat gactgctttt tgagtcatc ctgccttagg | 2520 |
| cgacctcttg actgaagaag accaaaagat ttttaagtac ttgaactctc tggaagtgga | 2580 |
| ggatgccaaa gatgtgaaat ctggatactc tataactttt cacttcactt caaacccgtt | 2640 |
| ctttgaggat gccaagctta ccaagacatt tactttcctt gaagaaggaa caacaaaaat | 2700 |
| cactgcaact cctatcaaat ggaaggaggg caagggcttg ccaaatggag tgaaccatga | 2760 |
| tgataagaaa ggaaataaac gtgcattgcc agaggagagt ttctttactt ggtttactga | 2820 |

```
tgctcaacat aaggaagatg ctggggatga gattcatgat gaggttgctg atattatcaa    2880
ggaagatctc tggtccaacc ctctcaccta cttcaacaat gatgctgatg aagaggattt    2940
tgatggagat gatgatggtg acgaagaggg agaagaagac gatgacgatg aagaggagga    3000
agatggtgag gaatgatggg acccagcttt cttgtacaaa gtggtgatat cacaagcccg    3060
ggcggtcttc tagggataac agggtaatta tatccctcta gatcacaagc ccgggcggtc    3120
ttctacgatg attgagtaat aatgtgtcac gcatcaccat gggtggcagt gtcagtgtga    3180
gcaatgacct gaatgaacaa ttgaaatgaa aagaaaaaaa gtactccatc tgttccaaat    3240
taaaattcat tttaaccttt taataggttt atacaataat tgatatatgt tttctgtata    3300
tgtctaattt gttatcatcc gggcggtctt ctagggataa cagggtaatt atatccctct    3360
agacaacaca caacaaataa gagaaaaaac aaataatatt aatttgagaa tgaacaaaag    3420
gaccatatca ttcattaact cttctccatc catttccatt tcacagttcg atagcgaaaa    3480
ccgaataaaa aacacagtaa attacaagca caacaaatgg tacaagaaaa acagttttcc    3540
caatgccata atactcgaac                                                3560

<210> SEQ ID NO 4
<211> LENGTH: 51
<212> TYPE: DNA
<213> ORGANISM: Artificial sequence
<220> FEATURE:
<223> OTHER INFORMATION: primer: prm1505

<400> SEQUENCE: 4
ggggacaagt ttgtacaaaa aagcaggctt cacaatggtc gcggacaaga g             51

<210> SEQ ID NO 5
<211> LENGTH: 48
<212> TYPE: DNA
<213> ORGANISM: Artificial sequence
<220> FEATURE:
<223> OTHER INFORMATION: primer: prm1506

<400> SEQUENCE: 5
ggggaccact ttgtacaaga aagctgggtc ccatcattcc tcaccatc                  48

<210> SEQ ID NO 6
<211> LENGTH: 1101
<212> TYPE: DNA
<213> ORGANISM: Nicotiana tabacum

<400> SEQUENCE: 6
agcggctggt accggtccgg aattcccggg atatcgtcga cccacgcgtc cgaaagaaga     60 gaaaagatg ggtgctgaca aagggaagaa gcaaaaagtg gaggaagaga acaacaccat     120
tgatggtgag ctcgtttttt ccattgaaaa attgcaagaa atacaagacg agctcgagaa    180
gatcaatgag gaagcaagtg ataaagtatt ggaagtggaa cagaagtaca atgagatccg    240
caagcctgtc tatgacaaac gaacgacat cattaaagct atcccggact tctggttgac    300
tgcttttttg agtcatcctg tcctaggtga acttctaact gaagaagacc aaaagatctt    360
caagtttcta agttctattg aagttgaaga ctctaaagat gtgaagtcgg gctactcgat    420 aaccctttaac ttcaatgcga atccttattt tgaaaataca aagctcacaa agacctatac    480
cttccttgaa gatggaccca caaagatttc tgctacaaca ataaaatgga aagaaggcat    540
gggcattcct aatggatttg cacatgagaa gaaaggaaac aagcgatctc atgctgagga    600
```

```
aagcttcttc acatggttca gtgaagtcaa tcaaaaagat gaggatgagg atgaggccct    660
agagattcag gatgaggtcg ctgacataat taaggatgac ttgtggccga accctctcac    720 ctatttaac aacgagcctg atgaagaaga ttttgatggt gacgagggaa aggacagtga     780
aggctctgaa gacgaagagg aagaagaaga ggaggatgag gatggtgatg aagaatgaag    840
gcagtaaact gttcaagacc cctatttggg gatctcgtct tcagcggttt taatcatcag    900
ggtttaatgt ctgtaaagag gctttgaatg ttgccaaaga acagaataac tgtggtgact    960 atacctttc ttctcttgta tggttataac ttataagcaa aatatctaat tccggaggtt     1020
ccaaaatgtt ttcattaggc tagttcgatt aatgaagtgt ttgtctggca aaaactgata   1080
atgttaggtt attgagttat g                                              1101
```

<210> SEQ ID NO 7
<211> LENGTH: 256
<212> TYPE: PRT
<213> ORGANISM: Nicotiana tabacum

<400> SEQUENCE: 7

```
Met Gly Ala Asp Lys Gly Lys Lys Gln Lys Val Glu Glu Asn Asn
1               5                  10                  15

Thr Ile Asp Gly Glu Leu Val Phe Ser Ile Glu Lys Leu Gln Glu Ile
            20                  25                  30

Gln Asp Glu Leu Glu Lys Ile Asn Glu Glu Ala Ser Asp Lys Val Leu
        35                  40                  45

Glu Val Glu Gln Lys Tyr Asn Glu Ile Arg Lys Pro Val Tyr Asp Lys
    50                  55                  60

Arg Asn Asp Ile Ile Lys Ala Ile Pro Asp Phe Trp Leu Thr Ala Phe
65                  70                  75                  80

Leu Ser His Pro Val Leu Gly Glu Leu Leu Thr Glu Asp Gln Lys
                85                  90                  95

Ile Phe Lys Phe Leu Ser Ser Ile Glu Val Asp Ser Lys Asp Val
                100                 105                 110

Lys Ser Gly Tyr Ser Ile Thr Phe Asn Phe Asn Ala Asn Pro Tyr Phe
            115                 120                 125

Glu Asn Thr Lys Leu Thr Lys Thr Tyr Thr Phe Leu Glu Asp Gly Pro
        130                 135                 140

Thr Lys Ile Ser Ala Thr Thr Ile Lys Trp Lys Glu Gly Met Gly Ile
145                 150                 155                 160

Pro Asn Gly Phe Ala His Glu Lys Lys Gly Asn Lys Arg Ser His Ala
                165                 170                 175

Glu Glu Ser Phe Phe Thr Trp Phe Ser Glu Val Asn Gln Lys Asp Glu
            180                 185                 190

Asp Glu Asp Glu Ala Leu Glu Ile Gln Asp Glu Val Ala Asp Ile Ile
        195                 200                 205

Lys Asp Asp Leu Trp Pro Asn Pro Leu Thr Tyr Phe Asn Asn Glu Pro
    210                 215                 220

Asp Glu Glu Asp Phe Asp Gly Asp Glu Gly Lys Asp Ser Glu Gly Ser
225                 230                 235                 240

Glu Asp Glu Glu Glu Glu Glu Glu Asp Glu Asp Gly Asp Glu Glu
                245                 250                 255
```

<210> SEQ ID NO 8
<211> LENGTH: 1061
<212> TYPE: DNA
<213> ORGANISM: Nicotiana tabacum -continued

<400> SEQUENCE: 8

```
tttgtacaaa aaagcaggct ggtaccggtc cggaattccc gggatatcgt cgacccacgc      60
gtccgagaaa ttagcagtta gagacactga gaagcagcag ctctcttcct cagctgctgt     120
gtgcttaggc aaagaataaa atgggggcag acaaagggaa gaagcagaaa gtggatgagg     180
aaaacaacaa tgttattgat gaaaagctca ttttttccat tgaaaaattg caagagatac     240
aagacgagct cgagaagatc aatgaaaaag caagcgacga agtgttggaa gtagaacaga     300
agtacaacga gatccgcaag cctgtctacg ataagcgaaa tgatgtcatt agctctattt     360
ctgacttctg gttgactgct ttttttgagtc atcctgttct tggtaacctt ctcactgaag     420
aggaccaaaa gattttcaaa tttgtaagtt ctattgaagt ggaagactca aaggatgtga     480
aatcgggtca ttcaatcacg tttaacttta agcccaatcc ttattttgaa aattcaaagc     540
tctcaaagac gtataccttc cttgaagatg gacctacaaa aattacagct acaacaataa     600
aatggaaaga aggcatgggc attcctaatg gagttgctga caagaagaaa ggaaacaagc     660
ggtcccacgc tgaagaaagt ttcttacat ggttcagtga agtcaatcaa aaggtgatg     720
tggatgatga cgaaaatgag attctggaca ttcaggatga tgaggttgct gaaataatca     780
aggatgactt gtggcctaac cctctcaatt attttgacca tgagcctgat gaagaagata     840
ttgagggcga tgagggaaag gacagcggag gctctgaaga ggaagaagaa gaggaagatg     900
atgaagatga agaagacgaa tgaactgttg gtagaccttg tgtttgattt gagttctcat     960
cagtgtttca atcatcagag ttggtctctg taaagaggtt tcggatattg cagaaaaatt    1020
gaatgacata tagtggtgac tctaattttt agtttcagtg a                        1061
```

<210> SEQ ID NO 9
<211> LENGTH: 260
<212> TYPE: PRT
<213> ORGANISM: Nicotiana tabacum

<400> SEQUENCE: 9

```
Met Gly Ala Asp Lys Gly Lys Lys Gln Lys Val Asp Glu Glu Asn Asn
1               5                   10                  15

Asn Val Ile Asp Glu Lys Leu Ile Phe Ser Ile Glu Lys Leu Gln Glu
            20                  25                  30

Ile Gln Asp Glu Leu Glu Lys Ile Asn Glu Lys Ala Ser Asp Glu Val
        35                  40                  45

Leu Glu Val Glu Gln Lys Tyr Asn Glu Ile Arg Lys Pro Val Tyr Asp
    50                  55                  60

Lys Arg Asn Asp Val Ile Ser Ser Ile Ser Asp Phe Trp Leu Thr Ala
65                  70                  75                  80

Phe Leu Ser His Pro Val Leu Gly Asn Leu Leu Thr Glu Glu Asp Gln
                85                  90                  95

Lys Ile Phe Lys Phe Val Ser Ser Ile Glu Val Glu Asp Ser Lys Asp
            100                 105                 110

Val Lys Ser Gly His Ser Ile Thr Phe Asn Phe Lys Pro Asn Pro Tyr
        115                 120                 125

Phe Glu Asn Ser Lys Leu Ser Lys Thr Tyr Thr Phe Leu Glu Asp Gly
    130                 135                 140

Pro Thr Lys Ile Thr Ala Thr Thr Ile Lys Trp Lys Glu Gly Met Gly
145                 150                 155                 160

Ile Pro Asn Gly Val Ala Asp Lys Lys Lys Gly Asn Lys Arg Ser His
                165                 170                 175
```

```
Ala Glu Glu Ser Phe Phe Thr Trp Phe Ser Glu Val Asn Gln Lys Gly
            180                 185                 190

Asp Val Asp Asp Glu Asn Glu Ile Leu Asp Ile Gln Asp Asp Glu
        195                 200                 205

Val Ala Glu Ile Ile Lys Asp Asp Leu Trp Pro Asn Pro Leu Asn Tyr
        210                 215                 220

Phe Asp His Glu Pro Asp Glu Glu Asp Ile Glu Gly Asp Glu Gly Lys
225                 230                 235                 240

Asp Ser Gly Gly Ser Glu Glu Glu Glu Glu Glu Asp Asp Glu Asp
                245                 250                 255

Glu Glu Asp Glu
        260

<210> SEQ ID NO 10
<211> LENGTH: 1210
<212> TYPE: DNA
<213> ORGANISM: Medicago sativa
<220> FEATURE:
<221> NAME/KEY: misc_feature
<222> LOCATION: (1014)..(1014)
<223> OTHER INFORMATION: n is a, c, g, or t

<400> SEQUENCE: 10
ggcacgagca aaaccctaac acttccctca ttcacgctcg aagaaaagaa cacaaatctc      60
tccactgcgc tagggtttga aacccaacac cttctgtttc ttcaaccatg gtggccgaca    120
agtctaagaa gttgaaagtt tctgaaaagg gtgaaaacgc tgaagagatc gacggagaac    180
ttgttctctc cattgaaaag ttgcaggaaa ttcaagatga gattgaaaag atcaatgagg    240
aggctagcga taaagttctc gaaatagagc agaagtacaa tgaagtaagg aaaccggtgt    300
atgacaagcg caatgatgtg atcaagtcca ttcccgattt ctggctaact gcgttttga     360 gccatcctgt tcttggtgat ctcttgaatg aagaagatca gaagatattt aagcatttaa    420
tctctcttga ggtggaagat cataaagatg ttaaatcagg ctattcaatc acatttaact    480
tcgactccaa tccctttttt gaggattcaa aacttgttaa gacttttacc ttccttgaag    540
aaggaaccac aaagcttacc gccacaccca taaaatggaa agagggcaag gcattccca     600 atggagttat tcatgagaag aaagggaaca agcgagctgc ttctgatatc agtttctta     660 cctggttttg tgacactgag cagaaagatg aaatgggtga cattcatgat gagattgctg    720 aaaatgatcaa ggatgattta tggccgaatc cactcaatta tttcaacagt gaggaccctg    780
atgaagcaga ggaggaggat gatgaagctg gtgatgcggg aaaggatgat gatgactctg    840
aagatgatga tgatcaagag gatgacgacg atgacgagga agaagaatag tgtaaaatgc    900
tttaaaatag taatacttgg ttttaattta tttattttaa ggttattata ggagtatctt    960
agtggtcttt aggggatgat gaaagaccaa ggttggctat tggttttccc cctntgggcg   1020
taaaccttat ttattgtgct ttgaaggtga tttctggttt tatctttgtg cgcttcttcc   1080
aagataccaa tgatacatcg gatttattct tagtcctata ttgaaaccat atagtagtta   1140
aaatgtagta tattcagtgt atagctgcgt aatcagtatc attttattgc tatcacaact   1200
ttacagtacc                                                          1210

<210> SEQ ID NO 11
<211> LENGTH: 260
<212> TYPE: PRT
<213> ORGANISM: Medicago sativa
```

<400> SEQUENCE: 11

```
Met Val Ala Asp Lys Ser Lys Lys Leu Lys Val Ser Glu Lys Gly Glu
1               5                   10                  15

Asn Ala Glu Glu Ile Asp Gly Glu Leu Val Leu Ser Ile Glu Lys Leu
            20                  25                  30

Gln Glu Ile Gln Asp Glu Ile Glu Lys Ile Asn Glu Glu Ala Ser Asp
        35                  40                  45

Lys Val Leu Glu Ile Glu Gln Lys Tyr Asn Glu Val Arg Lys Pro Val
    50                  55                  60

Tyr Asp Lys Arg Asn Asp Val Ile Lys Ser Ile Pro Asp Phe Trp Leu
65                  70                  75                  80

Thr Ala Phe Leu Ser His Pro Val Leu Gly Asp Leu Leu Asn Glu Glu
                85                  90                  95

Asp Gln Lys Ile Phe Lys His Leu Ile Ser Leu Glu Val Glu Asp His
            100                 105                 110

Lys Asp Val Lys Ser Gly Tyr Ser Ile Thr Phe Asn Phe Asp Ser Asn
        115                 120                 125

Pro Phe Phe Glu Asp Ser Lys Leu Val Lys Thr Phe Thr Phe Leu Glu
    130                 135                 140

Glu Gly Thr Thr Lys Leu Thr Ala Thr Pro Ile Lys Trp Lys Glu Gly
145                 150                 155                 160

Lys Gly Ile Pro Asn Gly Val Ile His Glu Lys Gly Asn Lys Arg
                165                 170                 175

Ala Ala Ser Asp Ile Ser Phe Phe Thr Trp Phe Cys Asp Thr Glu Gln
            180                 185                 190

Lys Asp Glu Met Gly Asp Ile His Asp Glu Ile Ala Glu Met Ile Lys
        195                 200                 205

Asp Asp Leu Trp Pro Asn Pro Leu Asn Tyr Phe Asn Ser Glu Asp Pro
    210                 215                 220

Asp Glu Ala Glu Glu Asp Asp Glu Ala Gly Asp Ala Gly Lys Asp
225                 230                 235                 240

Asp Asp Asp Ser Glu Asp Asp Asp Gln Glu Asp Asp Asp Asp
            245                 250                 255

Glu Glu Glu Glu
        260
```

<210> SEQ ID NO 12
<211> LENGTH: 907
<212> TYPE: DNA
<213> ORGANISM: Zea mays

<400> SEQUENCE: 12

```
gttcctacct tcttccctcc gtctcccagc tcgcgcaggc aggcgacaca gcgacgctaa      60
aaaccctaga gcgaggaggc gtgccaggcc agcggtttgc gatgacggca ccggcggaca     120
aggggaagaa ggccaagacc gatgccgacg gcggcgagga gaacgagcaa atcgacggcg     180
cccttgtctt ctccatcgag aagctccagg agattcagga cgagctcgag aaggttaatg     240
aggaagcaag tgacaaggtt atggaggtgg agcagaaata cagtgagatt cgcagacctg     300
tctatctcaa gagggggtgac attatcaaga ccatcccgga cttttggctc acagcgtttt     360
tgagccatcc tctactaagt gagcttctga ctgaagagga tcagaagata ttcaagtact     420
tggactccat tgatgtcgat gattctgatg ttaaggcagg atattccatt taccttaact     480
tctctgagaa cccgtacttt gaagacacaa agcttacaaa gacctattcc tttgttgatg     540
```

```
atggaacaac cacaataaaa gcttctcaaa ttaagtggaa ggatggaatg ggacctgcaa      600
atggaaatgg tattaacaag aagggaaaca agcggccatt agtagtggaa agttttttct      660
cctggtttag tgatacagag ctcaagagtc ttgctgatgg tgtgcaagat gaggtggcgg      720
agatcatcaa ggaagacttg tggcctaatc ctttgaagta cttcaacaat gaggttgaag      780
atgaatttga aggagatgaa gaagatgatg acgacgacga cgacgatgat aatttggatg      840
gtgatgacaa tgacgatgat ggggaccagg agaactgagc cctcgcgttt aggcggggaa      900
ttatgtg                                                                907
```

<210> SEQ ID NO 13
<211> LENGTH: 258
<212> TYPE: PRT
<213> ORGANISM: Zea mays

<400> SEQUENCE: 13

```
Met Thr Ala Pro Ala Asp Lys Gly Lys Lys Ala Lys Thr Asp Ala Asp
  1               5                  10                  15

Gly Gly Glu Glu Asn Glu Gln Ile Asp Gly Ala Leu Val Phe Ser Ile
             20                  25                  30

Glu Lys Leu Gln Glu Ile Gln Asp Glu Leu Glu Lys Val Asn Glu Glu
         35                  40                  45

Ala Ser Asp Lys Val Met Glu Val Glu Gln Lys Tyr Ser Glu Ile Arg
     50                  55                  60

Arg Pro Val Tyr Leu Lys Arg Gly Asp Ile Ile Lys Thr Ile Pro Asp
 65                  70                  75                  80

Phe Trp Leu Thr Ala Phe Leu Ser His Pro Leu Leu Ser Glu Leu Leu
                 85                  90                  95

Thr Glu Glu Asp Gln Lys Ile Phe Lys Tyr Leu Asp Ser Ile Asp Val
            100                 105                 110

Asp Asp Ser Asp Val Lys Ala Gly Tyr Ser Ile Tyr Leu Asn Phe Ser
        115                 120                 125

Glu Asn Pro Tyr Phe Glu Asp Thr Lys Leu Thr Lys Thr Tyr Ser Phe
    130                 135                 140

Val Asp Asp Gly Thr Thr Thr Ile Lys Ala Ser Gln Ile Lys Trp Lys
145                 150                 155                 160

Asp Gly Met Gly Pro Ala Asn Gly Asn Gly Ile Asn Lys Lys Gly Asn
                165                 170                 175

Lys Arg Pro Leu Val Val Glu Ser Phe Phe Ser Trp Phe Ser Asp Thr
            180                 185                 190

Glu Leu Lys Ser Leu Ala Asp Gly Val Gln Asp Glu Val Ala Glu Ile
        195                 200                 205

Ile Lys Glu Asp Leu Trp Pro Asn Pro Leu Lys Tyr Phe Asn Asn Glu
    210                 215                 220

Val Glu Asp Glu Phe Glu Gly Asp Glu Asp Asp Asp Asp Asp
225                 230                 235                 240

Asp Asp Asp Asn Leu Asp Gly Asp Asn Asp Asp Gly Asp Gln
                245                 250                 255

Glu Asn
```

<210> SEQ ID NO 14
<211> LENGTH: 780
<212> TYPE: DNA
<213> ORGANISM: Oryza sativa

<400> SEQUENCE: 14

```
atggcggcgg cggagcagaa ggggaagaag ccgaggaccg acggcgcgga ggccgagccc      60
gtcgacgccg ccctgctgca gtccatcgag aagctccagg agatccagga cgagatcgag     120
aaggttaatg aggaagcatg tgataaagtt ctggagttgg aacagaaata caacgaggtt     180
cgcagaccag tttatgttcg acggaataaa attatcaagc aaattcctga cttctggctg     240
acagcgtttc ttagccatcc tatgcttggt gaactattaa ctgaagatga tcaaaagatt     300
ttcaaacact tggagtctat cgacgtggat gactcagaag atatcaaatc aggctactcc     360
attactctca cattctcccc caatccatat tttgaagata caaagcttac aaaaacatat     420
tcctttagtg acgatgaagc agtcaaagta aaggctacct ccatcaggtg gaagaaagga     480
atggatattg ccaatgatcg tgcgtacacg aagaaagggg acaagcgaat cttaattgat     540
gaaagtttct ttacttggtt caatagtgaa aagaacagaa gttttgctca tggagctatg     600
gatgaggtgg cagatgtcat caaggaagat ctgtggccta atcctttgaa gtacttcaac     660
aatgaatttg aagaagaatt agagctactg gatgacgatg acgaggtatc tgatgatgac     720
gatgaggagg aggatgatga agaccaaggt gaaggagagg aggatggaga ggagaactga     780
```

<210> SEQ ID NO 15
<211> LENGTH: 259
<212> TYPE: PRT
<213> ORGANISM: Oryza sativa

<400> SEQUENCE: 15

```
Met Ala Ala Ala Glu Gln Lys Gly Lys Lys Pro Arg Thr Asp Gly Ala
1               5                   10                  15

Glu Ala Glu Pro Val Asp Ala Ala Leu Leu Gln Ser Ile Glu Lys Leu
            20                  25                  30

Gln Glu Ile Gln Asp Glu Ile Glu Lys Val Asn Glu Glu Ala Cys Asp
        35                  40                  45

Lys Val Leu Glu Leu Glu Gln Lys Tyr Asn Glu Val Arg Arg Pro Val
    50                  55                  60

Tyr Val Arg Arg Asn Lys Ile Ile Lys Gln Ile Pro Asp Phe Trp Leu
65                  70                  75                  80

Thr Ala Phe Leu Ser His Pro Met Leu Gly Glu Leu Leu Thr Glu Asp
                85                  90                  95

Asp Gln Lys Ile Phe Lys His Leu Glu Ser Ile Asp Val Asp Asp Ser
            100                 105                 110

Glu Asp Ile Lys Ser Gly Tyr Ser Ile Thr Leu Thr Phe Ser Pro Asn
        115                 120                 125

Pro Tyr Phe Glu Asp Thr Lys Leu Thr Lys Thr Tyr Ser Phe Ser Asp
    130                 135                 140

Asp Glu Ala Val Lys Val Lys Ala Thr Ser Ile Arg Trp Lys Lys Gly
145                 150                 155                 160

Met Asp Ile Ala Asn Asp Arg Ala Tyr Thr Lys Lys Gly Asp Lys Arg
                165                 170                 175

Ile Leu Ile Asp Glu Ser Phe Phe Thr Trp Phe Asn Ser Glu Lys Asn
            180                 185                 190

Arg Ser Phe Ala His Gly Ala Met Asp Glu Val Ala Asp Val Ile Lys
        195                 200                 205

Glu Asp Leu Trp Pro Asn Pro Leu Lys Tyr Phe Asn Asn Glu Phe Glu
    210                 215                 220

Glu Glu Leu Glu Leu Leu Asp Asp Asp Asp Glu Val Ser Asp Asp Asp
225                 230                 235                 240
```

Asp Glu Glu Glu Asp Asp Glu Asp Gln Gly Glu Gly Glu Glu Asp Gly
            245                 250                 255

Glu Glu Asn

<210> SEQ ID NO 16
<211> LENGTH: 1315
<212> TYPE: DNA
<213> ORGANISM: Oryza sativa

<400> SEQUENCE: 16
ctccgctctc ctccagctcc gcctccgacg cgcgcacgcc tctccctccc ctcctcctcc     60
gcctcgcctc gcagtgtgga agaaaggaag gaaggctaaa accctagcga gcgcgcgagc    120
gagcgagggc tctctgcttc cttgcgatga cggcgccggc ggacaagggg aagaaggcca    180
agaccgacgc cgacggcggc gccgccgagg agaacgagca gatcgacggc gccctcgtcc    240
tctccatcga gaagctccag gagatccagg acgagctcga gaaggtcaat gaggaagcta    300
gtgacaaggt tttggaggtc gagcagaaat acagtgagat tcgcagacct gtctatctcc    360
gaaggagtga cgttatccaa caatccccg acttctggct gacagcgttt ctgagtcatc      420
ctctacttag tgagcttttg accgaagagg atcaaaagat gttcaagtac ctggagtctg    480
tcgacgtgga tgattctaaa gatgtcaagt caggctactc cataactctt accttctccg    540
agaacccgta ctttgaagac aaagagctca cgaagacata tgccttcgct gatgacggaa    600
caaccacaat aaatgctact agcattaagt ggaaagaagg aatggaaatt gcaaatggga    660
atgccaagaa gaaagggagc aagcgaccat ggttgaggaa agtttcttc acctggttta       720 ctgatacaga gcacaagagt cttgctgatg gtgtgcaaga tgaggtggct gagatcatca    780
aggaagacct gtggcccaat ccattgaagt atttcaataa tgaggctgaa gagttaggag    840
aggatgacga cgaagagggg tctgatgctg atgagggtga agaggatgag gaggaggaga    900
actgagtcta ggatgtcaga ttgcgatggt gccgatcgtc tgcattttgt ggatgctgtc    960
actctgaagg gcgaagttgc gtgaccctcg gttgcttctt tcttttttct ttttgatgac    1020
ttagctggaa cccttaggaa ctgtttaatg ccttatggag tccgtcgtat tttcgactca    1080
aaggagacac ctctatatca taatctgcgt ataaccatgg aagacatttt aacctgctga    1140
tgtgtggttc attgcgctgc ctctggtgct gtagggtgtt cgttcctttg tgctctctgt    1200 ctttttttt tttttttgtg tgtgtgtggt cgcgctggca ttgttgccag tctgatgggc      1260
tgttatttct ccccctagaa agagtgaaaa acctggcttg tgatcattgt ttacg         1315

<210> SEQ ID NO 17
<211> LENGTH: 252
<212> TYPE: PRT
<213> ORGANISM: Oryza sativa

<400> SEQUENCE: 17

Met Thr Ala Pro Ala Asp Lys Gly Lys Lys Ala Lys Thr Asp Ala Asp
1               5                   10                  15

Gly Gly Ala Ala Glu Glu Asn Glu Gln Ile Asp Gly Ala Leu Val Leu
            20                  25                  30

Ser Ile Glu Lys Leu Gln Glu Ile Gln Asp Glu Leu Glu Lys Val Asn
        35                  40                  45

Glu Glu Ala Ser Asp Lys Val Leu Glu Val Glu Gln Lys Tyr Ser Glu
    50                  55                  60

Ile Arg Arg Pro Val Tyr Leu Arg Arg Ser Asp Val Ile Gln Thr Ile

|     |     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- | --- |

Pro Asp Phe Trp Leu Thr Ala Phe Leu Ser His Pro Leu Leu Ser Glu
                        85                        90                        95

Leu Leu Thr Glu Glu Asp Gln Lys Met Phe Lys Tyr Leu Glu Ser Val
          100                    105                    110

Asp Val Asp Asp Ser Lys Asp Val Lys Ser Gly Tyr Ser Ile Thr Leu
          115                    120                    125

Thr Phe Ser Glu Asn Pro Tyr Phe Glu Asp Lys Glu Leu Thr Lys Thr
    130                    135                    140

Tyr Ala Phe Ala Asp Asp Gly Thr Thr Thr Ile Asn Ala Thr Ser Ile
145                    150                    155                    160

Lys Trp Lys Glu Gly Met Glu Ile Ala Asn Gly Asn Ala Lys Lys Lys
          165                    170                    175

Gly Ser Lys Arg Pro Leu Val Glu Glu Ser Phe Phe Thr Trp Phe Thr
          180                    185                    190

Asp Thr Glu His Lys Ser Leu Ala Asp Gly Val Gln Asp Glu Val Ala
          195                    200                    205

Glu Ile Ile Lys Glu Asp Leu Trp Pro Asn Pro Leu Lys Tyr Phe Asn
    210                    215                    220

Asn Glu Ala Glu Glu Leu Gly Glu Asp Asp Glu Glu Gly Ser Asp
225                    230                    235                    240

Ala Asp Glu Gly Glu Glu Asp Glu Glu Glu Asn
          245                    250

```
<210> SEQ ID NO 18
<211> LENGTH: 958
<212> TYPE: DNA
<213> ORGANISM: Zea mays

<400> SEQUENCE: 18
ccaaaagggt cacagttccg cctccttttc ctgccttcct cctcactagt cgctcccccg     60
cggctcgcgc aggcgggcga cacaacgagg ctaaatccct atcgcgagga ggcgtgtgag    120
gccagcggct tgcgatgac agcaccagcg acaaggggga agaaggccaa gactgatgcc     180
gacggcggcg aggagaacga acagatcgac ggcgtcctcg tcctctccat cgagaagctc    240
caggagatac aggacgagct cgagaaggta aatgaggaag caagtgacaa ggttatggag    300
gtggagcaga atacagtga atccgcagaa cctgtctatc tcaagagggg tgacattatc     360
aagaccatcc cggacttttg gctcacagcg tttatgagcc atcctctatt aagtgagctt    420
ctgactgaag gaccagaa gatattcaag tacttagact ccattgatgt ggatgattct     480
gatgttaagg caggatactc cattcatctt aacttctctg agaacccgta ctttgaggac    540
acaaagcttg caaagaccta tctttgct gatgatggaa caaccacaat aaaagcttcc      600
gaaattaagt ggaaggaagg aatgggacct gcaaatggaa atggtattaa caagaagggg    660
agtaagcggc cattagtaga ggaaagtttt tttagctggt ttggtgatac agagctcaag    720
agtcttgctg atggtgtgca agatgaggtg gcggagatca taaggaaga tttgtggcct    780 aatcctttga gtacttcaa caatgaggtt gacgatgaat tgaaggaga tgaagatgat     840 gatgatttgg atggtgatga tgacgatgaa ggcgatgatt ggagaactg agcccttgcg    900 cttggttcag aatgttgtcc gtggatgatg tggctgggcg gaactgtgac ccttttgg     958

<210> SEQ ID NO 19
<211> LENGTH: 251
<212> TYPE: PRT
```

<213> ORGANISM: Zea mays

<400> SEQUENCE: 19

```
Met Thr Ala Pro Ala Asp Lys Gly Lys Lys Ala Lys Thr Asp Ala Asp
1               5                   10                  15
Gly Gly Glu Glu Asn Glu Gln Ile Asp Gly Val Leu Val Leu Ser Ile
            20                  25                  30
Glu Lys Leu Gln Glu Ile Gln Asp Glu Leu Glu Lys Val Asn Glu Glu
        35                  40                  45
Ala Ser Asp Lys Val Met Glu Val Gln Lys Tyr Ser Glu Ile Arg
    50                  55                  60
Arg Pro Val Tyr Leu Lys Arg Gly Asp Ile Ile Lys Thr Ile Pro Asp
65                  70                  75                  80
Phe Trp Leu Thr Ala Phe Met Ser His Pro Leu Leu Ser Glu Leu Leu
                85                  90                  95
Thr Glu Glu Asp Gln Lys Ile Phe Lys Tyr Leu Asp Ser Ile Asp Val
            100                 105                 110
Asp Asp Ser Asp Val Lys Ala Gly Tyr Ser Ile His Leu Asn Phe Ser
        115                 120                 125
Glu Asn Pro Tyr Phe Glu Asp Thr Lys Leu Ala Lys Thr Tyr Ile Phe
    130                 135                 140
Ala Asp Asp Gly Thr Thr Thr Ile Lys Ala Ser Glu Ile Lys Trp Lys
145                 150                 155                 160
Glu Gly Met Gly Pro Ala Asn Gly Asn Gly Ile Asn Lys Lys Gly Ser
                165                 170                 175
Lys Arg Pro Leu Val Glu Glu Ser Phe Phe Ser Trp Phe Gly Asp Thr
            180                 185                 190
Glu Leu Lys Ser Leu Ala Asp Gly Val Gln Asp Glu Val Ala Glu Ile
        195                 200                 205
Ile Lys Glu Asp Leu Trp Pro Asn Pro Leu Lys Tyr Phe Asn Asn Glu
    210                 215                 220
Val Asp Asp Glu Phe Glu Gly Asp Glu Asp Asp Asp Leu Asp Gly
225                 230                 235                 240
Asp Asp Asp Asp Glu Gly Asp Asp Leu Glu Asn
                245                 250
```

<210> SEQ ID NO 20
<211> LENGTH: 1257
<212> TYPE: DNA
<213> ORGANISM: Arabidopsis thaliana

<400> SEQUENCE: 20

```
agattcacgc atcacacaat cgagttttta gggttttagc ggttgctctc tcggaagcca      60
gagagaagag ggaagaggaa gtctaattcc tctgcgtttt ttgcaattag gttttctca     120
attggaatcg aaaatggtga cagacaagag caagaaggcg aaaaccgaag aagaaaacgt     180
cgagcaaatc gatgcagagc ttgtcctctc aatcgaaaag cttcaagaga tccaagacga     240
cctcgagaag ataaatgaaa aggctagtga tgaagtgttg gaagtggagc agaaatataa     300
tgtgataagg aaacctgttt atgacaagcg taacgagatc atcaaaacca tccctgattt     360
ctggttaact gctttcttga gtcaccctgc tttaggtgaa cttttgactg aagaagacca     420
aaagattttc aaatatctta gctctcttga tgttgaggat gccaaagatg tgaaatctgg     480
atactctatc actttttcct tcaatcccaa tccattttt gaagatggaa aactgacaaa     540
gactttttacc tttctcgaag aagggacaac caaaatcaca gccacgccta tcaaatggaa     600
```

-continued

```
agagggcaaa ggcctggcga atggagtgaa tcatgagaag aatggaaaca aacgtgcact    660
acctgaagag agcttcttta cctggtttag tgatgctcaa cacaaggagg atgttgagga    720
tgagatgcaa gacgagcagg ttgcagatat catcaaggaa gatttgtggc ccaaccctct    780
cacctacttc aacaatgacg ctgatgaaga ggactttgat ggagacgatg atggagatga    840
agaggagaaa gaaggtgact ctgatgaaga tgatgacgaa gaagacgaag ttggtgagga    900
atgatggcag ggatacccag aaaccacatt tgcttacatg tcttctctat aacagagtgt    960
gtaaagtttt gtgtgttgaa aggtttttaa ttttaagcaa aagtggatta tgacgacaac   1020
agacaagctt ttaattttat tttaccgtaa tagttatatc ttgttgtaag aaaccatttt   1080
cagccttttg ttggaaaatc ctgcttaaat ggttttgag tcttacataa tagcttcttc    1140
atcttttgtc ttcttaaaga gaattatatt tgtaatttca tgtctgttgt gtttctttga   1200
ctttactgaa tagagaattt gtgtgtttat ggtgaaaata tagccgatct gcttgac      1257
```

<210> SEQ ID NO 21
<211> LENGTH: 256
<212> TYPE: PRT
<213> ORGANISM: Arabidopsis thaliana

<400> SEQUENCE: 21

```
Met Val Thr Asp Lys Ser Lys Ala Lys Thr Glu Glu Glu Asn Val
1               5                  10                  15

Glu Gln Ile Asp Ala Glu Leu Val Leu Ser Ile Glu Lys Leu Gln Glu
            20                  25                  30

Ile Gln Asp Asp Leu Glu Lys Ile Asn Glu Lys Ala Ser Asp Glu Val
        35                  40                  45

Leu Glu Val Glu Gln Lys Tyr Asn Val Ile Arg Lys Pro Val Tyr Asp
    50                  55                  60

Lys Arg Asn Glu Ile Ile Lys Thr Ile Pro Asp Phe Trp Leu Thr Ala
65                  70                  75                  80

Phe Leu Ser His Pro Ala Leu Gly Glu Leu Leu Thr Glu Glu Asp Gln
                85                  90                  95

Lys Ile Phe Lys Tyr Leu Ser Ser Leu Asp Val Glu Asp Ala Lys Asp
            100                 105                 110

Val Lys Ser Gly Tyr Ser Ile Thr Phe Ser Phe Asn Pro Asn Pro Phe
        115                 120                 125

Phe Glu Asp Gly Lys Leu Thr Lys Thr Phe Thr Phe Leu Glu Glu Gly
    130                 135                 140

Thr Thr Lys Ile Thr Ala Thr Pro Ile Lys Trp Lys Glu Gly Lys Gly
145                 150                 155                 160

Leu Ala Asn Gly Val Asn His Glu Lys Asn Gly Asn Lys Arg Ala Leu
                165                 170                 175

Pro Glu Glu Ser Phe Phe Thr Trp Phe Ser Asp Ala Gln His Lys Glu
            180                 185                 190

Asp Val Glu Asp Glu Met Gln Asp Glu Gln Val Ala Asp Ile Ile Lys
        195                 200                 205

Glu Asp Leu Trp Pro Asn Pro Leu Thr Tyr Phe Asn Asn Asp Ala Asp
    210                 215                 220

Glu Glu Asp Phe Asp Gly Asp Asp Gly Asp Glu Glu Glu Lys Glu
225                 230                 235                 240

Gly Asp Ser Asp Glu Asp Asp Glu Glu Asp Glu Val Gly Glu Glu
                245                 250                 255
```

<210> SEQ ID NO 22
<211> LENGTH: 1003
<212> TYPE: DNA
<213> ORGANISM: Lycopersicon esculentum

<400> SEQUENCE: 22

| | | | | | |
|---|---|---|---|---|---|
| gcgaaatcaa | gaaaatcagt | taagcagctc | tgtaactcag | gtgggaaaaa | ggcaaaaaat | 60 |
| aatggtggtt | gacaaaggga | agaagcagaa | agtggaagag | gaaagctaca | ttgatgaaaa | 120 |
| gctcattttt | tccattgaaa | aattgcaaga | aatacaagac | gaccttgaca | agatcaatga | 180 |
| gaaagcaagt | gaggaagtgt | tggaaataga | acagaagtac | aacaagatcc | gcaagcctgt | 240 |
| ttatgataag | cggaatgata | tcattaactc | tatttctgac | ttctggttga | ctgctttttt | 300 |
| gagtcatcct | gttcttggtg | accttctaac | tgaagaggca | caaagatttt | caaattctt | 360 |
| aagttctatt | gaagtggaag | actcgaaaga | tgtgaaattt | ggttactcaa | tcacgtttaa | 420 |
| ctttaagccc | aatcctttct | ttgaaaattc | aaagctctca | agacctata | ccttccttga | 480 |
| agatggacct | acaaaaatca | cagctacacc | aataaaatgg | aaagaaggca | aaggcattcc | 540 |
| taatggcgtt | gctcaggaga | agaaaggaaa | caagcgatcc | catgctgaag | agagcttctt | 600 |
| cacctggttc | agtgaagtca | ataaaaaaga | tgatagcgat | gatgatgaaa | atgaggttct | 660 |
| ggagattcag | gatgaggttg | ctgaaataat | caaggatgac | ttgtggccaa | acccttaac | 720 |
| ttattttacc | aatgaacctg | atgaagaaga | ttttgagggt | gatgaaggtg | gtgatgaggg | 780 |
| ggaggactct | gaagatgaag | gtgatgagga | ggaagaggaa | gacgacgaag | atgaagatga | 840 |
| caaatgaact | gttaatggac | ctcatatttg | atttgatttc | tcttcttcaa | tgtttcaatt | 900 |
| atcatagttg | gtatctgtaa | agaagcttaa | tattgcagat | aaaatcgaat | tatatatagt | 960 |
| ggtgactgct | tttttttctaa | aaaaaaaaaa | aaaaaaaaa | aaa | | 1003 |

<210> SEQ ID NO 23
<211> LENGTH: 261
<212> TYPE: PRT
<213> ORGANISM: Lycopersicon esculentum

<400> SEQUENCE: 23

Met Val Val Asp Lys Gly Lys Lys Gln Lys Val Glu Glu Ser Tyr
1               5                   10                  15

Ile Asp Glu Lys Leu Ile Phe Ser Ile Glu Lys Leu Gln Glu Ile Gln
            20                  25                  30

Asp Asp Leu Asp Lys Ile Asn Glu Lys Ala Ser Glu Glu Val Leu Glu
        35                  40                  45

Ile Glu Gln Lys Tyr Asn Lys Ile Arg Lys Pro Val Tyr Asp Lys Arg
    50                  55                  60

Asn Asp Ile Ile Asn Ser Ile Ser Asp Phe Trp Leu Thr Ala Phe Leu
65                  70                  75                  80

Ser His Pro Val Leu Gly Asp Leu Leu Thr Glu Glu Asp Gln Lys Ile
                85                  90                  95

Phe Lys Phe Leu Ser Ser Ile Glu Val Glu Asp Ser Lys Asp Val Lys
            100                 105                 110

Phe Gly Tyr Ser Ile Thr Phe Asn Phe Lys Pro Asn Pro Phe Phe Glu
        115                 120                 125

Asn Ser Lys Leu Ser Lys Thr Tyr Thr Phe Leu Glu Asp Gly Pro Thr
    130                 135                 140

Lys Ile Thr Ala Thr Pro Ile Lys Trp Lys Glu Gly Lys Gly Ile Pro
145                 150                 155                 160

```
Asn Gly Val Ala Gln Glu Lys Lys Gly Asn Lys Arg Ser His Ala Glu
                165                 170                 175

Glu Ser Phe Phe Thr Trp Phe Ser Glu Val Asn Lys Lys Asp Asp Ser
            180                 185                 190

Asp Asp Asp Glu Asn Glu Val Leu Glu Ile Gln Asp Glu Val Ala Glu
            195                 200                 205

Ile Ile Lys Asp Asp Leu Trp Pro Asn Pro Leu Thr Tyr Phe Thr Asn
            210                 215                 220

Glu Pro Asp Glu Glu Asp Phe Glu Gly Asp Glu Gly Gly Asp Glu Gly
225                 230                 235                 240

Glu Asp Ser Glu Asp Glu Gly Asp Glu Glu Glu Glu Asp Glu
            245                 250                 255

Asp Glu Asp Asp Lys
            260

<210> SEQ ID NO 24
<211> LENGTH: 1557
<212> TYPE: DNA
<213> ORGANISM: Arabidopsis thaliana

<400> SEQUENCE: 24
```

| | | | | | |
|---|---|---|---|---|---|
| gtccctagtc | tcttctgctt | cttcttcttc | aaaatctctc | tcttcaccaa | atcctcagaa | 60 |
| gatgagcaac | gacaaggata | gcttcaacgt | ctccgatctt | actgctgctc | ttaaggacga | 120 |
| ggatcgagct | ggccttgtca | atgctctaaa | gaacaagctg | cagaatctgg | ctggtcagcg | 180 |
| ttctgatgtg | ctcgagaatc | tgactcccaa | tgtgagaaag | cgcgttgatg | ccttgaggga | 240 |
| tatacagagc | caacatgatg | aactagaggc | aaaattccgt | gaggagagag | ctattcttga | 300 |
| agccaagtat | caaacgctgt | atcagccttt | gtatgtcaag | cgttatgaga | ttgtgaatgg | 360 |
| cactactgaa | gttgaactgg | ctccagagga | tgataccaag | gtggaccaag | agaggagaa | 420 |
| aactgcagaa | gagaaaggag | ttccaagttt | ctggctgaca | gctctgaaaa | ataacgatgt | 480 |
| tatttccgag | gaggtcacag | agcgtgatga | aggggctctc | aaatatctta | agatattaa | 540 |
| gtggtgcaag | attgaagagc | ctaaaggatt | caaacttgag | ttttctttg | acacgaatcc | 600 |
| gtattttaag | aacactgtct | tgacaaagtc | ttatcatatg | attgatgaag | atgagccact | 660 |
| gcttgagaag | gctatgggga | cagaaattga | ttggtatcct | ggaaagtgtc | taactcagaa | 720 |
| gattctcaag | aagaagccta | agaaaggttc | aaagaatact | aaaccaatca | ccaaactcga | 780 |
| agattgtgaa | agcttcttca | acttctttag | tcctccagaa | gttccggatg | aagatgaaga | 840 |
| tatcgacgag | gaaagagctg | aggatcttca | aaacctgatg | gaacaagatt | atgacatcgg | 900 |
| atctactatt | cgggaaaaga | ttattcctcg | tgctgtctca | tggtttactg | gtgaggctat | 960 |
| ggaagcagag | gattttgaaa | tagatgacga | tgaggaagat | gacattgatg | aggatgaaga | 1020 |
| tgaggaagac | gaagaggatg | aggaggacga | tgatgatgag | gatgaagaag | aaagcaagac | 1080 |
| caaaaagaag | ccatcaatcg | gcaacaagaa | gggagggaga | tctcagatag | ttggtgaagg | 1140 |
| taaacaagat | gagaggccac | ccgaatgcaa | gcaacagtaa | tcttttacta | cgctctacca | 1200 |
| gacataaaag | gattgcgtga | aaatataatt | caggtcattc | tctgttcatc | aagaatgagg | 1260 |
| attgagaaaa | ggtttggga | tttttaaaag | tgaaattcat | cttgtaggag | tttcgttcgt | 1320 |
| ttttctattg | gtgtgtttat | tttctctaaa | gcactttaat | aatataccct | ggtatttaat | 1380 |
| ttatgaatca | agcatcatca | tccctagtct | ctgcattcac | tacttcatcc | cctacctaaa | 1440 |
| ctttgtcgac | gaaagagatt | ttaataacca | tttagatagt | aatgggtagt | gggaatgatc | 1500 | attattcttt tgttcaccgt cctttgattt tcaatggtaa ccattttgtt gtgtaag        1557

<210> SEQ ID NO 25
<211> LENGTH: 372
<212> TYPE: PRT
<213> ORGANISM: Arabidopsis thaliana

<400> SEQUENCE: 25

```
Met Ser Asn Asp Lys Asp Ser Phe Asn Val Ser Asp Leu Thr Ala Ala
1               5                   10                  15
Leu Lys Asp Glu Asp Arg Ala Gly Leu Val Asn Ala Leu Lys Asn Lys
            20                  25                  30
Leu Gln Asn Leu Ala Gly Gln Arg Ser Asp Val Leu Glu Asn Leu Thr
        35                  40                  45
Pro Asn Val Arg Lys Arg Val Asp Ala Leu Arg Asp Ile Gln Ser Gln
    50                  55                  60
His Asp Glu Leu Glu Ala Lys Phe Arg Glu Arg Ala Ile Leu Glu
65                  70                  75                  80
Ala Lys Tyr Gln Thr Leu Tyr Gln Pro Leu Tyr Val Lys Arg Tyr Glu
                85                  90                  95
Ile Val Asn Gly Thr Thr Glu Val Glu Leu Ala Pro Glu Asp Asp Thr
            100                 105                 110
Lys Val Asp Gln Gly Glu Glu Lys Thr Ala Glu Glu Lys Gly Val Pro
        115                 120                 125
Ser Phe Trp Leu Thr Ala Leu Lys Asn Asn Asp Val Ile Ser Glu Glu
    130                 135                 140
Val Thr Glu Arg Asp Glu Gly Ala Leu Lys Tyr Leu Lys Asp Ile Lys
145                 150                 155                 160
Trp Cys Lys Ile Glu Glu Pro Lys Gly Phe Lys Leu Glu Phe Phe Phe
                165                 170                 175
Asp Thr Asn Pro Tyr Phe Lys Asn Thr Val Leu Thr Lys Ser Tyr His
            180                 185                 190
Met Ile Asp Glu Asp Glu Pro Leu Leu Glu Lys Ala Met Gly Thr Glu
        195                 200                 205
Ile Asp Trp Tyr Pro Gly Lys Cys Leu Thr Gln Lys Ile Leu Lys Lys
    210                 215                 220
Lys Pro Lys Lys Gly Ser Lys Asn Thr Lys Pro Ile Thr Lys Leu Glu
225                 230                 235                 240
Asp Cys Glu Ser Phe Phe Asn Phe Phe Ser Pro Pro Glu Val Pro Asp
                245                 250                 255
Glu Asp Glu Asp Ile Asp Glu Glu Arg Ala Glu Asp Leu Gln Asn Leu
            260                 265                 270
Met Glu Gln Asp Tyr Asp Ile Gly Ser Thr Ile Arg Glu Lys Ile Ile
        275                 280                 285
Pro Arg Ala Val Ser Trp Phe Thr Gly Glu Ala Met Glu Ala Glu Asp
    290                 295                 300
Phe Glu Ile Asp Asp Asp Glu Glu Asp Ile Asp Glu Asp Glu Asp
305                 310                 315                 320
Glu Glu Asp Glu Glu Asp Glu Asp Asp Asp Glu Asp Glu Glu
                325                 330                 335
Glu Ser Lys Thr Lys Lys Pro Ser Ile Gly Asn Lys Lys Gly Gly
            340                 345                 350
Arg Ser Gln Ile Val Gly Glu Gly Lys Gln Asp Glu Arg Pro Pro Glu
        355                 360                 365
```

Cys Lys Gln Gln
    370

<210> SEQ ID NO 26
<211> LENGTH: 1575
<212> TYPE: DNA
<213> ORGANISM: Arabidopsis thaliana

<400> SEQUENCE: 26

```
gtgtcttatt tcggtctggt cattttctca aagcccttt agttatttat atatatattc      60
tctgtctcgt atttgtcccc aaaaatctag ggttttaagg tttcttatcc ttcctcttcc    120
tccgccagat tctttctgg cgaagatgag caacgacaag gacagcatga acatgtccga     180
tctctccacc gctcttaacg aggaggatcg tgccgggctt gttaatgctc ttaagaacaa    240
gttgcagaat ttggctggac aacactctga tgtccttgaa aacttgactc caccagtcag    300
gaagcgtgtc gagtttctaa gagagattca gaaccaatat gatgagatgg aagcaaaatt    360
ctttgaggag agagcagctc ttgaagctaa gtatcaaaag ttatatcagc ctttatatac    420
caagcgatat gagattgtga atggtgtggt cgaagttgaa ggtgcagctg aagaagtaaa    480
atccgaacaa ggagaagata atcagctga agagaaagga gtaccagatt tctggcttat    540
tgcattgaag aacaatgaaa ttactgcgga agagataact gagcgagatg aaggggctct    600
caagtatctc aaagatatca gtggagtag ggttgaagaa ccaaaagggt tcaagcttga     660
gttttctt gatcagaatc cttacttcaa gaacactgtc ttgaccaaga catatcacat     720
gattgatgaa gatgagccta tccttgagaa ggccctcggg acggagattg agtggtatcc    780
tggaaagtgt ttgacacaga agattctaaa aagaagcca agaaaggat ccaaaaacac      840
aaagccgatc actaagactg aggactgtga gagtttcttc aacttttca gtccacctca    900
agttcctgac gatgatgagg atcttgatga tgacatggct gatgaactcc aaggacaaat   960
ggagcatgat tatgatatcg gttcaacaat caaagagaaa atcatctcgc atgctgtgtc   1020
atggttcact ggtgaagctg ttgaggcaga tgaccttgat attgaggacg acgatgatga   1080
gattgatgaa gatgatgatg aagaggacga ggaagatgat gaggatgacg aggaggagga   1140
tgatgaggat gatgacgagg aggaagaagc agatcaagga agaagagca aaaagaagtc   1200
atcagctggg cacaagaagg ctggaagaag tcaacttgcg gaaggtcaag caggtgagag   1260
gccaccggaa tgtaagcagc agtgaagaag tgaagaatct tggcttagtt atgatgaaga   1320
agaagagtga agagtgtctt tgagccgagg ttgtgtttct ttaatttgca gagtcatggt   1380
ccggtttatt atatatcagt tttgggtgat tggtttgcta tttaaaaaa aaaaatgggt   1440
tctttggttt ggtttgtgtc tcttgattt tccttttgta atgatcttat gaatttgttt   1500
cgagttaatg tcgttctctg gtcagatttc gaattcaatt ctatttatcc tccctcgtta   1560
atgagagaat ttgtg                                                    1575
```

<210> SEQ ID NO 27
<211> LENGTH: 379
<212> TYPE: PRT
<213> ORGANISM: Arabidopsis thaliana

<400> SEQUENCE: 27

Met Ser Asn Asp Lys Asp Ser Met Asn Met Ser Asp Leu Ser Thr Ala
1               5                   10                  15

Leu Asn Glu Glu Asp Arg Ala Gly Leu Val Asn Ala Leu Lys Asn Lys
            20                  25                  30

```
Leu Gln Asn Leu Ala Gly Gln His Ser Asp Val Leu Glu Asn Leu Thr
         35                  40                  45

Pro Pro Val Arg Lys Arg Val Glu Phe Leu Arg Glu Ile Gln Asn Gln
 50                  55                  60

Tyr Asp Glu Met Glu Ala Lys Phe Phe Glu Glu Arg Ala Ala Leu Glu
 65                  70                  75                  80

Ala Lys Tyr Gln Lys Leu Tyr Gln Pro Leu Tyr Thr Lys Arg Tyr Glu
                 85                  90                  95

Ile Val Asn Gly Val Val Glu Val Glu Gly Ala Ala Glu Val Lys
                100                 105                 110

Ser Glu Gln Gly Glu Asp Lys Ser Ala Glu Lys Gly Val Pro Asp
        115                 120                 125

Phe Trp Leu Ile Ala Leu Lys Asn Asn Glu Ile Thr Ala Glu Glu Ile
    130                 135                 140

Thr Glu Arg Asp Glu Gly Ala Leu Lys Tyr Leu Lys Asp Ile Lys Trp
145                 150                 155                 160

Ser Arg Val Glu Glu Pro Lys Gly Phe Lys Leu Glu Phe Phe Phe Asp
                165                 170                 175

Gln Asn Pro Tyr Phe Lys Asn Thr Val Leu Thr Lys Thr Tyr His Met
            180                 185                 190

Ile Asp Glu Asp Glu Pro Ile Leu Glu Lys Ala Leu Gly Thr Glu Ile
        195                 200                 205

Glu Trp Tyr Pro Gly Lys Cys Leu Thr Gln Lys Ile Leu Lys Lys Lys
210                 215                 220

Pro Lys Lys Gly Ser Lys Asn Thr Lys Pro Ile Thr Lys Thr Glu Asp
225                 230                 235                 240

Cys Glu Ser Phe Phe Asn Phe Ser Pro Pro Gln Val Pro Asp Asp
                245                 250                 255

Asp Glu Asp Leu Asp Asp Asp Met Ala Asp Glu Leu Gln Gly Gln Met
        260                 265                 270

Glu His Asp Tyr Asp Ile Gly Ser Thr Ile Lys Glu Lys Ile Ile Ser
    275                 280                 285

His Ala Val Ser Trp Phe Thr Gly Glu Ala Val Glu Ala Asp Asp Leu
290                 295                 300

Asp Ile Glu Asp Asp Asp Glu Ile Asp Glu Asp Asp Glu
305                 310                 315                 320

Asp Glu Glu Asp Asp Glu Asp Glu Glu Asp Asp Glu Asp Asp
                325                 330                 335

Asp Glu Glu Glu Glu Ala Asp Gln Gly Lys Lys Ser Lys Lys Lys Ser
        340                 345                 350

Ser Ala Gly His Lys Lys Ala Gly Arg Ser Gln Leu Ala Glu Gly Gln
    355                 360                 365

Ala Gly Glu Arg Pro Pro Glu Cys Lys Gln Gln
370                 375

<210> SEQ ID NO 28
<211> LENGTH: 1624
<212> TYPE: DNA
<213> ORGANISM: Arabidopsis thaliana

<400> SEQUENCE: 28
gccacccaga aaaaccctc  aagtcttctt cttcttcctc aatctctcca cctcttttca      60
aaccttcttc acactctctc tcaatcaatc cttttcttc tcaaatcttt cagttttgat     120
```

```
ctctaaattt ccagaaaatg agcaacgata aggacagttt caatgtcagc gatctcactt      180
ctgctcttaa agatgaggat cgagctggtc ttgtcaacgc tcttaagaac aagctccaga      240
atctagctgg acaacattct gatgtgctcg agaatctgac tcctaaaatt agaaggcgtg      300
ttgaggtttt gcgggagatt cagggcaaac atgatgaaat agagacaaaa ttccgcgagg      360
agagagctgc tcttgaagcc aagtatcaaa agttatatca gcctttgtat aacaagcgtt      420
atgagattgt gaatggagct actgaagttg aaggggctcc agaggatgct aagatggacc      480
aaggagacga gaaactgcaa gaagagaaag gagtccctag tttctggctg actgctctga      540
aaaataatga tgttatatct gaagagatca cagagcgtga tgaaggagcc ttatatatc      600
ttaaagatat caagtggtgc aagattgaag aaccaaaggg attcaaactt gagtttttct      660
tcgaccagaa tccttacttc aaaaacaccc tattaacaaa ggcgtatcat atgattgatg      720
aagatgagcc tctgcttgag aaggctattg gacagagat tgattggtat cctggaaaat      780
gcttaactca gaagattctt aagaagaagc ctaagaaagg tgcaaagaat gccaagccaa      840
ttaccaaaac tgaagattgt gaaagcttct tcaacttctt caatcctccc caagttcctg      900
atgatgatga agacattgac gaagaaagag ccgaggaact tcagaatctg atggaacaag      960
attatgacat tggttctaca atccgggaga agatcatacc tcatgctgtc tcatggttta     1020
ctggtgaggc tattgaggga gaggagtttg aaatagacaa tgacgatgaa gatgatatcg     1080
atgaggatga agatgaggat gaagaagatg aagacgaaga tgaggaagaa gacgacgaag     1140
atgaggagga gaagtaagc aagaccaaaa agaagccatc agtcttacac aagaaaggag     1200
ggagacctca ggttaccgat gatcaacaag gagagaggcc tcctgaatgc aaacaacagt     1260
aaacaaaatc gaaagtctaa acgaaaaccc agtaaaagaa aaacaaatgt tttgggtttt     1320
gagtgaagtt tcatggccta gttttttgct tccatgtaag gcaaaatgtt ttgaagactg     1380
ctcataggaa tgttgctgta ggcaaaagag tgagtttctc catgtggaga tacttgataa     1440
attattttg gtgcatttgt tttttttttt tttaatcact aagttgaatt ttggtgtgtt      1500
cgtcaaaatt atatcttttt accacttgaa ttaagtctct tttggtttct ttaatttaaa      1560
aataaataaa tcttatcatt gttttttttg tgtggacata agtgtattat tcttattgta     1620
aacc                                                                   1624
```

<210> SEQ ID NO 29
<211> LENGTH: 374
<212> TYPE: PRT
<213> ORGANISM: Arabidopsis thaliana

<400> SEQUENCE: 29

```
Met Ser Asn Asp Lys Asp Ser Phe Asn Val Ser Asp Leu Thr Ser Ala
1               5                   10                  15

Leu Lys Asp Glu Asp Arg Ala Gly Leu Val Asn Ala Leu Lys Asn Lys
            20                  25                  30

Leu Gln Asn Leu Ala Gly Gln His Ser Asp Val Leu Glu Asn Leu Thr
        35                  40                  45

Pro Lys Ile Arg Arg Arg Val Glu Val Leu Arg Glu Ile Gln Gly Lys
    50                  55                  60

His Asp Glu Ile Glu Thr Lys Phe Arg Glu Arg Ala Ala Leu Glu
65                  70                  75                  80

Ala Lys Tyr Gln Lys Leu Tyr Gln Pro Leu Tyr Asn Lys Arg Tyr Glu
                85                  90                  95

Ile Val Asn Gly Ala Thr Glu Val Glu Gly Ala Pro Glu Asp Ala Lys
```

```
            100                 105                 110
Met Asp Gln Gly Asp Glu Lys Thr Ala Glu Lys Gly Val Pro Ser
            115                 120                 125

Phe Trp Leu Thr Ala Leu Lys Asn Asn Asp Val Ile Ser Glu Ile
            130                 135                 140

Thr Glu Arg Asp Glu Gly Ala Leu Ile Tyr Leu Lys Asp Ile Lys Trp
145                 150                 155                 160

Cys Lys Ile Glu Glu Pro Lys Gly Phe Lys Leu Glu Phe Phe Asp
            165                 170                 175

Gln Asn Pro Tyr Phe Lys Asn Thr Leu Leu Thr Lys Ala Tyr His Met
            180                 185                 190

Ile Asp Glu Asp Glu Pro Leu Leu Glu Lys Ala Ile Gly Thr Glu Ile
            195                 200                 205

Asp Trp Tyr Pro Gly Lys Cys Leu Thr Gln Lys Ile Leu Lys Lys Lys
210                 215                 220

Pro Lys Lys Gly Ala Lys Asn Ala Lys Pro Ile Thr Lys Thr Glu Asp
225                 230                 235                 240

Cys Glu Ser Phe Phe Asn Phe Asn Pro Pro Gln Val Pro Asp Asp
            245                 250                 255

Asp Glu Asp Ile Asp Glu Glu Arg Ala Glu Glu Leu Gln Asn Leu Met
            260                 265                 270

Glu Gln Asp Tyr Asp Ile Gly Ser Thr Ile Arg Glu Lys Ile Ile Pro
            275                 280                 285

His Ala Val Ser Trp Phe Thr Gly Glu Ala Ile Glu Gly Glu Phe
            290                 295                 300

Glu Ile Asp Asn Asp Asp Glu Asp Ile Asp Glu Asp Glu Asp
305                 310                 315                 320

Asp Glu Glu Asp Glu Asp Glu Asp Glu Glu Asp Asp Glu Asp Glu
            325                 330                 335

Glu Glu Glu Val Ser Lys Thr Lys Lys Lys Pro Ser Val Leu His Lys
            340                 345                 350

Lys Gly Gly Arg Pro Gln Val Thr Asp Asp Gln Gly Glu Arg Pro
            355                 360                 365

Pro Glu Cys Lys Gln Gln
    370

<210> SEQ ID NO 30
<211> LENGTH: 990
<212> TYPE: DNA
<213> ORGANISM: Arabidopsis thaliana

<400> SEQUENCE: 30
atgagcaacg aagaaaacat caaatctgat aataagagcg gcgattcctc tgatctccct    60
accattcccg ccttagatat tggggcagag gaatgtgatc ttcttgcaga gcttaaggca   120
agtcacttca aattgttgat aaaaattcac acaaacctaa ccttaaagcg accatttgat   180
gtgaaaaaac tctcacctaa agttaccaaa cgtgttctgt tcctcaagga cattcaggtt   240
acacacgatg aactcgaaga gaagtttctt gctgagaaat ctgcattgga ggcaacatat   300
gataatctct acaagccgct ttttgctaag aggtatgaaa ttgtgaatgg tgtggtcgaa   360
gctgaagcag agaaagaagg agttcccaat ttctggttga ttgcaatgaa accaatgaa   420 atgctcgcaa atgagataac ggaaagagat gaggcagcat gaagtatct taaggacatc   480 agatcttgca gagttgaaga cacttcaaga aatttcaagc tggagtttct ctttgattct   540
```

```
aatctttact tcaagaactc ggttctgtct aaaacttacc atgtgaacga tgaagatggt    600
cctgttcttg agaaagtgat tggaacggac atagaatggt ttccaggtaa atgtttgact    660
cataaggttg ttgtgaagaa gaaaacaaag aaagggccaa agaaggtcaa caacatcccc    720
atgaccaaaa cagaaaactg cgagagtttc ttcaatttct tcaagccacc tgagattcct    780
gagattgatg aagttgacga ttacgatgat tttgatacca ttatgacgga agaactacaa    840
aacctgatgg accaagacta tgacattgct gtgacaatcc gagataaact gatccctcat    900
gcagtttcat ggtttacggg agaggctctt gttgatgaag acgattctga tgataatgat    960
gatgatgata atgatgagaa gagtgactaa                                     990
```

<210> SEQ ID NO 31
<211> LENGTH: 329
<212> TYPE: PRT
<213> ORGANISM: Arabidopsis thaliana

<400> SEQUENCE: 31

```
Met Ser Asn Glu Glu Asn Ile Lys Ser Asp Asn Lys Ser Gly Asp Ser
1               5                   10                  15

Ser Asp Leu Pro Thr Ile Pro Ala Leu Asp Ile Gly Ala Glu Glu Cys
            20                  25                  30

Asp Leu Leu Ala Glu Leu Lys Ala Ser His Phe Lys Leu Leu Ile Lys
        35                  40                  45

Ile His Thr Asn Leu Thr Leu Lys Arg Pro Phe Asp Val Lys Lys Leu
    50                  55                  60

Ser Pro Lys Val Thr Lys Arg Val Leu Phe Leu Lys Asp Ile Gln Val
65                  70                  75                  80

Thr His Asp Glu Leu Glu Glu Lys Phe Leu Ala Glu Lys Ser Ala Leu
                85                  90                  95

Glu Ala Thr Tyr Asp Asn Leu Tyr Lys Pro Leu Phe Ala Lys Arg Tyr
            100                 105                 110

Glu Ile Val Asn Gly Val Val Glu Ala Glu Ala Glu Lys Glu Gly Val
        115                 120                 125

Pro Asn Phe Trp Leu Ile Ala Met Lys Thr Asn Glu Met Leu Ala Asn
    130                 135                 140

Glu Ile Thr Glu Arg Asp Glu Ala Ala Leu Lys Tyr Leu Lys Asp Ile
145                 150                 155                 160

Arg Ser Cys Arg Val Glu Asp Thr Ser Arg Asn Phe Lys Leu Glu Phe
                165                 170                 175

Leu Phe Asp Ser Asn Leu Tyr Phe Lys Asn Ser Val Leu Ser Lys Thr
            180                 185                 190

Tyr His Val Asn Asp Glu Asp Gly Pro Val Leu Glu Lys Val Ile Gly
        195                 200                 205

Thr Asp Ile Glu Trp Phe Pro Gly Lys Cys Leu Thr His Lys Val Val
    210                 215                 220

Val Lys Lys Lys Thr Lys Gly Pro Lys Lys Val Asn Asn Ile Pro
225                 230                 235                 240

Met Thr Lys Thr Glu Asn Cys Glu Ser Phe Phe Asn Phe Phe Lys Pro
                245                 250                 255

Pro Glu Ile Pro Glu Ile Asp Glu Val Asp Asp Tyr Asp Asp Phe Asp
            260                 265                 270

Thr Ile Met Thr Glu Glu Leu Gln Asn Leu Met Asp Gln Asp Tyr Asp
        275                 280                 285

Ile Ala Val Thr Ile Arg Asp Lys Leu Ile Pro His Ala Val Ser Trp
```

```
                290             295             300
    Phe Thr Gly Glu Ala Leu Val Asp Glu Asp Ser Asp Asp Asn Asp
    305                 310                 315                 320

Asp Asp Asp Asn Asp Glu Lys Ser Asp
                    325

<210> SEQ ID NO 32
<211> LENGTH: 199
<212> TYPE: PRT
<213> ORGANISM: Artificial sequence
<220> FEATURE:
<223> OTHER INFORMATION: NAP domain

<400> SEQUENCE: 32

Ile Glu Lys Leu Gln Glu Ile Gln Asp Leu Glu Lys Ile Asn Glu
1               5                   10                  15

Lys Ala Ser Asp Glu Val Leu Glu Val Glu Gln Lys Tyr Asn Val Ile
                20                  25                  30

Arg Lys Pro Val Tyr Asp Lys Arg Asn Glu Val Ile Gln Ser Ile Pro
            35                  40                  45

Gly Phe Trp Met Thr Ala Phe Leu Ser His Pro Ala Leu Gly Asp Leu
    50                  55                  60

Leu Thr Glu Glu Asp Gln Lys Ile Phe Lys Tyr Leu Asn Ser Leu Glu
65                  70                  75                  80

Val Glu Asp Ala Lys Asp Val Lys Ser Gly Tyr Ser Ile Thr Phe His
                85                  90                  95

Phe Thr Ser Asn Pro Phe Phe Glu Asp Ala Lys Leu Thr Lys Thr Phe
                100                 105                 110

Thr Phe Leu Glu Glu Gly Thr Thr Lys Ile Thr Ala Thr Pro Ile Lys
            115                 120                 125

Trp Lys Glu Gly Lys Gly Leu Pro Asn Gly Val Asn His Asp Asp Lys
    130                 135                 140

Lys Gly Asn Lys Arg Ala Leu Pro Glu Glu Ser Phe Phe Thr Trp Phe
145                 150                 155                 160

Thr Asp Ala Gln His Lys Glu Asp Ala Gly Asp Glu Ile His Asp Glu
                165                 170                 175

Val Ala Asp Ile Ile Lys Glu Asp Leu Trp Ser Asn Pro Leu Thr Tyr
                180                 185                 190

Phe Asn Asn Asp Ala Asp Glu
        195

<210> SEQ ID NO 33
<211> LENGTH: 10
<212> TYPE: PRT
<213> ORGANISM: Artificial sequence
<220> FEATURE:
<223> OTHER INFORMATION: signature

<400> SEQUENCE: 33

Ser Ile Glu Lys Leu Gln Glu Ile Gln Asp
1               5                   10

<210> SEQ ID NO 34
<211> LENGTH: 6
<212> TYPE: PRT
<213> ORGANISM: Artificial sequence
<220> FEATURE:
<223> OTHER INFORMATION: signature
<220> FEATURE:
<221> NAME/KEY: MISC_FEATURE
```

```
<222> LOCATION: (1)..(1)
<223> OTHER INFORMATION: Xaa is Thr or Ser
<220> FEATURE:
<221> NAME/KEY: MISC_FEATURE
<222> LOCATION: (4)..(4)
<223> OTHER INFORMATION: Xaa is Thr, Asn, Ser, Glu or Asp
<220> FEATURE:
<221> NAME/KEY: MISC_FEATURE
<222> LOCATION: (5)..(5)
<223> OTHER INFORMATION: Xaa is Trp or Phe
<220> FEATURE:
<221> NAME/KEY: MISC_FEATURE
<222> LOCATION: (6)..(6)
<223> OTHER INFORMATION: Xaa is Leu or Phe

<400> SEQUENCE: 34

Xaa Phe Phe Xaa Xaa Xaa
1               5
```

The invention claimed is:

1. A method for increasing seed yield of a plant relative to a corresponding wild type plant, comprising
   (a) introducing a genetic modification in a plant, wherein said genetic modification comprises introducing into the genome of the plant a nucleic acid sequence encoding a NAP1-like protein having at least 95% identity to SEQ ID NO:2,
   (b) selecting for increased expression of said nucleic acid sequence encoding a NAP1-like protein in said plant, and
   (c) selecting for stably transformed plants exhibiting increased seed yield.

2. The method according to claim 1, wherein said genetic modification is effected by homologous recombination.

3. The method according to claim 1, wherein said nucleic acid is derived from a plant.

4. The method according to claim 1, wherein said nucleic acid sequence is SEQ ID NO:1 or encodes SEQ ID NO:2.

5. The method according to claim 1, wherein said increased seed yield comprises one or more of increased number of filled seeds, increased total weight of seeds or increased Harvest Index, each relative to corresponding wild type plants.

6. The method according to claim 1, wherein said nucleic acid encoding a NAP1-like protein is operably linked to a constitutive promoter.

7. A method for production of a transgenic plant having increased seed yield, which method comprises:
   (i) introducing into a plant cell a nucleic acid sequence encoding a NAP1-like protein having at least 95% identity to SEQ ID NO:2; and
   (ii) regenerating and/or growing a plant from the transgenic plant cell; and
   (iii) selecting for a transgenic plant exhibiting increased see yield relative to a corresponding wild type plant.

8. The method according to claim 1, wherein the nucleic acid encoding a NAP1-like protein is operably linked to GOS2 promoter.

* * * * *